(12) United States Patent
Caffaro et al.

(10) Patent No.: US 11,919,934 B2
(45) Date of Patent: Mar. 5, 2024

(54) IL-15 CONJUGATES AND USES THEREOF

(71) Applicant: Synthorx, Inc., La Jolla, CA (US)

(72) Inventors: Carolina E. Caffaro, La Jolla, CA (US); Jerod Ptacin, La Jolla, CA (US); Marcos Milla, La Jolla, CA (US)

(73) Assignee: SYNTHORX, INC., La Jolla, CA (US)

( * ) Notice: Subject to any disclaimer, the term of this patent is extended or adjusted under 35 U.S.C. 154(b) by 665 days.

(21) Appl. No.: 17/001,965

(22) Filed: Aug. 25, 2020

(65) Prior Publication Data

US 2020/0399338 A1 Dec. 24, 2020

Related U.S. Application Data

(63) Continuation of application No. PCT/US2019/019637, filed on Feb. 26, 2019.

(60) Provisional application No. 62/635,133, filed on Feb. 26, 2018.

(51) Int. Cl.
*C07K 14/54* (2006.01)
*C07K 1/107* (2006.01)

(52) U.S. Cl.
CPC ........ *C07K 14/5443* (2013.01); *C07K 1/1075* (2013.01); *C07K 1/1077* (2013.01); *C07K 2317/52* (2013.01); *C07K 2319/31* (2013.01); *C12N 2310/3513* (2013.01); *C12N 2310/3515* (2013.01)

(58) Field of Classification Search
CPC .................................................. C07K 14/5443
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,849,513 A | 7/1989 | Smith et al. |
| 4,876,335 A | 10/1989 | Yamane et al. |
| 4,904,582 A | 2/1990 | Tullis |
| 4,910,300 A | 3/1990 | Urdea et al. |
| 4,948,882 A | 8/1990 | Ruth |
| 4,958,013 A | 9/1990 | Letsinger |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |

(Continued)

FOREIGN PATENT DOCUMENTS

| | | |
|---|---|---|
| EP | 0614907 A1 | 9/1994 |
| EP | 0629633 A2 | 12/1994 |

(Continued)

OTHER PUBLICATIONS

Anonymous, "Designing Optimized Biologics Through Our Expanded Genetic Alphabet Platform." Jan. 1, 2019. XP055811994. https://www.jefferies.com/CMSFiles/Jefferies.com/files/Synthorx%20V2.pdf. 25 pages.
Caffaro et al. "Ex-99.1 Discovery of Pharmacologically Differentiated Interleukin 15 (IL-15) Agonists Employing a Synthetic Biology Platform." Oct. 1, 2019. XP055811406. https://www.sec.gov/Archives/edgar/data/1609727/000119312519287762/d805399dex991.htm. 10 pages.
Caffaro et al. "Discovery of pharmacologically differentiated interleukin 15 (IL-15) agonists employing a synthetic biology platform." Journal for ImmunoTherapy of Cancer. vol. 7, Supplement 1, Nov. 2019, P613, p. 58.
Deiters et al. "Site-specific PEGylation of proteins containing unnatural amino acids." Bioorganic & Medicinal Chemistry Letters 14.23 (2004): 5743-5745.

(Continued)

*Primary Examiner* — Prema M Mertz
(74) *Attorney, Agent, or Firm* — McNeill Baur PLLC

(57) ABSTRACT

Disclosed herein are interleukin (IL) 15 conjugates and use in the treatment of one or more indications. Also described herein include pharmaceutical compositions and kits comprising one or more of IL-15 conjugates.

21 Claims, 22 Drawing Sheets

Specification includes a Sequence Listing.

(56) References Cited

U.S. PATENT DOCUMENTS

| | | |
|---|---|---|
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,235,240 B2 | 6/2007 | Grabstein et al. |
| 7,399,845 B2 | 7/2008 | Seth et al. |
| 7,427,672 B2 | 9/2008 | Imanishi et al. |
| 7,858,081 B2 | 12/2010 | Bernard et al. |
| 8,501,805 B2 | 8/2013 | Seth et al. |
| 8,546,556 B2 | 10/2013 | Seth et al. |
| 8,778,631 B2 | 7/2014 | Voloshin et al. |
| 9,089,614 B2 | 7/2015 | Lin et al. |
| 9,328,159 B2 | 5/2016 | Wong et al. |
| 9,682,934 B2 | 6/2017 | Stafford et al. |
| 9,840,493 B2 | 12/2017 | Yang et al. |
| 9,938,516 B2 | 4/2018 | Zimmerman et al. |
| 9,988,619 B2 | 6/2018 | Zimmerman et al. |
| 10,610,571 B2 | 4/2020 | Ptacin et al. |
| 2004/0171570 A1 | 9/2004 | Allerson et al. |
| 2005/0130923 A1 | 6/2005 | Bhat et al. |
| 2006/0057680 A1 | 3/2006 | Zheng et al. |
| 2006/0074035 A1 | 4/2006 | Hong et al. |
| 2007/0287831 A1 | 12/2007 | Seth et al. |
| 2008/0039618 A1 | 2/2008 | Allerson et al. |
| 2008/0300163 A1 | 12/2008 | Cho et al. |
| 2010/0015723 A1 | 1/2010 | Grabstein et al. |
| 2010/0086517 A1 | 4/2010 | Choi |
| 2016/0367635 A1 | 12/2016 | Wong et al. |
| 2017/0035898 A1 | 2/2017 | Liu et al. |
| 2017/0260137 A1 | 9/2017 | Stafford et al. |
| 2017/0283469 A1 | 10/2017 | Thanos et al. |
| 2017/0369871 A1 | 12/2017 | Ptacin et al. |
| 2018/0051065 A1 | 2/2018 | Yin |
| 2018/0086734 A1 | 3/2018 | Yang et al. |
| 2020/0181220 A1 | 6/2020 | Ptacin et al. |
| 2020/0188484 A1 | 6/2020 | Ptacin et al. |
| 2020/0231644 A1 | 7/2020 | Ptacin et al. |
| 2020/0246467 A1 | 8/2020 | Ptacin et al. |
| 2020/0330601 A1 | 10/2020 | Ptacin et al. |

FOREIGN PATENT DOCUMENTS

| | | |
|---|---|---|
| EP | 3064507 A1 | 9/2016 |
| RU | 2644671 C2 | 2/2018 |
| WO | 9213869 A1 | 8/1992 |
| WO | 9414226 A1 | 6/1994 |
| WO | 9422890 A1 | 10/1994 |
| WO | 9735869 A1 | 10/1997 |
| WO | 1999014226 A3 | 8/1999 |
| WO | 9962923 A2 | 12/1999 |
| WO | 0105801 A1 | 1/2001 |
| WO | 02070533 A2 | 9/2002 |
| WO | 2004007713 A1 | 1/2004 |
| WO | 2004106356 A1 | 12/2004 |
| WO | 2005021570 A1 | 3/2005 |
| WO | 2005026187 A1 | 3/2005 |

(56) References Cited

FOREIGN PATENT DOCUMENTS

| | | |
|---|---|---|
| WO | 2006049297 A1 | 5/2006 |
| WO | 2007015557 A1 | 2/2007 |
| WO | 2007066737 A1 | 6/2007 |
| WO | 2007090071 A2 | 8/2007 |
| WO | 2007134181 A3 | 1/2008 |
| WO | 2008101157 A1 | 8/2008 |
| WO | 2009006478 A2 | 1/2009 |
| WO | 2008150729 A3 | 3/2009 |
| WO | 2008154401 A3 | 3/2009 |
| WO | 2009123216 A1 | 10/2009 |
| WO | 2011043385 A1 | 4/2011 |
| WO | 2012175222 A1 | 12/2012 |
| WO | 2011139699 A3 | 7/2013 |
| WO | 2015038426 A1 | 3/2015 |
| WO | 2015153753 A2 | 10/2015 |
| WO | 2017112528 A2 | 6/2017 |
| WO | 2019028419 A1 | 2/2019 |
| WO | 2019028425 A1 | 2/2019 |
| WO | 2019165453 A1 | 8/2019 |
| WO | 2019166946 A1 | 9/2019 |
| WO | 2020097325 A1 | 5/2020 |
| WO | 2020163532 A1 | 8/2020 |

OTHER PUBLICATIONS

Guo et al. "Immunobiology of the IL-15/IL-15Rα complex as an antitumor and antiviral agent." Cytokine & growth factor reviews 38 (2017): 10-21.

Han et al. "IL-15: IL-15 receptor alpha superagonist complex: high-level co-expression in recombinant mammalian cells, purification and characterization." Cytokine 56.3 (2011): 804-810.

International Search Report and Written Opinion, International Application No. PCT/US2019/019637, dated Jul. 22, 2019, 21 pages.

Chen et al., "Fusion Protein Linkers: Property, Design and Functionality", Adv Drug Deliv Rev., V. 65, N. 10, pp. 1357-1369 (Oct. 15, 2013).

Lightman et al., "Diabetic retinopathy", Clin. Cornerstone, V.5, N.2, pp. 12-21, abstract PMID: 12800477 (2003).

Maeda et al., "Engineering of Functional Chimeric Protein G-Vargula Luciferase", Analytical Biochemistry, V. 249, N. 2, pp. 147-152 (1997).

Muller et al., "Spliceosomal Peptide P140 for Immunotherapy of Systemic Lupus Erythematosus: Results of an Early Phase II Clinical Trial", Arthritis & Rheumatism: Official Journal of the American College of Rheumatology, V. 58, N. 12,pp. 3873-3883 (Dec. 2008).

Orlando M., "Modification of proteins and low molecular weight substances with hydroxyethyl starch (HES)", Inaugural dissertation, Giesen, p. 166, p. 15 (2003).

Rowley et al., "Inhibition of Tumor Growth by NK1.1+ Cells and CD8+ T Cells Activated by IL-15 through Receptor β/ Common y Signaling in trans", The Journal of Immunology, V. 181, N. 12, pp. 8237-8247 (Dec. 15, 2008).

Schweppe K.W., "Significance of progestins in treatment of endometriosis", Zentralbl Gynakol, V.119, Suppl 2, pp. 64-69, abstract PMID: 9441544 (1997).

Treetharnmathurot et al., "Effect of PEG molecular weight and linking chemistry on the biological activity and thermal stability of PEGylated trypsin", International Journal of Pharmaceutics, V. 357, pp. 252-259, abstract, pp. 255,258, Table 2 (2008).

Zhou et al., "Preparation and PEGylation of exendin-4 peptide secreted from yeast Pichia pastoris", European journal of pharmaceutics and biopharmaceutics, V. 72, N. 2, pp. 412-417 (2009).

Beigelman et al. Synthesis of 5'-C-Methyl-D-allo- & L-Talo-ribonucleoside 3'-0-Phosphoramidites & Their Incorporation into Hammerhead Ribozymes. Nucleosides and Nucleotides 14(3-5):901-905 (1995).

Bohringer et al. Synthesis of 5'-deoxy-5'-methylphosphonate linked thymidine oligonucleotides. Tet Lett 34:2723-2726 (1993).

Braasch et al. Locked nucleic acid (LNA): fine-tuning the recognition of DNA and RNA. Chem Bio 8:1-7 (2001).

Chattopadhyay et al. Structural Basis of Inducible Costimulator Ligand Costimulatory Function: State and Functional Mapping of the Determination of the Cell Surface Oligomeric Receptor Binding Site of the Protein. J Immunol. 177:3920-3929 (2006).

Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).

Chen et al. Phosphonate Analogues of Cytosine Arabinoside Monophosphate. Phosphorus, Sulfur and Silicon 177:1783-1786 (2002).

Chen et al. Selective chemical labeling of proteins. Org. Biomol. Chem. 14:5417 (2016).

Collingwood et al. The Synthesis and Incorporation in Oligonucleotides of a Thymidine Dimer Containing an Internucleoside Phosphinate Linkage. Synlett 7:703-705 (1995).

Co-pending U.S. Appl. No. 16/634,487, filed Jan. 27, 2020; also cited herein as US 2020/0231644.

Co-pending U.S. Appl. No. 16/803,816, filed Feb. 27, 2020; also cited herein as US 2020/0188484.

Co-pending U.S. Appl. No. 16/918,930, filed Jul. 1, 2020; also cited herein as US 2020/0330601.

Co-pending U.S. Appl. No. 16/993,967, filed Aug. 14, 2020.
Co-pending U.S. Appl. No. 16/999,638, filed Aug. 21, 2020.
Co-pending U.S. Appl. No. 17/016,003, filed Sep. 9, 2020.

Crooke et al. Pharmacokinetic properties of several novel oligonucleotide analogs in mice. J Pharmacol Exp Ther 277:923-937 (1996).

De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).

Dumas et al. Designing logical codon reassignment—Expanding the chemistry in biology. Chem Sci 6:50-69 (2015).

Elayadi et al. Application of PNA and LNA oligomers to chemotherapy. Curr Opinion Invens Drugs 2:558-561 (2001).

Englisch et al. Chemically Modified Oligonucleotides as Probes and Inhibitors. Angew. Chem. Int. Ed. Eng. 30:613-629 (1991).

Eppacher et al. Synthesis and Incorporation of C(5 ')-Ethynylated Uracil-Derived Phosphoramidites into RNA. Helvetica Chimica Acta 87:3004-3020 (2004).

Fairhurst et al. Synthesis and Hybridisation Properties of Phosphonamidate Ester Modified Nucleic Acid. Synlett 4:467-472 (2001).

Gallier et al. Ex-Chiral-Pool Synthesis of 13-Hydroxyphosphonate Nucleoside Analogues. Eur J Org Chem 6:925-933 (2007).

Geze et al. J. Am. Chem. Soc, 1983, 105(26), 7638-7640.

Gong et al. Recent advances in bioorthogonal reactions for site-specific protein labeling and engineering. Tetrahedron Letters 56:2123-2131 (2015).

Hampton et al. Design of substrate-site-directed inhibitors of adenylate kinase and hexokinase. Effect of substrate substituents on affinity on affinity for the adenine nucleotide sites. J Med Chem 19:1371-1377 (1976).

Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).

Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).

Hutter et al. From Phosphate to Bis(methylene) Sulfone: Non-Ionic Backbone Linkers in DNA. Helvetica Chimica Acta 85:2777-2806 (2002).

Jager et al. Oligonucleotide N-alkylphosphoramidates: synthesis and binding to polynucleotides. Biochemistry 27 :724 7-7246 (1988).

Jung et al. Synthesis of phosphonate derivatives of uridine, cytidine, and cytosine arabinoside. Bioorg Med Chem 8:2501-2509 (2000).

(56) References Cited

OTHER PUBLICATIONS

Kabanov et al. A new class of antivirals: antisense oligonucleotides combined with a hydrophobic substituent effectively inhibit influenza virus reproduction and synthesis of virus-specific proteins in MOCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kroschwitz, J.I. The Concise Encyclopedia of Polymer Science and Engineering, Ed., John Wiley & Sons pp. 858-859 (1990).
Kumar et al. The First Analogues of LNA (Locked Nucleic Acids): Phosphorothioate LNA and 2'-Thio-LNA. Bioorg Med Chem Lett 8:2219-2222 (1998).
Letsinger et al. Cholesteryl-conjugated oligonucleotides: Synthesis, properties, and activity as inhibitors of replication of human immunodeficiency virus in cell culture. PNAS 86:6553-6556 (1989).
Lyon et al. Self-hydrolyzing maleimides improve the stability and pharmacological properties of antibody-drug conjugates. Nat. Biotechnol. 32(10):1059-1062 (2014).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleotide Phosphorothioates in Protocols for Oligonucleotides and Analogs, Synthesis and Properties, Humana Press, pp. 165-190 (1997).
Micklefield. Backbone Modification of Nucleic Acids: Synthesis, Structure and Therapeutic Applications. Current Medicinal Chemistry 8:1157-1179 (2001).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Mishra et al. Improved leishmanicidal effect of phosphorotioate antisense oligonucleotides by LDL-mediated delivery. Biochem Biophys Acta 1264:229-237 (1995).
Napolitano et al. Emergent rules for codon choice elucidated by editing rare arginine codons in *Escherichia coli*. PNAS 113(38): E5588-5597 (2016).

Nawrot et al. A novel class of DNA analogs bearing 5'-C-phosphonothymidine units: synthesis and physicochemical and biochemical properties. Oligonucleotides16(1):68-82 (2006).
Nelson et al. N3'—> PS' Oligodeoxyribonucleotide Phosphoramidates: A New Method of Synthesis Based on a Phosphoramidite Amine-Exchange Reaction. J Org Chem 62:7278-7287 (1997).
Neumann et al. Encoding multiple unnatural amino acids via evolution of a quadruplet-decoding ribosome. Nature 464(7287):441-444 (2010).
Nielsen et al. Sequence-selective recognition of DNA by strand displacement with a thymine-substituted polyamide. Science 254:1497-1500 (1991).
Oberhauser et al. Effective incorporation of 2'-O-methyl-oligoribonucleotides into liposomes and enhanced cell association through modification with thiocholesterol. Nucl. Acids Res. 20:533-538 (1992).
Orum et al. Locked nucleic acids: a promising molecular family for gene-function analysis and antisense drug development. Curr Opinion Mol Ther 3:239-243 (2001).
Ostrov et al. Design, synthesis, and testing toward a 57-codon genome. Science 353(6301): 819-822 (2016).
Peyrottes et al. Oligodeoxynucleoside phosphoramidates (P-NH2): synthesis and thermal stability of duplexes with DNA and RNA targets. Nucleic Acids Res 24:1841-1848 (1996).
Saha et al. 5'-Methyl-DNA—A New Oligonucleotide Analog: Synthesis and Biochemical Properties. J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi, Chapter 15, Antisense Research and Applications, Crooke and Lebleu Eds., CRC Press, 1993, 273-288.
Schultz et al. Oligo-2'-fluoro-2'-deoxynucleotide N3'—> PS' phosphoramidates: synthesis and properties. Nucleic Acids Res 24:2966-2973 (1996).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Srivastava et al. Five- and six-membered conformationally locked 2',4'-carbocyclic ribo-thymidines: synthesis, structure, and biochemical studies. J Am Chem Soc 129(26):8362-8379 (2007).
Svinarchuk et al. Inhibition of HIV proliferation in MT-4 cells by antisense oligonucleotide conjugated to lipophilic groups. Biochimie 75:49-54 (1993).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Wan et al. Pyrrolysyl-tRNA synthetase: an ordinary enzyme but an outstanding genetic code expansion tool. Biochimica Biophysica Acta 1844(6): 1059-1070 (2014).
Wang et al. Biophysical and biochemical properties of oligodeoxynucleotides containing 4'-C-and 5'-C-substituted thymidines. Bioorg Med Chem Lett 9:885-890 (1999).
Wang et al. Synthesis of Azole Nucleoside 5 '-Monophosphate Mimics (P1 Ms) and Their Inhibitory Properties of IMP Dehydrogenases. Nucleosides Nucleotides & Nucleic Acids 23(1 & 2):317-337 (2004).
Wu et al. Functionalization of the sugar moiety of oligoribonucleotides on solid support. Bioconjugate Chem 10:921-924 (1999).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
ZON. Chapter 8: Oligonucleotide Phosphorothioates in Protocols for Oligonucleotides and Analogs, Synthesis and Properties. Humana Press (pp. 165-190) (1993).

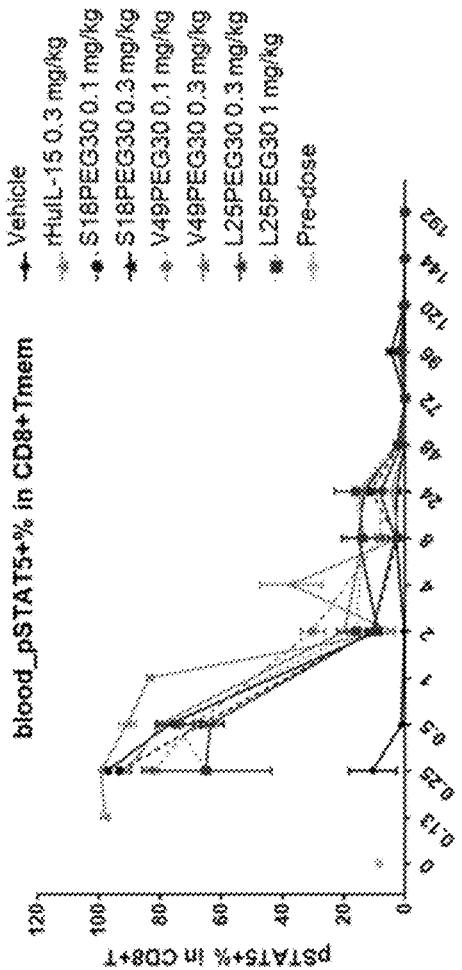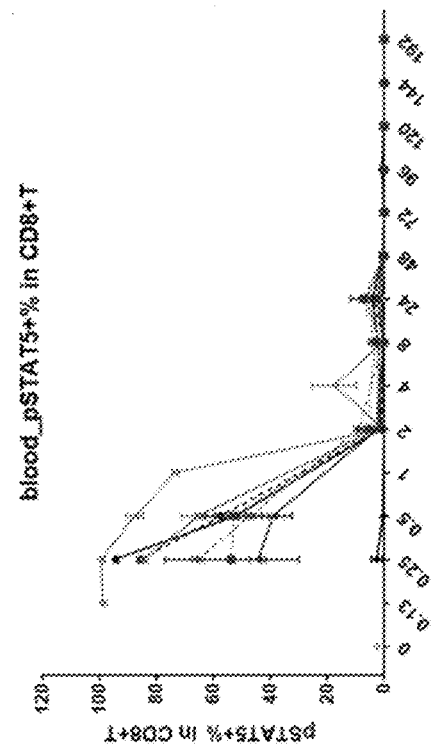
FIG. 14A
FIG. 14B
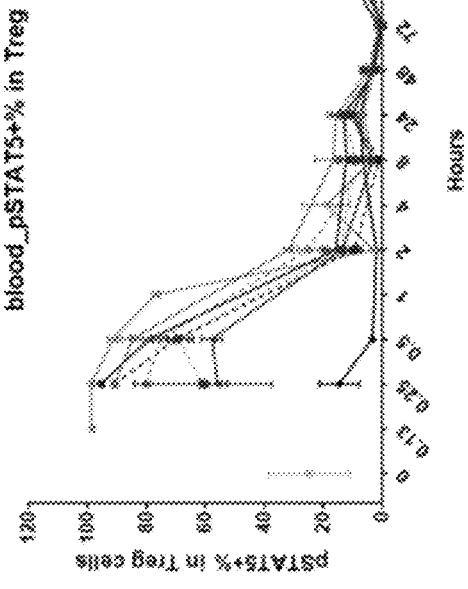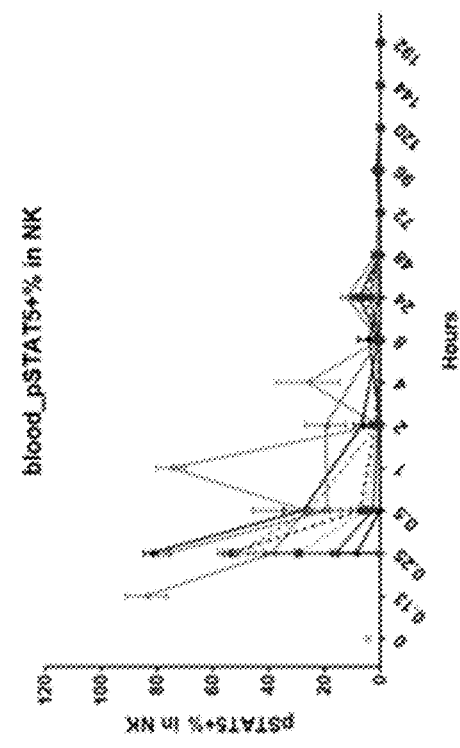
FIG. 14C
FIG. 14D

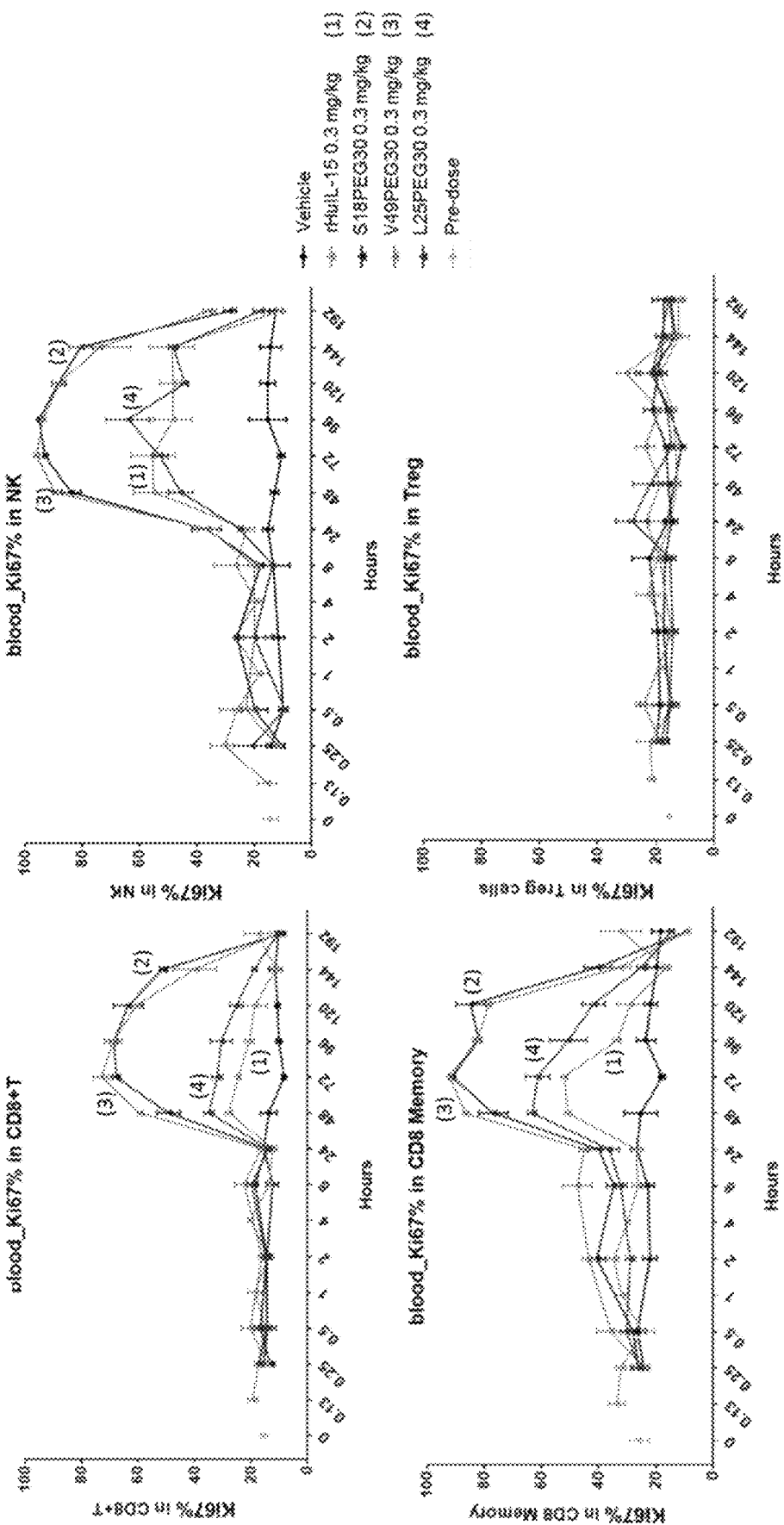

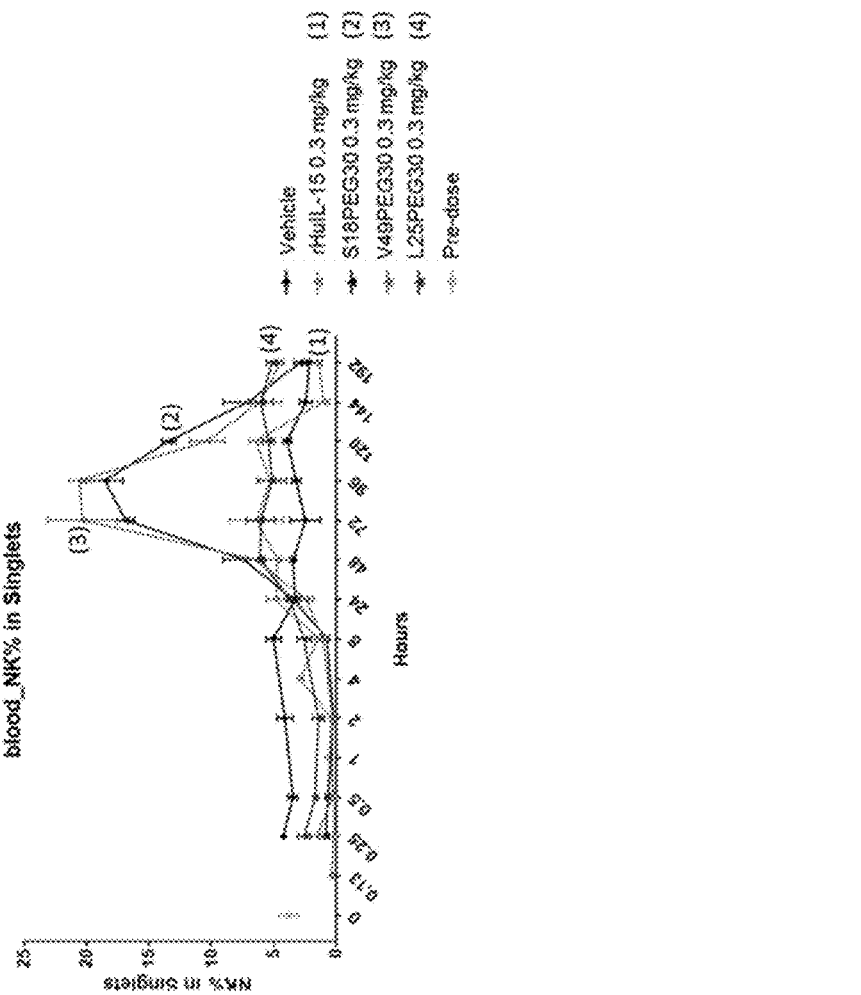
FIG. 16A
FIG. 16B
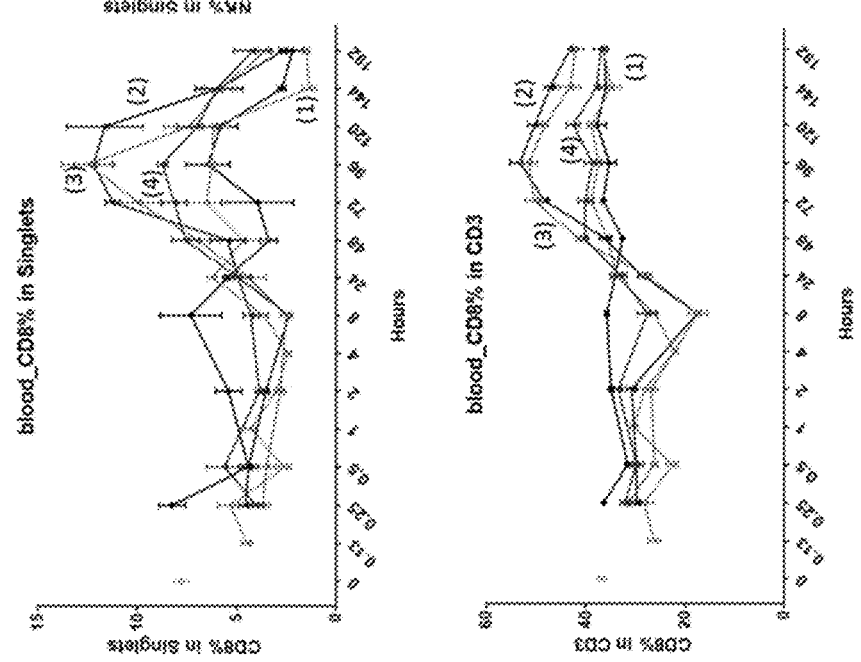
FIG. 16C

SEQUENCE LISTING

```
<160> NUMBER OF SEQ ID NOS: 5

<210> SEQ ID NO 1
<211> LENGTH: 114
<212> TYPE: PRT
<213> ORGANISM: Homo sapiens

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 136
<212> TYPE: PRT
<213> ORGANISM: Homo sapiens

<400> SEQUENCE: 2

Met Asp Phe Gln Val Gln Ile Phe Ser Phe Leu Leu Ile Ser Ala Ser
1               5                   10                  15

Val Ile Met Ser Arg Ala Asn Trp Val Asn Val Ile Ser Asp Leu Lys
                20                  25                  30

Lys Ile Glu Asp Leu Ile Gln Ser Met His Ile Asp Ala Thr Leu Tyr
            35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
    115                 120                 125

Val Gln Met Phe Ile Asn Thr Ser
    130                 135

<210> SEQ ID NO 3
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid except Pro

<400> SEQUENCE: 3

Val Pro Gly Xaa Gly
1               5

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Phe Gln Ser Ser Ser Ser Lys Ala Pro Pro Pro Ser Leu Pro Ser Pro
1               5                   10                  15

Ser Arg Leu Pro Gly Pro Ser Asp Thr Pro Ile Leu Pro Gln
            20                  25                  30

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser
1               5
```

IL-15 CONJUGATES AND USES THEREOF

CROSS-REFERENCE

This application is a continuation of International Patent Application No. PCT/US2019/019,637, filed on Feb. 26, 2019, which claims the benefit of U.S. Provisional Application No. 62/635,133, filed on Feb. 26, 2018, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Aug. 1, 2020, is named 01183-0068-00US_Sequence_Listing.txt and is 3,395 bytes in size.

BACKGROUND OF THE DISCLOSURE

Distinct populations of T cells modulate the immune system to maintain immune homeostasis and tolerance. For example, regulatory T (Treg) cells prevent inappropriate responses by the immune system by preventing pathological self-reactivity while cytotoxic T cells target and destroy infected cells and/or cancerous cells. In some embodiments, modulation of the different populations of T cells provides an option for treatment of a disease or indication.

SUMMARY OF THE DISCLOSURE

Disclosed herein, in certain embodiments, are IL-15 conjugates and use in the treatment of a cancer. In some embodiments, also described herein are methods of modulating the interaction between IL-15 and IL-15 receptors to stimulate or expand specific T cell populations. In additional cases, further described herein are pharmaceutical compositions and kits comprising one or more IL-15 conjugates described herein.

Disclosed herein, in certain embodiments, are modified interleukin 15 (IL-15) polypeptides comprising at least one post-translationally modified unnatural amino acid, wherein the at least one unnatural amino acid is at a residue position that selectively decreases the binding affinity of the modified IL-15 polypeptide with interleukin 15 receptor α (IL-15R α), wherein decrease in binding affinity is relative to binding affinity between a wild-type IL-15 polypeptide and the IL-15Rα, and wherein interaction of the modified IL-15 polypeptide with interleukin 2/interleukin 15 receptor βγ (IL-2/IL-15R βγ) is not significantly affected. In some embodiments, the residue position of the at least one unnatural amino acid is selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position of the at least one unnatural amino acid is selected from D22, A23, T24, L25, Y26, L44, E46, Q48, V49, E53, E89, E90, and E93; Y26, E46, V49, E53, and L25; A23, T24, E89, and E93; D22, L44, Q48, and E90; L25, E53, N77, and S83; or L25 and E53. In some embodiments, the residue position of the at least one unnatural amino acid is selected from E89, E53, E93, V49, E46, Y26, L25, T24, A23, D22, I21, and L52, wherein the residue positions correspond to the positions as set forth in SEQ ID NO: 1. In some embodiments, the residue position of the at least one unnatural amino acid is selected from E46, Y26, V49, E53, T24, N4, K11, N65, L69, S18, H20, and S83, wherein the residue positions correspond to the positions as set forth in SEQ ID NO: 1. In some embodiments, the residue position of the at least one unnatural amino acid is selected from E46, Y26, V49, E53, and T24, wherein the residue positions correspond to the positions as set forth in SEQ ID NO: 1. In some embodiments, the residue position of the at least one unnatural amino acid is selected from E46, V49, E53, and T24, wherein the residue positions correspond to the positions as set forth in SEQ ID NO: 1. In some embodiments, the residue position of the at least one unnatural amino acid is selected from Y26, V49, E53, and T24, wherein the residue positions correspond to the positions as set forth in SEQ ID NO: 1. In some embodiments, the residue position of the at least one unnatural amino acid is selected from V49, E53, and T24, wherein the residue positions correspond to the positions as set forth in SEQ ID NO: 1. In some embodiments, the residue position of the at least one unnatural amino acid is selected from E46 and Y26, wherein the residue positions correspond to the positions as set forth in SEQ ID NO: 1. In some embodiments, the residue position of the at least one unnatural amino acid is E46, wherein the residue position correspond to the position as set forth in SEQ ID NO: 1. In some embodiments, the residue position of the at least one unnatural amino acid is Y26, wherein the residue position correspond to the position as set forth in SEQ ID NO: 1. In some embodiments, the residue position of the at least one unnatural amino acid is V49, wherein the residue position correspond to the position as set forth in SEQ ID NO: 1. In some embodiments, the residue position of the at least one unnatural amino acid is E53, wherein the residue position correspond to the position as set forth in SEQ ID NO: 1. In some embodiments, the residue position of the at least one unnatural amino acid is T24, wherein the residue positions correspond to the position as set forth in SEQ ID NO: 1. In some embodiments, the residue position of the at least one unnatural amino acid is selected from N4, K11, N65, L69, S18, H20, and S83, wherein the residue positions correspond to the positions as set forth in SEQ ID NO: 1. In some embodiments, the at least one unnatural amino acid comprises p-acetyl-L-phenylalanine, p-iodo-L-phenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, isopropyl-L-phenylalanine, or N6-(2-azidoethoxy)-carbonyl-L-lysine. In some embodiments, the at least one unnatural amino acid comprises an unnatural amino acid as set forth in FIG. 2C. In some embodiments, the at least one unnatural amino acid is incorporated into the modified IL-15 polypeptide by an orthogonal tRNA synthetase/tRNA pair. In some embodiments, the modified IL-15 polypeptide is conjugated to a conjugating moiety through the at least one unnatural amino acid. In some embodiments, the conjugating moiety comprises a water-soluble polymer, a protein, or a polypeptide. In some embodiments, the water-soluble polymer comprises: polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof; or a polysaccharide. In some embodiments, the water-soluble polymer comprises PEG. In some embodiments, the PEG is a linear PEG or a branched PEG. In some embodiments, the water-soluble polymer comprises a glycan. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the conjugating moiety comprises a saturated fatty acid. In some embodiments, the saturated fatty acid comprises hexadecanoic acid, tetradecanoic acid, or 15-azidopentadecanoic acid. In some embodiments, the protein comprises an albumin, a transferrin, a transthyretin, or an Fc portion of an antibody. In some embodiments, the polypeptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is directly bound to the at least one unnatural amino acid of the modified IL-15. In some embodiments, the conjugating moiety is indirectly bound to the at least one unnatural amino acid of the modified IL-15 through a linker. In some embodiments, the linker comprises a homobifunctional linker. In some embodiments, the homobifunctional linker comprises Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), 1-(p-Azidosalicylamido)-4-(iodoacetamido)butane (AsIB), N-[4-(p-azidosalicylamido) butyl]-3'-(2'-pyridyldithio)propionamide (APDP), benzophenone-4-iodoacetamide, p-azidobenzoyl hydrazide (ABH), 4-(p-azidosalicylamido)butylamine (AsBA), or p-azidophenyl glyoxal (APG). In some embodiments, the linker comprises a cleavable or a non-cleavable dipeptide linker. In some embodiments, the dipeptide linker comprises Val-Cit, Phe-Lys, Val-Ala, or Val-Lys. In some embodiments, the linker comprises a maleimide group. In some embodiments, the linker comprises a spacer. In some embodiments, the spacer comprises p-aminobenzyl alcohol (PAB), p-aminobenzyoxy carbonyl (PABC), a derivative, or an analog thereof. In some embodiments, the conjugating moiety is capable of extending the serum half-life of the modified IL-15 polypeptide. In some embodiments, the decrease in binding affinity is about 10%, 20%, 30%, 40%, 50%, 60%, 70%, 80%, 90%, 95%, or 99% decrease in binding affinity to IL-15Rα relative to a wild-type IL-15 polypeptide. In some embodiments, the decrease in binding affinity to IL-15Rα is about 1-fold, 2-fold, 3-fold, 4-fold, 5-fold, 6-fold, 7-fold, 8-fold, 9-fold, 10-fold, or more relative to a wild-type IL-15 polypeptide. In some embodiments, the modified IL-15 polypeptide is a functionally active fragment of a full-length IL-15 polypeptide. In some embodiments, the modified IL-15 polypeptide is a recombinant IL-15 polypeptide. In some embodiments, the modified IL-15 polypeptide is a recombinant human IL-15 polypeptide. In some embodiments, the modified IL-15 polypeptide with the decrease in binding affinity to IL-15Rα is capable of expanding effector T (Teff) cell and Natural Killer (NK) cell populations.

Disclosed herein, in certain embodiments, are modified interleukin 15 (IL-15) polypeptides comprising at least one post-translationally modified unnatural amino acid, wherein the at least one unnatural amino acid is at a residue position that does not significantly affect the binding affinity of the modified IL-15 polypeptide with interleukin 15 receptor α (IL-15R α) or IL-2/interleukin 15 receptor βγ (IL-2/IL-15R βγ). In some embodiments, the modified IL-15 polypeptide comprises an extended half-life. In some embodiments, the residue position of the at least one unnatural amino acid is selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position of the at least one unnatural amino acid is selected from D22, A23, T24, L25, Y26, L44, E46, Q48, V49, E53, E89, E90, and E93; Y26, E46, V49, E53, and L25; A23, T24, E89, and E93; D22, L44, Q48, and E90; L25, E53, N77, and S83; or L25 and E53. In some embodiments, the residue position of the at least one unnatural amino acid is selected from M1, S18, H20, K36, K41, G55, D56, S75, S76, N77, G78, V80, T81, S83, and K86, wherein the residue positions correspond to the positions as set forth in SEQ ID NO: 1. In some embodiments, the at least one unnatural amino acid comprises p-acetyl-L-phenylalanine, p-iodo-L-phenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, isopropyl-L-phenylalanine, or N6-(2-azidoethoxy)-carbonyl-L-lysine. In some embodiments, the at least one unnatural amino acid comprises an unnatural amino acid as set forth in FIG. 2C. In some embodiments, the at least one unnatural amino acid is incorporated into the modified IL-15 polypeptide by an orthogonal tRNA synthetase/tRNA pair. In some embodiments, the modified IL-15 polypeptide is conjugated to a conjugating moiety through the at least one unnatural amino acid. In some embodiments, the conjugating moiety comprises a water-soluble polymer, a protein, or a polypeptide. In some embodiments, the water-soluble polymer comprises: polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof; or a polysaccharide. In some embodiments, the water-soluble polymer comprises PEG. In some embodiments, the PEG is a linear PEG or a branched PEG. In some embodiments, the water-soluble polymers comprise a glycan. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the conjugating moiety comprises a saturated fatty acid. In some embodiments, the saturated fatty acid comprises hexadecanoic acid, tetradecanoic acid, or 15-azidopentadecanoic acid. In some embodiments, the protein comprises an albumin, a transferrin, a transthyretin, or an Fc portion of an antibody. In some embodiments, the polypeptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is directly bound to the at least one unnatural amino acid of the modified IL-15. In some embodiments, the conjugating moiety is indirectly bound to the at least one unnatural amino acid of the modified IL-15 through a linker. In some embodiments, the linker comprises a homobifunctional linker. In some embodiments, the homobifunctional linker comprises Lomant's reagent dithiobis (succinimidylpropionate) DSP, 3,3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bis-maleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6α-methyl-α-(2-pyridyldithio) toluamidohexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl (4-iodoactey1)aminobenzoate (sIAB), sulfosuccinimidyl(4-iodoactey1)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), ρ-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M2C2H), 3-(2-pyridyldithio)propionyl hydrazide (PDPH), N-hydroxysuccinimidyl- 4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), 1-(ρ-Azidosalicylamido)-4-(iodoacetamido)butane (AsIB), N-[4-(ρ-azidosalicylamido) butyl]-3'-(2'-pyridyldithio)propionamide (APDP), benzophenone-4-iodoacetamide, p-azidobenzoyl hydrazide (ABH), 4-(ρ-azidosalicylamido)butylamine (AsBA), or p-azidophenyl glyoxal (APG). In some embodiments, the linker comprises a cleavable or a non-cleavable dipeptide linker. In some embodiments, the dipeptide linker comprises Val-Cit, Phe-Lys, Val-Ala, or Val-Lys. In some embodiments, the linker comprises a maleimide group. In some embodiments, the linker comprises a spacer. In some embodiments, the spacer comprises p-aminobenzyl alcohol (PAB), p-aminobenzyoxy carbonyl (PABC), a derivative, or an analog thereof. In some embodiments, the modified IL-15 polypeptide is a functionally active fragment of a full-length IL-15 polypeptide. In some embodiments, the modified IL-15 polypeptide is a recombinant IL-15 polypeptide. In some embodiments, the modified IL-15 polypeptide is a recombinant human IL-15 polypeptide. In some embodiments, the modified IL-15 polypeptide with the decrease in binding affinity to IL-15Rα is capable of expanding effector T (Teff) cell and Natural Killer (NK) cell populations.

Disclosed herein, in certain embodiments, are modified interleukin 15 (IL-15) polypeptides comprising at least one post-translationally modified unnatural amino acid, wherein the at least one unnatural amino acid is at a residue position that selectively decreases the binding affinity of the modified IL-15 polypeptide with interleukin 2/interleukin 15 receptor β (IL-2/IL-15Rβ) but does not affect the interaction with the interleukin 15 receptor α (IL-15R α). In some embodiments, wherein the residue position of the at least one unnatural amino acid is selected from V3, I6, K10, E28, S29, D30, V31, H32, P33, S102, V104, H105, Q108, M109, I111, N112, T113, and S114, wherein the residue positions correspond to the positions as set forth in SEQ ID NO: 1. In some embodiments, the residue position of the at least one unnatural amino acid is selected from V3, K10, S29, D30, H32, H105, Q108, M109, I111, N112, T113, and S114; E28, P33, S102, and V104; or I6 and V31. In some embodiments, the residue position of the at least one unnatural amino acid is selected from N1, N4, S7, D8, K11, D61, T62, E64, N65, I68, L69, and N72. In some embodiments, the residue position of the at least one unnatural amino acid is selected from N4, S7, K11, and D61; D8, E64, N65, I68, and N72; or N1, T62, and L69. In some embodiments, the at least one unnatural amino acid comprises p-acetyl-L-phenylalanine, p-iodo-L-phenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, isopropyl-L-phenylalanine, or N6-(2-azidoethoxy)-carbonyl-L-lysine. In some embodiments, the at least one unnatural amino acid comprises an unnatural amino acid as set forth in FIGS. 1-3. In some embodiments, the at least one unnatural amino acid is incorporated into the modified IL-15 polypeptide by an orthogonal tRNA synthetase/tRNA pair. In some embodiments, the modified IL-15 polypeptide is conjugated to a conjugating moiety through the at least one unnatural amino acid. In some embodiments, the conjugating moiety comprises a water-soluble polymer, a protein, or a polypeptide. In some embodiments, the water-soluble polymer comprises: polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof; or a polysaccharide. In some embodiments, the water-soluble polymer comprises PEG. In some embodiments, the PEG is a linear PEG or a branched PEG. In some embodiments, the water-soluble polymer comprises a glycan. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the conjugating moiety comprises a saturated fatty acid. In some embodiments, the saturated fatty acid comprises hexadecanoic acid, tetradecanoic acid, or 15-azidopentadecanoic acid. In some embodiments, the protein comprises an albumin, a transferrin, a transthyretin, or an Fc portion of an antibody. In some embodiments, the polypeptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is directly bound to the at least one unnatural amino acid of the modified IL-15. In some embodiments, the conjugating moiety is indirectly bound to the at least one unnatural amino acid of the modified IL-15 through a linker. In some embodiments, the linker comprises a homobifunctional linker. In some embodiments, the homobifunctional linker comprises Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bis-maleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido) ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido] hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl (4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), ρ-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M$_2$C$_2$H), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), 1-(ρ-Azidosalicylamido)-4-(iodoacetamido)butane (AsIB), N-[4-(ρ-azidosalicylamido) butyl]-3'-(2'-pyridyldithio)propionamide (APDP), benzophenone-4-iodoacetamide, ρ-azidobenzoyl hydrazide (ABH), 4-(ρ-azidosalicylamido)butylamine (AsBA), or ρ-azidophenyl glyoxal (APG). In some embodiments, the linker comprises a cleavable or a non-cleavable dipeptide linker. In some embodiments, the dipeptide linker comprises Val-Cit, Phe-Lys, Val-Ala, or Val-Lys. In some embodiments, the linker comprises a maleimide group. In some embodiments, the linker comprises a spacer. In some embodiments, the spacer comprises p-aminobenzyl alcohol (PAB), p-aminobenzyoxy carbonyl (PABC), a derivative, or an analog thereof. In some embodiments, the conjugating moiety is capable of extending the serum half-life of the modified IL-15 polypeptide. In some embodiments, the decrease in binding affinity is about 10%, 20%, 30%, 40%, 50%, 60%, 70%, 80%, 90%, 95%, or 99% decrease in binding affinity to IL-15Rα relative to a wild-type IL-15 polypeptide. In some embodiments, the decrease in binding affinity to IL-15Rα is about 1-fold, 2-fold, 3-fold, 4-fold, 5-fold, 6-fold, 7-fold, 8-fold, 9-fold, 10-fold, or more relative to a wild-type IL-15 polypeptide. In some embodiments, the modified IL-15 polypeptide is a functionally active fragment of a full-length IL-15 polypeptide. In some embodiments, the modified IL-15 polypeptide is a recombinant IL-15 polypeptide. In some embodiments, the modified IL-15 polypeptide is a recombinant human IL-15 polypeptide. In some embodiments, the modified IL-15 polypeptide with the decrease in binding affinity to IL-15Rα is capable of expanding effector T (Teff) cell and Natural Killer (NK) cell populations.

Disclosed herein, in certain embodiments, are interleukin 15 (IL-15) conjugates comprising: an isolated and purified IL-15 polypeptide; and a conjugating moiety that binds to the isolated and purified IL-15 polypeptide at an amino acid position selected from N4, E46, D61, E64, N65, I68 and L69, wherein the numbering of the amino acid residues corresponds to SEQ ID NO: 1. In some embodiments, the amino acid position is N4. In some embodiments, the amino acid position is E46. In some embodiments, the amino acid position is D61. In some embodiments, the amino acid position is E64. In some embodiments, the amino acid position is N65. In some embodiments, the amino acid position is I68. In some embodiments, the amino acid position is L69. In some embodiments, the amino acid residue is mutated to cysteine. In some embodiments, the amino acid residue is mutated to lysine. In some embodiments, the amino acid residue selected from N4, E46, N65, and L69 is further mutated to an unnatural amino acid. In some embodiments, the unnatural amino acid comprises p-acetyl-L-phenylalanine, p-iodo-L-phenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, isopropyl-L-phenylalanine, or N6-(2-azidoethoxy)-carbonyl-L-lysine. In some embodiments, the at least one unnatural amino acid comprises an unnatural amino acid as set forth in FIG. 2C. In some embodiments, the IL-15 conjugate has a decreased affinity to IL-15 receptor α (IL-15Rα) subunit relative to a wild-type IL-15 polypeptide. In some embodiments, the decreased affinity is about 10%, 20%, 30%, 40%, 50%, 60%, 70%, 80%, 90%, 95%, or 99% decrease in binding affinity to IL-15Rα relative to a wild-type IL-15 polypeptide. In some embodiments, the decreased affinity to IL-15Rα is about 1-fold, 2-fold, 3-fold, 4-fold, 5-fold, 6-fold, 7-fold, 8-fold, 9-fold, 10-fold, or more relative to a wild-type IL-15 polypeptide. In some embodiments, the conjugating moiety impairs or blocks the binding of IL-15 with IL-15Rα.

Disclosed herein, in certain embodiments, are pharmaceutical compositions comprising: a modified IL-15 polypeptide or an IL-15 conjugate; and a pharmaceutically acceptable excipient. In some embodiments, the pharmaceutical composition is formulated for parenteral administration.

Disclosed herein, in certain embodiments, are methods of treating a proliferative disease or condition in a subject in need thereof, comprising administering to the subject a therapeutically effective amount of a modified IL-15 polypeptide or an IL-15 conjugate. In some embodiments, the proliferative disease or condition is a cancer. In some embodiments, the cancer is a solid tumor cancer. In some embodiments, the solid tumor cancer is bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some embodiments, the cancer is a hematologic malignancy. In some embodiments, the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, methods further comprise administering an additional therapeutic agent. In some embodiments, the modified IL-15 polypeptide or the IL-15 conjugate and the additional therapeutic agent are administered simultaneously. In some embodiments, the modified IL-15 polypeptide or the IL-15 conjugate and the additional therapeutic agent are administered sequentially. In some embodiments, the modified IL-15 polypeptide or the IL-15 conjugate is administered prior to the additional therapeutic agent. In some embodiments, the modified IL-15 polypeptide or the IL-15 conjugate is administered after the administration of the additional therapeutic agent. In some embodiments, the subject is a human.

Disclosed herein, in certain embodiments, are methods of expanding effector T (Teff) cell and Natural Killer (NK) cell populations, comprising: (a) contacting a cell with a modified IL-15 polypeptide or an IL-15 conjugate; and (b) interacting the IL-15 with IL-15Rβ and IL-15Rγ subunits to form an IL-15/IL-15Rβγ complex; wherein the IL-15 conjugate has a decreased affinity to IL-15Rα subunit, and wherein the IL-15/IL-15Rβγ complex stimulates the expansion of Teff and NK cells. In some embodiments, the cell is a eukaryotic cell. In some embodiments, the cell is a mammalian cell. In some embodiments, the cell is a human cell. In some embodiments, the IL-15 conjugate comprises an isolated and purified IL-15 polypeptide and a conjugating moiety that binds to the isolated and purified IL-2 polypeptide at an amino acid residue selected from N4, E46, N65, and L69, wherein the numbering of the amino acid residues corresponds to SEQ ID NO: 1. In some embodiments, the decreased affinity is about 10%, 20%, 30%, 40%, 50%, 60%, 70%, 80%, 90%, 95%, or 99% decrease in binding affinity to IL-15Rα relative to a wild-type IL-15 polypeptide. In some embodiments, the decreased affinity to IL-15Rα is about IL-15Rα 1-fold, 2-fold, 3-fold, 4-fold, 5-fold, 6-fold, 7-fold, 8-fold, 9-fold, 10-fold, or more relative to a wild-type IL-15 polypeptide. In some embodiments, the conjugating moiety impairs or blocks the binding of IL-15 with IL-15Rα.

Disclosed herein, in certain embodiments, are kits comprising a modified IL-15 polypeptide, an IL-15 conjugate, or a pharmaceutical composition.

Disclosed herein, in certain embodiments, are kits comprising a polynucleic acid molecule encoding a modified IL-15 polypeptide or an IL-15 polypeptide.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A illustrates exemplary lysine derivatives. FIG. 2B illustrates exemplary phenylalanine derivatives.

FIG. 3B—UAA #43-89; FIG. 3C—UAA #90-128; FIG. 3D—UAA #129-167). FIG. 3A-FIG. 3D are adopted from Table 1 of Dumas et al., *Chemical Science* 2015, 6, 50-69.

FIG. 9A: rHuIL-15; FIG. 9B: IL15 conjugates N77PEG30 and S83PEG30; and FIG. 9C: IL15 conjugates E46PEG30 and E53PEG30.

FIG. 12A and FIG. 12C: half-life extension (S83PEG30 and N77PEG30); FIG. 12B and FIG. 12D: modulated interaction with IL-15Rα (V49PEG30, E53PEG30 and L25PEG30).

FIG. 14A-FIG. 14D shows percentage of STAT5 phosphorylation in CD8+ T cells (FIG. 14A), CD8 memory cells (FIG. 14B), NK cells (FIG. 14C), and Treg cells (FIG. 14D) in mice dosed with rHuIL-15 or pegylated compounds.

FIG. 15A-FIG. 15D show increased expression of the early proliferation molecular marker Ki67 in CD8+ T (FIG. 15A), NK cells (FIG. 15B), CD8+ Tmem (FIG. 15C) but not Treg cells (FIG. 15D) in animals dosed with pegylated compounds.

FIG. 16A-FIG. 16C show induction of proliferation of CD8+ T cells (FIG. 16A), NK cells (FIG. 16B), and CD8 memory T cells (FIG. 16C).

DETAILED DESCRIPTION OF THE DISCLOSURE

Figure 1:
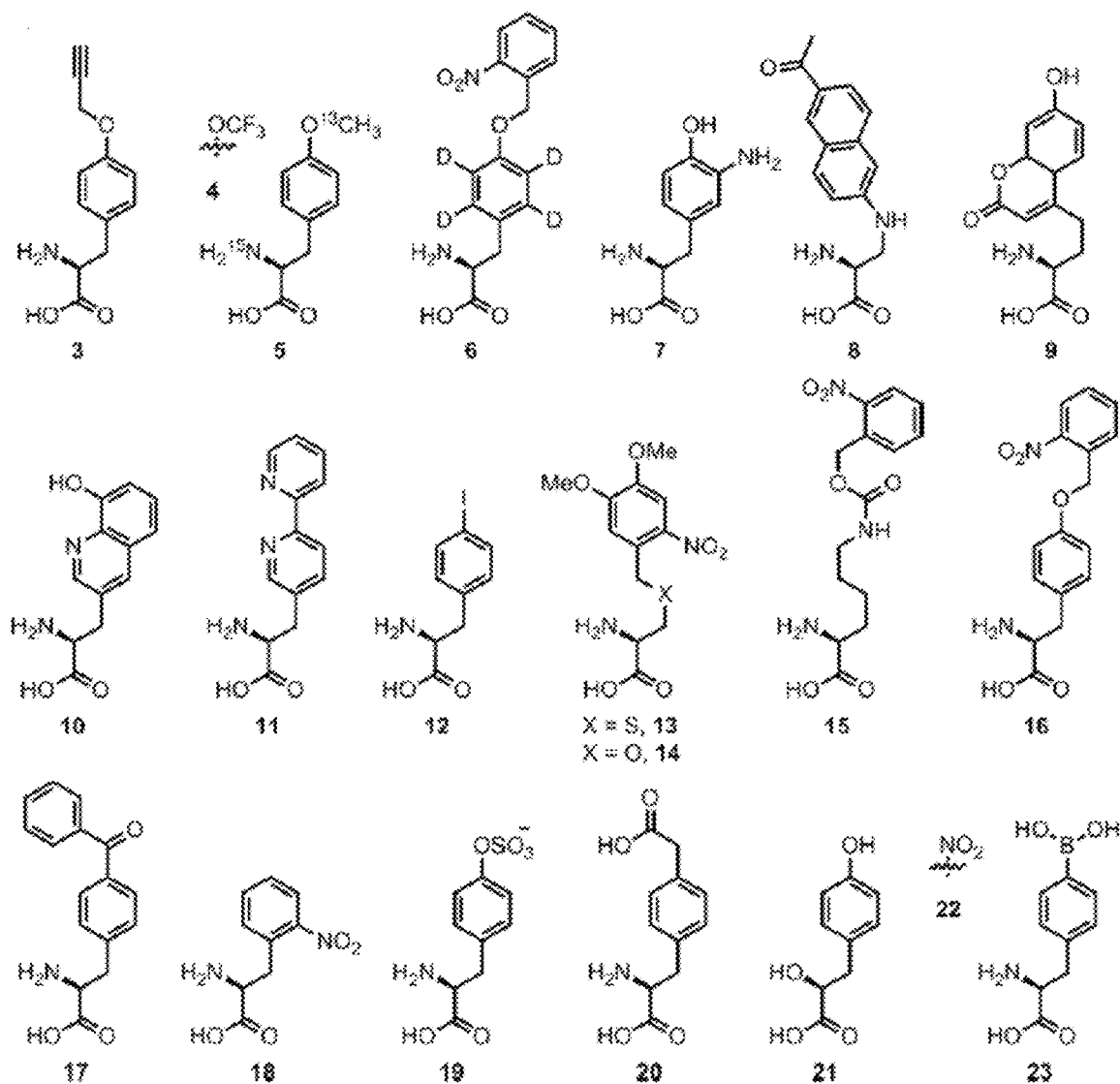
FIG. 1 illustrates exemplary unnatural amino acids. This figure is adapted from FIG. 2 of Young et al., "Beyond the canonical 20 amino acids: expanding the genetic lexicon," J. of Biological Chemistry 285(15): 11039-11044 (2010)

Cancer is a complex group of diseases involving abnormal cell growth with the potential to invade or spread to other parts of the body. Cancer therapies such as radiation and chemotherapy that target cancer drivers and pathways can be successful. In some instances, cancer cells are able to adapt to these therapies, limiting the efficacy of such therapies Immunotherapy, unlike surgery, chemotherapy, or radiation, stimulates the immune system to recognize and kill tumor cells.

Several cytokines are used in immunotherapy for their ability to trigger an immune response. However, current immunotherapies utilizing cytokines result in several adverse effects including toxicity and uncontrolled cellular proliferation. Provided herein are modified cytokines or cytokine conjugates for use in treatment of cancer with ability to stimulate or expand specific T cell and NK populations resulting in improved treatment and reduced adverse events.

Cytokines comprise a family of cell signaling proteins such as chemokines, interferons, interleukins, lymphokines, and tumor necrosis factors. Cytokines are produced by immune cells such as macrophages, B lymphocytes, T lymphocytes and mast cells, endothelial cells, fibroblasts, and different stromal cells. In some instances, cytokines modulate the balance between humoral and cell-based immune responses.

Interleukins are signaling proteins which modulate the development and differentiation of T and B lymphocytes and hematopoietic cells. Interleukins are produced by helper CD4 T lymphocytes, monocytes, macrophages, and endothelial cells. In some cases, there are about 15 interleukins, interleukins 1-13, interleukin 15, and interleukin 17.

Interleukin-15 (IL-15) is a pleiotropic cytokine whose structure is a 14-15 kDa glycoprotein. IL-15 transcription, translation and secretion are regulated through multiple complex mechanisms. IL-15 and IL-15 receptor α (IL-15R α, CD215) proteins are co-expressed predominantly by activated monocytes and dendritic cells (DCs). The transcription of the heterodimer IL-15/IL-15Rα occurs following the interaction of monocytes/DCs with type 1 or type 2 interferons (IFN) or CD40 ligation or agents that act through Toll-like receptors (TLR) that activate NF-kB. Further, IL-15/IL-15Rα protein expression is predominantly controlled at the levels of translation and secretion.

IL-15 signals through a heterotrimeric receptor comprising a unique α chain (IL-15R α), a shared β subunit (IL-15R β, CD132) with IL-2 (CD122) and a common γ subunit (CD132; IL-15R γ) shared with several cytokines. IL-15Rα has high affinity for IL-15 with a $K_d$ about $10^{-11}$ M.

In some embodiments, IL-15 signaling is utilized to modulate T cell responses and subsequently for treatment of cancer. In some embodiments, IL-15 signaling is utilized to simulate proliferation of activated $CD4^-CD8^-$, $CD4^+CD8^+$, $CD4^+$, and $CD8^+$ T cells and their differentiation in defined effector T-cell subsets. In some embodiments, IL-15 signaling is utilized to simulate the generation and proliferation of natural killer (NK) cells. In some embodiments, IL-15 signaling is utilized to promote maintenance and survival of memory CD8 T cells, naïve CD8 T cells, and NK cells. In some embodiments, IL-15 signaling is utilized to induce formation of memory CD8 T cells. In some embodiments, IL-15 signaling is utilized for priming NK cell target-specific activation. In some embodiments, IL-15 signaling does not result in Treg expansion.

Described herein, in some embodiments, are modified IL-15 polypeptides for modulating T cell responses and subsequently for treating cancer. In some embodiments, the modified IL-15 polypeptide comprises decrease binding with interleukin 15 receptor α (IL-15Rα). In some embodiments, the decrease in binding affinity is relative to binding affinity between a wild-type IL-15 polypeptide and the IL-15Rα. In some embodiments, the modified IL-15 polypeptide has little or no effect on interaction of the modified IL-15 polypeptide with interleukin 2/interleukin 15 receptor βγ (IL-2/IL-15R βγ). In some embodiments, the modified IL-15 polypeptide comprises one or more modifications that has little or no effect on the binding affinity of the modified IL-15 polypeptide with the IL-15R α and IL-15R βγ. In some embodiments, the modified IL-15 polypeptide comprises decrease binding with IL-2/IL-15R βγ and IL-15R α interaction is unaffected.

Described herein are modified IL-15 polypeptides or IL-15 conjugates with improved ability to stimulate an anti-tumor response. In some embodiments, the modified IL-15 polypeptides or IL-15 conjugates have improved safety profile. In some embodiments, the modified IL-15 polypeptides or IL-15 conjugates comprise a site-specific pegylation for increasing half-life. In some embodiments, the site-specific pegylation increases half-life and has little or no effect on biological activity. In some embodiments, signaling of the modified IL-15 polypeptides or IL-15 conjugates is biased to IL-15R βγ. In some embodiments, the modified IL-15 polypeptides or IL-15 conjugates comprise a site-specific pegylation for increasing half-life and reducing toxicity. In some embodiments, the site-specific pegylation results in less dosing of the modified IL-15 polypeptides or IL-15 conjugates. In some embodiments, toxicity is reduced by the modified IL-15 polypeptides or IL-15 conjugates blocking IL-15R α interaction. In some embodiments, activity of the modified IL-15 polypeptides or IL-15 conjugates is limited to a tumor site. In some embodiments, the modified IL-15 polypeptides or IL-15 conjugates comprise a site-specific pegylation such that trans-presentation of IL-15 is not required for natural killer (NK) and effector cell proliferation and function. In some embodiments, the modified IL-15 polypeptides or IL-15 conjugates comprise a site-specific pegylation such that clearance is inhibited or prohibited.

Modified IL-15 Polypeptides and IL-15 Conjugates

Described herein, in some embodiments, are modified IL-15 polypeptides. In some instances, the modification is to a natural amino acid. In some instances, the modification is to an unnatural amino acid. In some instances, described herein is an isolated and modified IL-15 polypeptide that comprises at least one unnatural amino acid. In some instances, the IL-15 polypeptide is an isolated and purified mammalian IL-15, for example, a human IL-15 protein. In some cases, the IL-15 polypeptide is a human IL-15 protein. In some cases, the IL-15 polypeptide comprises about 80%, 85%, 90%, 95%, 96%, 97%, 98%, or 99% sequence identity to SEQ ID NO: 1 or 2. In some cases, the IL-15 polypeptide comprises or consists of the sequence of SEQ ID NO: 1 or 2.

In some instances, the modified IL-15 polypeptide is a truncated variant. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the modified IL-15 polypeptide comprises an N-terminal deletion of at least or about 1, 2, 3, 4, 5, 6, 7, 8, 9, 10, 11, 12, 13, 14, 15, 20, or more residues. In some cases, the modified IL-15 polypeptide comprises an N-terminal deletion of at least or about 1, 2, 3, 4, 5, 6, 7, 8, 9, or 10 residues. In some cases, the modified IL-15 polypeptide comprises an N-terminal deletion of at least or about 2 residues. In some cases, the modified IL-15 polypeptide comprises an N-terminal deletion of at least or about 3 residues. In some cases, the modified IL-15 polypeptide comprises an N-terminal deletion of at least or about 4 residues. In some cases, the modified IL-15 polypeptide comprises an N-terminal deletion of at least or about 5 residues. In some cases, the modified IL-15 polypeptide comprises an N-terminal deletion of at least or about 6 residues. In some cases, the modified IL-15 polypeptide comprises an N-terminal deletion of at least or about 7 residues. In some cases, the modified IL-15 polypeptide comprises an N-terminal deletion of at least or about 8 residues. In some cases, the modified IL-15 polypeptide comprises an N-terminal deletion of at least or about 9 residues. In some cases, the modified IL-15 polypeptide comprises an N-terminal deletion of at least or about 10 residues.

In some embodiments, the modified IL-15 polypeptide is a functionally active fragment. In some cases, the functionally active fragment comprises IL-15 region 5-114, 10-114, 15-114, 20-114, 1-110, 5-110, 10-110, 15-110, 20-110, 1-105, 5-105, 10-105, 15-105, 20-105, 1-100, 5-100, 10-100, 15-100, or 20-100, wherein the residue positions are in reference to the positions in SEQ ID NO: 1. In some instances, the functionally active fragment comprises IL-15 region 5-114, 10-114, 15-114, or 20-114, wherein the residue positions are in reference to the positions in SEQ ID NO: 1. In some instances, the functionally active fragment comprises IL-15 region 1-110, 5-110, 10-110, 15-110, or 20-110, wherein the residue positions are in reference to the positions in SEQ ID NO: 1. In some instances, the functionally active fragment comprises IL-15 region 1-105, 5-105, 10-105, 15-105, or 20-105, wherein the residue positions are in reference to the positions in SEQ ID NO: 1. In some instances, the functionally active fragment comprises IL-15 region 1-100, 5-100, 10-100, 15-100, or 20-100, wherein the residue positions are in reference to the positions in SEQ ID NO: 1.

In some embodiments, the functionally active IL-15 fragment comprises an internal deletion. In some cases, the internal deletion comprises a loop region. In some cases, the internal deletion comprises a deletion of 2, 3, 4, 5, 6, 7, 8, 9, 10, 11, 12, 13, 14, 15, or more residues.

In some embodiments, an IL-15 polypeptide described herein comprises at least one unnatural amino acid. In some instances, the residue position of the at least one unnatural amino acid is selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position of the at least one unnatural amino acid is selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position of the at least one unnatural amino acid is selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110. In some embodiments, the residue position of the at least one unnatural amino acid is selected from D14, Q17, S18, K41, S51, L52, G55, D56, A57, S58, S75, S76, N77, N79, V80, T81, S83, G84, E92, K94, N95, K97, and E98. In some embodiments, the residue position of the at least one unnatural amino acid is selected from N1, N4, S7, D8, K11, D61, T62, E64, N65, I68, L69, and N72. In some embodiments, the residue position of the at least one unnatural amino acid is selected from V3, I6, K10, E28, S29, D30, V31, H32, P33, S102, V104, H105, Q108, M109, I111, N112, T113, and S114. In some embodiments, the residue position of the at least one unnatural amino acid is selected from D22, A23, T24, L25, Y26, L44, E46, Q48, V49, E53, E89, E90, and E93. In some embodiments, the residue position of the at least one unnatural amino acid is selected from Y26, E46, V49, E53, and L25. In some embodiments, the residue position of the at least one unnatural amino acid is selected from V3, K10, S29, D30, H32, H105, Q108, M109, I111, N112, T113, and S114. In some embodiments, the residue position of the at least one unnatural amino acid is selected from N4, S7, K11, and D61. In some embodiments, the residue position of the at least one unnatural amino acid is selected from L25, E53, N77, and S83. In some embodiments, the residue position of the at least one unnatural amino acid is selected from L25 and E53. In some embodiments, the residue position of the at least one unnatural amino acid is selected from E46, Y26, V49, E53, T24, N4, K11, N65, L69, S18, H20, and S83. In some embodiments, the residue position of the at least one unnatural amino acid is selected from E46, Y26, V49, E53, and T24. In some embodiments, the residue position of the at least one unnatural amino acid is selected from E46, V49, E53, and T24. In some embodiments, the residue position of the at least one unnatural amino acid is selected from Y26, V49, E53, and T24. In some embodiments, the residue position of the at least one unnatural amino acid is selected from V49, E53, and T24. In some embodiments, the residue position of the at least one unnatural amino acid is selected from E46 and Y26. In some embodiments, the residue position of the at least one unnatural amino acid is E46. In some embodiments, the residue position of the at least one unnatural amino acid is L25. In some embodiments, the residue position of the at least one unnatural amino acid is Y26. In some embodiments, the residue position of the at least one unnatural amino acid is V49. In some embodiments, the residue position of the at least one unnatural amino acid is E53. In some embodiments, the residue position of the at least one unnatural amino acid is T24. In some embodiments, the residue position of the at least one unnatural amino acid is N77. In some embodiments, the residue position of the at least one unnatural amino acid is selected from N4, K11, N65, L69, S18, H20, and S83. An exemplary amino acids sequence for IL-15 is illustrated in Table 1 below.

In some instances, the at least one unnatural amino acid is the C-terminal residue.

In some embodiments, the modified IL-15 polypeptides comprising at least one unnatural amino acid, wherein a residue position of the at least one unnatural amino acid is at a residue position that selectively decreases the binding affinity of the IL-15 polypeptide with the interleukin 15 receptor α (IL-15R α). In some embodiments, the decrease in binding affinity is relative to binding affinity between a wild-type IL-15 polypeptide and the IL-15Rα. In some embodiments, the binding of the modified IL-15 polypeptide to IL-15R α does not affect the interaction of the modified IL-15 polypeptide with interleukin 2/interleukin 15 receptor βγ (IL-2/IL-15R βγ) or improves the interaction of the modified IL-15 polypeptide with IL-2/IL-15R βγ. In some instances, the residue position of the at least one unnatural amino acid is selected from D22, A23, T24, L25, Y26, L44, E46, Q48, V49, E53, E89, E90, and E93, wherein the residue positions correspond to the positions as set forth in SEQ ID

| NAME | SEQUENCE | SEQ ID NO. |
|---|---|---|
| IL-15 (mature form) | NWVNVISDLKKIEDLIQSMHIDATLYTESDVHPSCKVTAMKCF LLELQVISLESGDASIHDTVENLIILANNSLSSNGNVTESGCK ECEELEEKNIKEFLQSFVHIVQMFINTS | 1 |
| IL-15 GenBank: CAA71044.1 (precursor) | MDFQVQIFSFLLISASVIMSRANWVNVISDLKKIEDLIQSMHI DATLYTESDVHPSCKVTAMKCFLLELQVISLESGDASIHDTVE NLIILANNSLSSNGNVTESGCKECEELEEKNIKEFLQSFVHIV QMFINTS | 2 |

In some instances, the at least one unnatural amino acid is located proximal to the N-terminus. As used herein, proximal refers to a residue located at least 1 residue away from the N-terminal residue and up to about 50 residues away from the N-terminal residue. In some cases, the at least one unnatural amino acid is located within the first 10, 20, 30, 40, or 50 residues from the N-terminal residue. In some cases, the at least one unnatural amino acid is located within the first 10 residues from the N-terminal residue. In some cases, the at least one unnatural amino acid is located within the first 20 residues from the N-terminal residue. In some cases, the at least one unnatural amino acid is located within the first 30 residues from the N-terminal residue. In some cases, the at least one unnatural amino acid is located within the first 40 residues from the N-terminal residue. In some cases, the at least one unnatural amino acid is located within the first 50 residues from the N-terminal residue.

In some instances, the at least one unnatural amino acid is the N-terminal residue.

In some instances, the at least one unnatural amino acid is located proximal to the C-terminus. As used herein, proximal refers to a residue located at least 1 residue away from the C-terminal residue and up to about 50 residues away from the C-terminal residue. In some cases, the at least one unnatural amino acid is located within the first 10, 20, 30, 40, or 50 residues from the C-terminal residue. In some cases, the at least one unnatural amino acid is located within the first 10 residues from the C-terminal residue. In some cases, the at least one unnatural amino acid is located within the first 20 residues from the C-terminal residue. In some cases, the at least one unnatural amino acid is located within the first 30 residues from the C-terminal residue. In some cases, the at least one unnatural amino acid is located within the first 40 residues from the C-terminal residue. In some cases, the at least one unnatural amino acid is located within the first 50 residues from the C-terminal residue.

NO: 1. In some embodiments, the residue position of the at least one unnatural amino acid is selected from Y26, E46, V49, E53, and L25, wherein the residue positions correspond to the positions as set forth in SEQ ID NO: 1. In some embodiments, the residue position of the at least one unnatural amino acid is selected from A23, T24, E89, and E93, wherein the residue positions correspond to the positions as set forth in SEQ ID NO: 1. In some embodiments, the residue position of the at least one unnatural amino acid is selected from D22, L44, Q48, and E90, wherein the residue positions correspond to the positions as set forth in SEQ ID NO: 1. In some instances, the residue position of the at least one unnatural amino acid is Y26. In some instances, the residue position of the at least one unnatural amino acid is E46. In some instances, the residue position of the at least one unnatural amino acid is V49. In some instances, the the residue position of the at least one unnatural amino acid is E53. In some instances, the residue position of the at least one unnatural amino acid is L25. In some embodiments, the modified IL-15 polypeptide further comprises a PEG. In some cases, the PEG is conjugated at a residue position selected from D22, A23, T24, L25, Y26, L44, E46, Q48, V49, E53, E89, E90, and E93. In some embodiments, the modified IL-15 polypeptide further comprises a PEG for increased half-life. In some cases, the PEG is conjugated at a residue position selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110, for increased half-life. In some cases, the PEG is conjugated at a residue position selected from N71, N72, and N77. In some cases, the residue conjugated to the PEG is mutated to a natural amino acid. In other cases, the residue conjugated to the PEG is mutated to an unnatural amino acid. In additional cases, the mutation at N71, N72, or N77 further improves a CMC condition (e.g., yield, purity, stability, decreased aggregation, and/or improving protein folding), potency, or a combination thereof.

In some instances, the modified IL-15 polypeptides comprising at least one unnatural amino acid, wherein the at least one unnatural amino acid is at a residue position that selectively decreases the binding affinity of the modified IL-2/IL-15Rβ, IL-15Rγ, or a combination thereof. In some embodiments, the modified IL-15 has little or no effect on interaction with IL-15R α. In some embodiments, the residue position of the at least one unnatural amino acid is selected from N1, V3, N4, I6, S7, D8, K10, K11, E28, S29, D30, V31, H32, P33, D61, T62, E64, N65, I68, L69, N72, S102, V104, H105, Q108, M109, I111, N112, T113, and S114, wherein the residue positions correspond to the positions as set forth in SEQ ID NO: 1. In some embodiments, the at least one unnatural amino acid is at a residue position that selectively decreases the binding affinity of the modified IL-15 polypeptide with IL-2/IL-15Rβ. In some instances, the residue position of the at least one unnatural amino acid is selected from N1, N4, S7, D8, K11, D61, T62, E64, N65, I68, L69, and N72, wherein the residue positions correspond to the positions as set forth in SEQ ID NO: 1. In some instances, the residue position of the at least one unnatural amino acid is selected from N4, S7, K11, and D61. In some instances, the residue position of the at least one unnatural amino acid is selected from D8, E64, N65, I68, and N72. In some instances, the residue position of the at least one unnatural amino acid is selected from N1, T62, and L69. In some instances, the residue position of the at least one unnatural amino acid is N4. In some instances, the residue position of the at least one unnatural amino acid is S7. In some instances, the residue position of the at least one unnatural amino acid is K11. In some instances, the residue position of the at least one unnatural amino acid is D61. In some embodiments, the at least one unnatural amino acid is at a residue position that selectively decreases the binding affinity of the modified IL-15 polypeptide with IL-2/IL-15Rγ. In some instances, the residue position of the at least one unnatural amino acid is selected from V3, I6, K10, E28, S29, D30, V31, H32, P33, S102, V104, H105, Q108, M109, I111, N112, T113, and S114, wherein the residue positions correspond to the positions as set forth in SEQ ID NO: 1. In some instances, the residue position of the at least one unnatural amino acid is selected from V3, K10, S29, D30, H32, H105, Q108, M109, I111, N112, T113, and S114. In some instances, the residue position of the at least one unnatural amino acid is selected from E28, P33, S102, and V104. In some instances, the residue position of the at least one unnatural amino acid is selected from I6 and V31. In some instances, the residue position of the at least one unnatural amino acid is V3. In some instances, the residue position of the at least one unnatural amino acid is K10. In some instances, the residue position of the at least one unnatural amino acid is S29. In some instances, the residue position of the at least one unnatural amino acid is D30. In some instances, the residue position of the at least one unnatural amino acid is H32. In some instances, the residue position of the at least one unnatural amino acid is H105. In some instances, the residue position of the at least one unnatural amino acid is Q108. In some instances, the residue position of the at least one unnatural amino acid is M109. In some instances, the residue position of the at least one unnatural amino acid is I111. In some instances, the residue position of the at least one unnatural amino acid is N112. In some instances, the residue position of the at least one unnatural amino acid is T113. In some instances, the residue position of the at least one unnatural amino acid is S114. In some embodiments, the modified IL-15 polypeptide further comprises a PEG. In some cases, the PEG is conjugated at a residue position selected from N1, V3, N4, I6, S7, D8, K10, K11, E28, S29, D30, V31, H32, P33, D61, T62, E64, N65, I68, L69, N72, S102, V104, H105, Q108, M109, I111, N112, T113, and S114. In some embodiments, the modified IL-15 polypeptide further comprises a PEG for increased half-life. In some cases, the PEG is conjugated at a residue position selected from E13, D14, L15, Q17, 518, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110 for increased half-life. In some cases, the PEG is conjugated at a residue position selected from N71, N72, and N77. In some cases, the residue conjugated to the PEG is mutated to a natural amino acid. In other cases, the residue conjugated to the PEG is mutated to an unnatural amino acid. In additional cases, the mutation at N71, N72, or N77 further improves a CMC condition (e.g., yield, purity, stability, decreased aggregation, and/or improving protein folding), potency, or a combination thereof.

In some cases, the modified IL-15 polypeptides comprising at least one unnatural amino acid, wherein the at least one unnatural amino acid is at a residue position that does not affect the binding affinity of the modified IL-15 polypeptide with the IL-15R α and IL-15R βγ. In some embodiments, the modified IL-15 polypeptide further comprises a PEG for increased half-life. In some embodiments, the modified IL-15 comprises a PEG with no change in biological activity. In some embodiments, the residue is modified for half-life extension. In some cases, the residue position of the at least one unnatural amino acid is selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110, wherein the residue positions correspond to the positions as set forth in SEQ ID NO: 1. In some embodiments, the residue position of the at least one unnatural amino acid is selected from D14, Q17, S18, K41, S51, L52, G55, D56, A57, S58, S75, S76, N77, N79, V80, T81, S83, G84, E92, K94, N95, K97, and E98, wherein the residue positions correspond to the positions as set forth in SEQ ID NO: 1. In some embodiments, the residue position of the at least one unnatural amino acid is selected from E13, L15, M19, H20, K36, V37, T38, S54, H60, I67, N71, G78, K86, E87, and Q101, wherein the residue positions correspond to the positions as set forth in SEQ ID NO: 1. In some embodiments, the residue position of the at least one unnatural amino acid is selected from I21, S34, C35, L44, V63, S73, L74, E82, C85, C88, L91, I96, L100, and F110, wherein the residue positions correspond to the positions as set forth in SEQ ID NO: 1. In some embodiments, the residue position of the at least one unnatural amino acid is selected from N71, N72, and N77, wherein the residue positions correspond to the positions as set forth in SEQ ID NO: 1. In some embodiments, the residue position of the at least one unnatural amino acid is selected from N77 and S83. In some embodiments, the residue position of the at least one unnatural amino acid is D14. In some embodiments, the residue position of the at least one unnatural amino acid is Q17. In some embodiments, the residue position of the at least one unnatural amino acid is S18. In some embodiments, the residue position of the at least one unnatural amino acid is K41. In some embodiments, the residue position of the at least one unnatural amino acid is S51. In some embodiments, the residue position of the at least one unnatural amino acid is L52. In some embodiments, the residue position of the at least one unnatural amino acid is G55. In some embodiments, the residue position of the at least one unnatural amino acid is D56. In some embodiments, the residue position of the at least one unnatural amino acid is A57. In some embodiments, the residue position of the at least one unnatural amino acid is S58. In some embodiments, the residue position of the at least one unnatural amino acid is S75. In some embodiments, the residue position of the at least one unnatural amino acid is S76. In some embodiments, the residue position of the at least one unnatural amino acid is N77. In some embodiments, the residue position of the at least one unnatural amino acid is N79. In some embodiments, the residue position of the at least one unnatural amino acid is V80. In some embodiments, the residue position of the at least one unnatural amino acid is T81. In some embodiments, the residue position of the at least one unnatural amino acid is S83. In some embodiments, the residue position of the at least one unnatural amino acid is G84. In some embodiments, the residue position of the at least one unnatural amino acid is E92. In some embodiments, the residue position of the at least one unnatural amino acid is K94. In some embodiments, the residue position of the at least one unnatural amino acid is N95. In some embodiments, the residue position of the at least one unnatural amino acid is K97. In some embodiments, the residue position of the at least one unnatural amino acid is E98. In some cases, the mutation at N71, N72, or N77 comprises a mutation to a natural amino acid. In some cases, the mutation at N71, N72, or N77 further improves a CMC condition (e.g., yield, purity, stability, decreased aggregation, and/or improving protein folding), potency, or a combination thereof.

In some embodiments, the IL-15 polypeptide comprising at least one unnatural amino acid is further conjugated to a conjugating moiety to generate an IL-15 conjugate. In some cases, the amino acid position of the at least one unnatural amino acid is at N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, or S114, wherein the residue positions correspond to the positions as set forth in SEQ ID NO: 1. In some cases, the amino acid position of the at least one unnatural amino acid is at N1, W2, V3, N4, I6, S7, D8, K10, K11, E13, D14, L15, Q17, 518, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, or S114. In some cases, the conjugating moiety is bound to the at least one unnatural amino acid. In some cases, the conjugating moiety is bound to the N-terminal or the C-terminal amino acid residue. In some instances, the conjugating moiety is directly bound to the at least one unnatural amino acid or a terminal residue. In other instances, the conjugating moiety is indirectly bound to the at least one unnatural amino acid or a terminal residue via a linker described infra.

In some embodiments, the decreased affinity of the IL-15 polypeptide or IL-15 conjugate to an IL-15 receptor α (IL-15Rα) subunit relative to a wild-type IL-15 polypeptide is about 10%, 20%, 30%, 40%, 50%, 60%, 70%, 80%, 90%, 95%, or 99%. In some embodiments, the decreased affinity is about 10%. In some embodiments, the decreased affinity is about 20%. In some embodiments, the decreased affinity is about 40%. In some embodiments, the decreased affinity is about 50%. In some embodiments, the decreased affinity is about 60%. In some embodiments, the decreased affinity is about 80%. In some embodiments, the decreased affinity is about 90%. In some embodiments, the decreased affinity is about 95%. In some embodiments, the decreased affinity is 100%.

In some embodiments, the decreased affinity of the IL-15 polypeptide or IL-15 conjugate to an IL-15 receptor α (IL-15Rα) subunit relative to a wild-type IL-15 polypeptide is about 1-fold, 2-fold, 3-fold, 4-fold, 5-fold, 6-fold, 7-fold, 8-fold, 9-fold, 10-fold, or more. In some embodiments, the decreased affinity is about 1-fold. In some embodiments, the decreased affinity is about 2-fold. In some embodiments, the decreased affinity is about 4-fold. In some embodiments, the decreased affinity is about 5-fold. In some embodiments, the decreased affinity is about 6-fold. In some embodiments, the decreased affinity is about 8-fold. In some embodiments, the decreased affinity is about 10-fold.

In some embodiments, the IL-15 polypeptide or IL-15 conjugate does not interact with IL-15Rα.

In some embodiments, the decreased affinity of the IL-15 polypeptide or IL-15 conjugate to an IL-2 receptor (IL-2R) subunit relative to a wild-type IL-15 polypeptide is about 10%, 20%, 30%, 40%, 50%, 60%, 70%, 80%, 90%, 95%, or 99%. In some embodiments, the IL-2R subunit is IL-2R βγ. In some embodiments, the decreased affinity is about 10%. In some embodiments, the decreased affinity is about 20%. In some embodiments, the decreased affinity is about 40%. In some embodiments, the decreased affinity is about 50%. In some embodiments, the decreased affinity is about 60%. In some embodiments, the decreased affinity is about 80%. In some embodiments, the decreased affinity is about 90%. In some embodiments, the decreased affinity is about 95%. In some embodiments, the decreased affinity is 100%.

In some embodiments, the decreased affinity of the IL-15 polypeptide or IL-15 conjugate to an IL-2 receptor (IL-2R) subunit relative to a wild-type IL-15 polypeptide is about 1-fold, 2-fold, 3-fold, 4-fold, 5-fold, 6-fold, 7-fold, 8-fold, 9-fold, 10-fold, or more. In some embodiments, the IL-2R subunit is IL-2R βγ. In some embodiments, the decreased affinity is about 1-fold. In some embodiments, the decreased affinity is about 2-fold. In some embodiments, the decreased affinity is about 4-fold. In some embodiments, the decreased affinity is about 5-fold. In some embodiments, the decreased affinity is about 6-fold. In some embodiments, the decreased affinity is about 8-fold. In some embodiments, the decreased affinity is about 10-fold.

In some embodiments, the IL-15 polypeptide or IL-15 conjugate does not interact with IL-2Rα.

In some embodiments, the IL-15 polypeptide or IL-15 conjugate has an enhanced half-life. In some instances, the enhanced half-life is compared to a half-life of a wild-type IL-15 protein or wild-type IL-15 conjugate.

In some cases, the enhanced half-life of the IL-15 polypeptide or IL-15 conjugate is at least 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the half-life of the wild-type IL-15 protein or wild-type IL-15 conjugate. In some cases, the enhanced half-life of the IL-15 polypeptide or IL-15 conjugate is at least 90 minutes or longer than the half-life of the wild-type IL-15 protein or wild-type IL-15 conjugate. In some cases, the enhanced half-life of the IL-15 polypeptide or IL-15 conjugate is at least 2 hours or longer than the half-life of the wild-type IL-15 protein or wild-type IL-15 conjugate. In some cases, the enhance half-life of the IL-15 polypeptide or IL-15 conjugate is at least 3 hours or longer than the half-life of the wild-type IL-15 protein or wild-type IL-15 conjugate. In some cases, the enhanced half-life of the IL-15 polypeptide or IL-15 conjugate is at least 4 hours or longer than the half-life of the wild-type IL-15 protein or wild-type IL-15 conjugate. In some cases, the enhanced half-life of the IL-15 polypeptide or IL-15 conjugate is at least 5 hours or longer than the half-life of the wild-type IL-15 protein or wild-type IL-15 conjugate. In some cases, the enhanced half-life of the IL-15 polypeptide or IL-15 conjugate is at least 6 hours or longer than the half-life of the wild-type IL-15 protein or wild-type IL-15 conjugate. In some cases, the enhanced half-life of the IL-15 polypeptide or IL-15 conjugate is at least 10 hours or longer than the half-life of the wild-type IL-15 protein or wild-type IL-15 conjugate. In some cases, the enhanced half-life of the IL-15 polypeptide or IL-15 conjugate is at least 12 hours or longer than the half-life of the wild-type IL-15 protein or wild-type IL-15 conjugate. In some cases, the enhanced half-life of the IL-15 polypeptide or IL-15 conjugate is at least 18 hours or longer than the half-life of the wild-type IL-15 protein or wild-type IL-15 conjugate. In some cases, the enhanced half-life of the IL-15 polypeptide or IL-15 conjugate is at least 24 hours or longer than the half-life of the wild-type IL-15 protein or wild-type IL-15 conjugate. In some cases, the enhanced half-life of the IL-15 polypeptide or IL-15 conjugate is at least 36 hours or longer than the half-life of the wild-type IL-15 protein or wild-type IL-15 conjugate. In some cases, the enhanced half-life of the IL-15 polypeptide or IL-15 conjugate is at least 48 hours or longer than the half-life of the wild-type IL-15 protein or wild-type IL-15 conjugate. In some cases, the enhanced half-life of the IL-15 polypeptide or IL-15 conjugate is at least 3 days or longer than the half-life of the wild-type IL-15 protein or wild-type IL-15 conjugate. In some cases, the enhanced half-life of the IL-15 polypeptide or IL-15 conjugate is at least 4 days or longer than the half-life of the wild-type IL-15 protein or wild-type IL-15 conjugate. In some cases, the enhanced half-life of the IL-15 polypeptide or IL-15 conjugate is at least 5 days or longer than the half-life of the wild-type IL-15 protein or wild-type IL-15 conjugate. In some cases, the enhanced half-life of the IL-15 polypeptide or IL-15 conjugate is at least 6 days or longer than the half-life of the wild-type IL-15 protein or wild-type IL-15 conjugate. In some cases, the enhanced half-life of the IL-15 polypeptide or IL-15 conjugate is at least 7 days or longer than the half-life of the wild-type IL-15 protein or wild-type IL-15 conjugate. In some cases, the enhanced half-life of the IL-15 polypeptide or IL-15 conjugate is at least 10 days or longer than the half-life of the wild-type IL-15 protein or wild-type IL-15 conjugate. In some cases, the enhanced half-life of the IL-15 polypeptide or IL-15 conjugate is at least 12 days or longer than the half-life of the wild-type IL-15 protein or wild-type IL-15 conjugate. In some cases, the enhanced half-life of the IL-15 polypeptide or IL-15 conjugate is at least 14 days or longer than the half-life of the wild-type IL-15 protein or wild-type IL-15 conjugate. In some cases, the enhanced half-life of the IL-15 polypeptide or IL-15 conjugate is at least 21 days or longer than the half-life of the wild-type IL-15 protein or wild-type IL-15 conjugate. In some cases, the enhanced half-life of the IL-15 polypeptide or IL-15 conjugate is at least 28 days or longer than the half-life of the wild-type IL-15 protein or wild-type IL-15 conjugate. In some cases, the enhanced half-life of the IL-15 polypeptide or IL-15 conjugate is at least 30 days or longer than the half-life of the wild-type IL-15 protein or wild-type IL-15 conjugate.

In some cases, the enhanced half-life of the IL-15 polypeptide or IL-15 conjugate is about 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, or 30 days compared to the half-life of the wild-type IL-15 protein or wild-type IL-15 conjugate. In some cases, the biologically active IL-15 polypeptide or IL-15 conjugate has an enhanced half-life of about 90 minutes. In some cases, the biologically active IL-15 polypeptide or IL-15 conjugate has an enhanced half-life of about 2 hours. In some cases, the biologically active IL-15 polypeptide or IL-15 conjugate has an enhanced half-life of about 3 hours. In some cases, the biologically active IL-15 polypeptide or IL-15 conjugate has an enhanced half-life of about 4 hours. In some cases, the biologically active IL-15 polypeptide or IL-15 conjugate has an enhanced half-life of about 5 hours. In some cases, the biologically active IL-15 polypeptide or IL-15 conjugate has an enhanced half-life of about 6 hours. In some cases, the biologically active IL-15 polypeptide or IL-15 conjugate has an enhanced half-life of about 7 hours. In some cases, the biologically active IL-15 polypeptide or IL-15 conjugate has an enhanced half-life of about 8 hours. In some cases, the biologically active IL-15 polypeptide or IL-15 conjugate has an enhanced half-life of about 9 hours. In some cases, the biologically active IL-15 polypeptide or IL-15 conjugate has an enhanced half-life of about 10 hours. In some cases, the biologically active IL-15 polypeptide or IL-15 conjugate has an enhanced half-life of about 11 hours. In some cases, the biologically active IL-15 polypeptide or IL-15 conjugate has an enhanced half-life of about 12 hours. In some cases, the biologically active IL-15 polypeptide or IL-15 conjugate has an enhanced half-life of about 18 hours. In some cases, the biologically active IL-15 polypeptide or IL-15 conjugate has an enhanced half-life of about 24 hours. In some cases, the biologically active IL-15 polypeptide or IL-15 conjugate has an enhanced half-life of about 36 hours. In some cases, the biologically active IL-15 polypeptide or IL-15 conjugate has an enhanced half-life of about 48 hours. In some cases, the biologically active IL-15 polypeptide or IL-15 conjugate has an enhanced half-life of about 3 days. In some cases, the biologically active IL-15 polypeptide or IL-15 conjugate has an enhanced half-life of about 4 days. In some cases, the biologically active IL-15 polypeptide or IL-15 conjugate has an enhanced half-life of about 5 days. In some cases, the biologically active IL-15 polypeptide or IL-15 conjugate has an enhanced half-life of about 6 days. In some cases, the biologically active IL-15 polypeptide or IL-15 conjugate has an enhanced half-life of about 7 days. In some cases, the biologically active IL-15 polypeptide or IL-15 conjugate has an enhanced half-life of about 10 days. In some cases, the biologically active IL-15 polypeptide or IL-15 conjugate has an enhanced half-life of about 12 days. In some cases, the biologically active IL-15 polypeptide or IL-15 conjugate has an enhanced half-life of about 14 days. In some cases, the biologically active IL-15 polypeptide or IL-15 conjugate has an enhanced half-life of about 21 days. In some cases, the biologically active IL-15 polypeptide or IL-15 conjugate has an enhanced half-life of about 28 days. In some cases, the biologically active IL-15 polypeptide or IL-15 conjugate has an enhanced half-life of about 30 days.

In some embodiments, the modified IL-15 polypeptide retains significant signaling potency with interleukin 15 receptor βγ (IL-15Rβγ) signaling complex. In some cases, the signaling potency is compared to a signaling potency between a wild-type IL-15 polypeptide and IL-15Rβγ. In some cases, a difference in receptor signaling potency between the modified IL-15/IL-15Rβγ complex and the wild-type IL-15/IL-15Rβγ complex is less than 1000-fold, less than 500-fold, less than 200-fold, less than 100-fold, less than 50-fold, less than 10-fold, less than 5-fold, less than 4-fold, less than 3-fold, less than 2-fold, or less than 1-fold. In some cases, a difference in receptor signaling potency between the modified IL-15/IL-15Rβγ complex and the wild-type IL-15/IL-15Rβγ complex is greater than 10-fold, greater than 20-fold, greater than 30-fold, greater than 40-fold, greater than 50-fold, greater than 100-fold, greater than 200-fold, greater than 300-fold, greater than 400-fold, or greater than 500-fold. In some instances, the modified IL-15 polypeptide is a partial agonist, e.g., an agonist that activates a receptor (e.g., an IL-15 βγ signaling complex) but has only a partial efficacy at the receptor relative to a full agonist. In some instances, the modified IL-15 polypeptide is a full agonist, e.g., an agonist that activates a receptor (e.g., an IL-15βγ signaling complex) at a maximum response.

In some instances, the receptor signaling potency is measured by an EC50 value. In some instances, the modified IL-15 polypeptide provides an EC50 value that is less than 1000-fold, less than 500-fold, less than 200-fold, less than 100-fold, less than 50-fold, less than 10-fold, less than 5-fold, less than 4-fold, less than 3-fold, less than 2-fold, or less than 1-fold different than an EC50 value of the wild-type IL-15/IL-15Rβγ complex. In some instances, the modified IL-15 polypeptide provides an EC50 value that is greater than 10-fold, greater than 20-fold, greater than 30-fold, greater than 40-fold, greater than 50-fold, greater than 100-fold, greater than 200-fold, greater than 300-fold, greater than 400-fold, or greater than 500-fold different than an EC50 value of the wild-type IL-15/IL-15Rβγ complex.

In some instances, the receptor signaling potency is measured by an ED50 value. In some instances, the modified IL-15 polypeptide provides an ED50 value that is less than 1000-fold, less than 500-fold, less than 200-fold, less than 100-fold, less than 50-fold, less than 10-fold, less than 5-fold, less than 4-fold, less than 3-fold, less than 2-fold, or less than 1-fold different than an EC50 value of the wild-type IL-15/IL-15Rβγ complex. In some instances, the modified IL-15 polypeptide provides an ED50 value that is greater than 10-fold, greater than 20-fold, greater than 30-fold, greater than 40-fold, greater than 50-fold, greater than 100-fold, greater than 200-fold, greater than 300-fold, greater than 400-fold, or greater than 500-fold different than an EC50 value of the wild-type IL-15/IL-15Rβγ complex.

In some embodiments, an IL-15 polypeptide is modified (e.g., pegylated) to extend half-life, improve stability, improve purification yield, improve purity, decrease aggregation, improve protein folding, or a combination thereof, during the Chemistry, Manufacturing and Controls (CMC) stage. In some cases, the IL-15 polypeptide is modified at an amino acid position: N71, N72, or N77, wherein the residue positions correspond to the positions as set forth in SEQ ID NO: 1. In some cases, the IL-15 polypeptide is modified at residue N77, e.g., via pegylation, to extend half-life, improve stability, improve purification yield, improve purity, decrease aggregation, improve protein folding, or a combination thereof, during the CMC stage. In some cases, the IL-15 polypeptide is further modified at position N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, or S114. In some cases, the IL-15 polypeptide is further modified at a position D22, A23, T24, L25, Y26, L44, E46, Q48, V49, E53, E89, E90, or E93, wherein the modification impairs interaction with IL-15Rα. In some cases, the IL-15 polypeptide is further modified at a position N1, N4, S7, D8, K11, D61, T62, E64, N65, I68, L69, or N72, wherein the modification impairs interaction with IL-15Rβ. In some cases, the IL-15 polypeptide is further modified at a position V3, I6, K10, E28, S29, D30, V31, H32, P33, S102, V104, H105, Q108, M109, I111, N112, T113, or S114, wherein the modification impairs interaction with IL-15Rγ. In some cases, the IL-15 polypeptide is further modified at a position E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, or F110, wherein the modification improves half-life extension. In some cases, the IL-15 polypeptide is further modified at one or more of the above positions for impairs interaction with IL-15Rα, impairs interaction with IL-15Rβ, impairs interaction with IL-15Rγ, improves half-life extension, or a combination thereof.

IL-15 Conjugate Precursors

Disclosed herein are IL-15 conjugate precursors, comprising a modified IL-15 polypeptide, wherein one or more amino acids have been mutated from the wild type amino acid. Such precursors are often used with the methods disclosed herein for the treatment of diseases or conditions. In some embodiments, an IL-15 precursor is not conjugated. Such mutations variously comprise additions, deletions, or substitutions. In some cases, the addition comprises inclusion of 1, 2, 3, 4, 5, 6, 7, 8, 9, 10, or more residues at the N-terminus, the C-terminus, or an internal region of the IL-15 polypeptide. In additional cases, the deletion comprises removal of 1, 2, 3, 4, 5, 6, 7, 8, 9, 10, or more residues from the N-terminus, the C-terminus, or within an internal region of the IL-15 polypeptide.

Natural and Unnatural Amino Acids

In some embodiments, an amino acid residue disclosed herein (e.g., within an IL-15 polypeptide) is mutated to lysine, cysteine, histidine, arginine, aspartic acid, glutamic acid, serine, threonine, or tyrosine prior to binding to (or reacting with) a conjugating moiety. For example, the side chain of lysine, cysteine, histidine, arginine, aspartic acid, glutamic acid, serine, threonine, or tyrosine may bind to a conjugating moiety disclosed herein. In some instances, the amino acid residue is mutated to cysteine, lysine, or histidine. In some cases, the amino acid residue is mutated to cysteine. In some cases, the amino acid residue is mutated to lysine. In some cases, the amino acid residue is mutated to histidine. In some cases, the amino acid residue is mutated to tyrosine. In some cases, the amino acid residue is mutated to tryptophan. In some instances, the amino acid residue is located proximal to the N- or C-terminus, at the N- or C-terminus, or at an internal residue position. In some instances, the amino acid residue is the N- or C-terminal residue and the mutation is to cysteine or lysine. In some instances, the amino acid residue is located proximal to the N- or C-terminal residue (e.g., within 50, 40, 30, 20, or 10 residues from the N- or C-terminal residue) and the mutation is to cysteine or lysine.

In some instances, an amino acid residue is added to the N- or C-terminal residue, i.e., the IL-15 polypeptide comprises an additional amino acid residue at either the N- or C-terminus and the additional amino acid residue is cysteine or lysine. In some cases, the additional amino acid residue is cysteine. In some cases, the additional amino acid is conjugated to a conjugating moiety.

In some embodiments, an amino acid residue described herein (e.g., within an IL-15 polypeptide) is mutated to an unnatural amino acid. In some embodiments, an unnatural amino acid is not conjugated with a conjugating moiety. In some embodiments, an IL-15 polypeptide disclosed herein comprises an unnatural amino acid, wherein the IL-15 is conjugated to the protein, wherein the point of attachment is not the unnatural amino acid.

In some embodiments, an amino acid residue disclosed herein (e.g., within an IL-15 polypeptide) is mutated to an unnatural amino acid prior to binding to a conjugating moiety. In some cases, the mutation to an unnatural amino acid prevents or minimizes a self-antigen response of the immune system. As used herein, the term "unnatural amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, N6-[(2-azidoethoxy)carbonyl]-L-lysine (AzK), an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α, α disubstituted amino acid; a β-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling.

In some embodiments, the unnatural amino acid comprises a photoreactive group, which crosslinks, upon irradiation with, e.g., UV.

In some embodiments, the unnatural amino acid comprises a photo-caged amino acid.

In some instances, the unnatural amino acid is a para-substituted, meta-substituted, or an ortho-substituted amino acid derivative.

In some instances, the unnatural amino acid comprises p-acetyl-L-phenylalanine, p-azidomethyl-L-phenylalanine (pAMF), p-iodo-L-phenylalanine, O-methyl-L-tyrosine, p-methoxyphenylalanine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxy-phenylalanine, or 3-iodotyrosine.

In some cases, the unnatural amino acid is phenylselenocysteine.

In some instances, the unnatural amino acid is a benzophenone, ketone, iodide, methoxy, acetyl, benzoyl, or azide containing phenylalanine derivative.

In some instances, the unnatural amino acid is a benzophenone, ketone, iodide, methoxy, acetyl, benzoyl, or azide containing lysine derivative.

In some instances, the unnatural amino acid comprises an aromatic side chain.

In some instances, the unnatural amino acid does not comprise an aromatic side chain.

In some instances, the unnatural amino acid comprises an azido group.

In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics.

In some instances, the unnatural amino acid is dehydroalanine.

In some instances, the unnatural amino acid comprises an aldehyde or ketone group.

In some instances, the unnatural amino acid is a lysine derivative comprising an aldehyde or ketone group.

In some instances, the unnatural amino acid is a lysine derivative comprising one or more O, N, Se, or S atoms at the beta, gamma, or delta position. In some instances, the unnatural amino acid is a lysine derivative comprising O, N, Se, or S atoms at the gamma position.

In some instances, the unnatural amino acid is a lysine derivative wherein the epsilon N atom is replaced with an oxygen atom.

In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is a nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group.

In some instances, the unnatural amino acid comprises a transcyclooctenyl group.

In some instances, the unnatural amino acid comprises a norbornenyl group.

In some instances, the unnatural amino acid comprises a cyclopropenyl group.

In some instances, the unnatural amino acid comprises a diazirine group.

In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-{[(tert-butoxy)carbonyl]amino}hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-{[(benzyloxy)carbonyl]amino}hexanoic acid. In some instances, the unnatural amino acid is 2-amino-6-{[(p-iodobenzyloxy)carbonyl]amino}hexanoic acid. In some instances, the unnatural amino acid is 2-amino-6-{[(p-nitrobenzyloxy)carbonyl]amino}hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine. In some instances, the unnatural amino acid is 2-amino-6-{[(2-azidocyclopentyloxy)carbonyl]amino}hexanoic acid. In some instances, the unnatural amino acid is N6-[(2-azidoethoxy)carbonyl]lysine. In some instances, the unnatural amino acid is 2-amino-6-{[(2-nitrobenzyloxy)carbonyl]amino}hexanoic acid. In some instances, the unnatural amino acid is 2-amino-6-{[(2-cyclooctynyloxy)carbonyl]amino}hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine, In some instances, the unnatural amino acid is N6-(but-2-enoyl)lysine, In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl)oxy)carbonyl)lysine. In some instances, the unnatural amino acid is N6-((bicyclo[2.2.1]hept-5-en-2-ylmethoxy)carbonyl)lysine. In some instances, the unnatural amino acid is cysteinyllysine. In some instances, the unnatural amino acid is N6-((1-(6-nitrobenzo[d][1,3]dioxol-5-yl)ethoxy)carbonyl)lysine. In some instances, the unnatural amino acid is N6-((2-(3-methyl-3H-diazirin-3-yl)ethoxy)carbonyl)lysine. In some instances, the unnatural amino acid is N6-((3-(3-methyl-3H-diazirin-3-yl)propoxy)carbonyl)lysine. In some instances, the unnatural amino acid is N6-((meta nitrobenyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid.

In some embodiments, the unnatural amino acid is incorporated into the IL-15 polypeptide by a repurposed amber, opal, or ochre stop codon.

In some embodiments, the unnatural amino acid is incorporated into the IL-15 polypeptide by a 4-base codon.

In some embodiments, the unnatural amino acid is incorporated into the IL-15 polypeptide by a repurposed rare sense codon or a repurposed common sense codon.

In some embodiments, the unnatural amino acid is incorporated into the IL-15 polypeptide by a synthetic codon comprising an unnatural nucleic acid.

In some instances, the unnatural amino acid is incorporated into the IL-15 by an orthogonal, modified synthetase/ tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the IL-15 polypeptide by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophiius* tRNA$_{CUA}$ pairs, *E. coli* LeuRS (Ec-Leu)/*B. stearothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine and p-methoyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronopheylalanine; and o-nitrobenzyltyrosine.

In some instances, the unnatural amino acid is incorporated into the IL-15 polypeptide by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenoe, ketone, iodide, or azide substituents; O-propargyltyrosine; α-aminocaprylic acid, O-methyl tyrosine, 0-nitrobenzyl cysteine; and 3-(naphthalene-2-ylamino)-2-amino-propanoic acid.

In some instances, the unnatural amino acid is incorporated into the IL-15 polypeptide by a pyrrolysyl-tRNA pair. In some cases, the Py1RS is obtained from an archaebacterial, e.g., from a methanogenic archaebacterial. In some cases, the Py1RS is obtained from *Methanosarcina barkeri*, *Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-$_D$-prolyl-$_L$-lysine, and N-ε-cyclopentyloxycarbonyl-$_L$-lysine; N-ε-Acryloyl-$_L$-lysine; N-ε-[(1-(6-nitrobenzo[d][1,3]dioxol-5-yl)ethoxy)carbonyl]-$_L$-lysine; and N-ε-(1-methylcyclopro-2-enecarboxamido)lysine.

In some instances, an unnatural amino acid is incorporated into an IL-15 polypeptide by a synthetase disclosed in U.S. Pat. Nos. 9,988,619 and 9,938,516. Exemplary UAAs that can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, such synthetases are expressed and used to incorporate UAAs into cytokines in-vivo. In some embodiments, such synthetases are used to incorporate UAAs into cytokines using a cell-free translation system.

In some instances, an unnatural amino acid is incorporated into an IL-15 polypeptide by a naturally occurring synthetase. In some embodiments, an unnatural amino acid is incorporated into a cytokine by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

In some instances, the unnatural amino acid comprises an unnatural amino acid illustrated in FIG. 1.

Figure 2A:
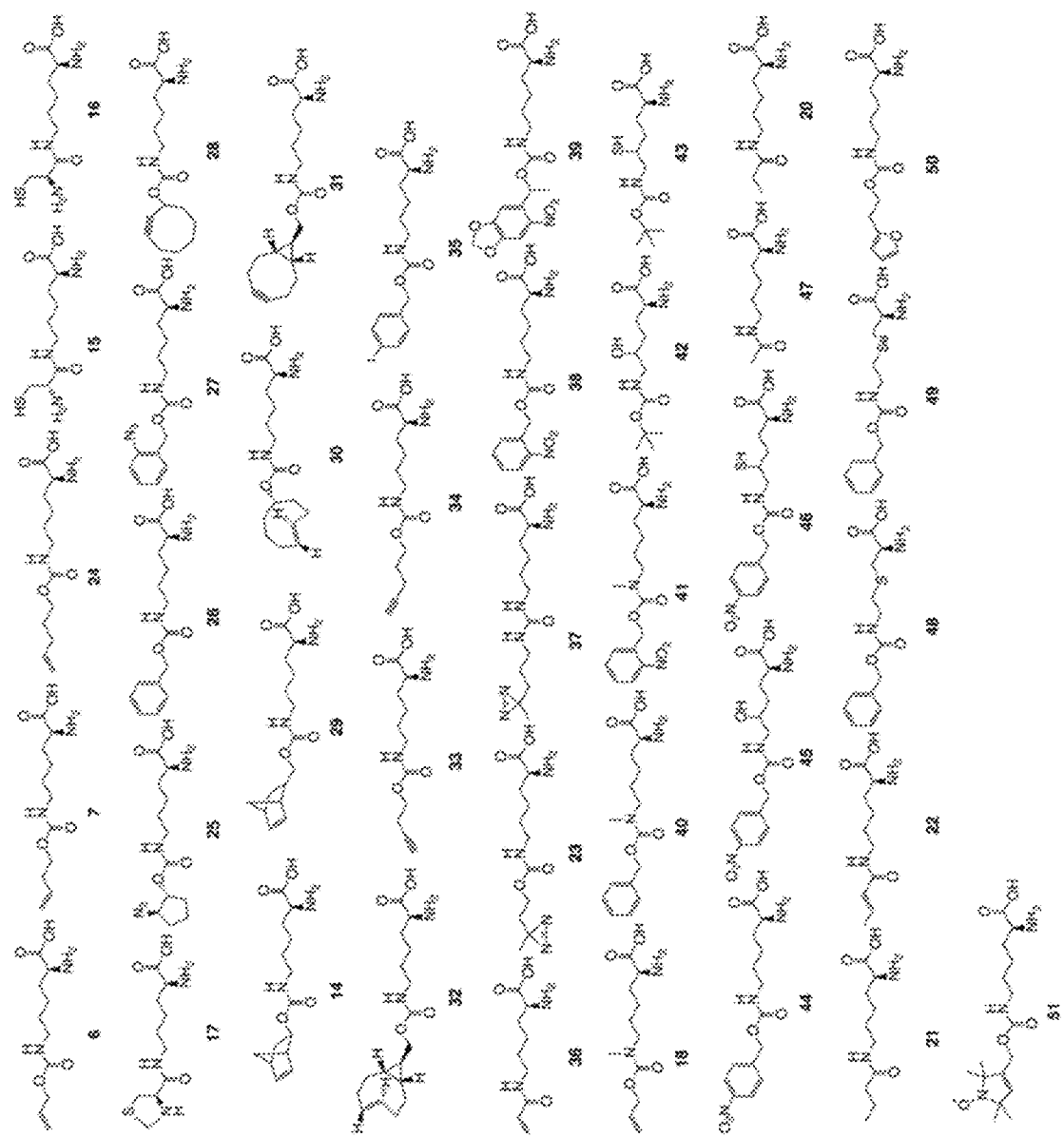
FIG. 2A-FIG. 2B illustrate exemplary unnatural amino acids.
Figure 2B:
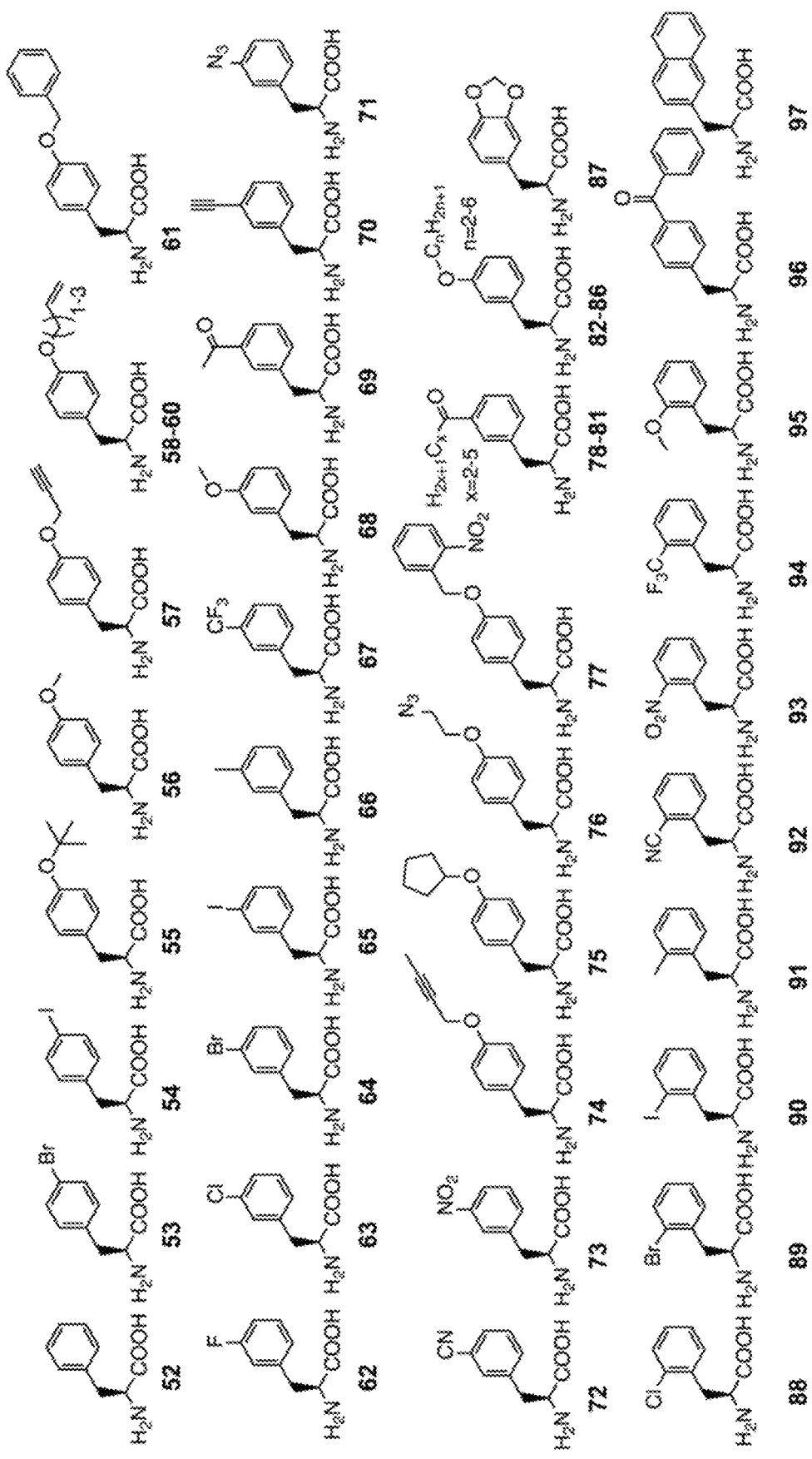
Figure 3A:
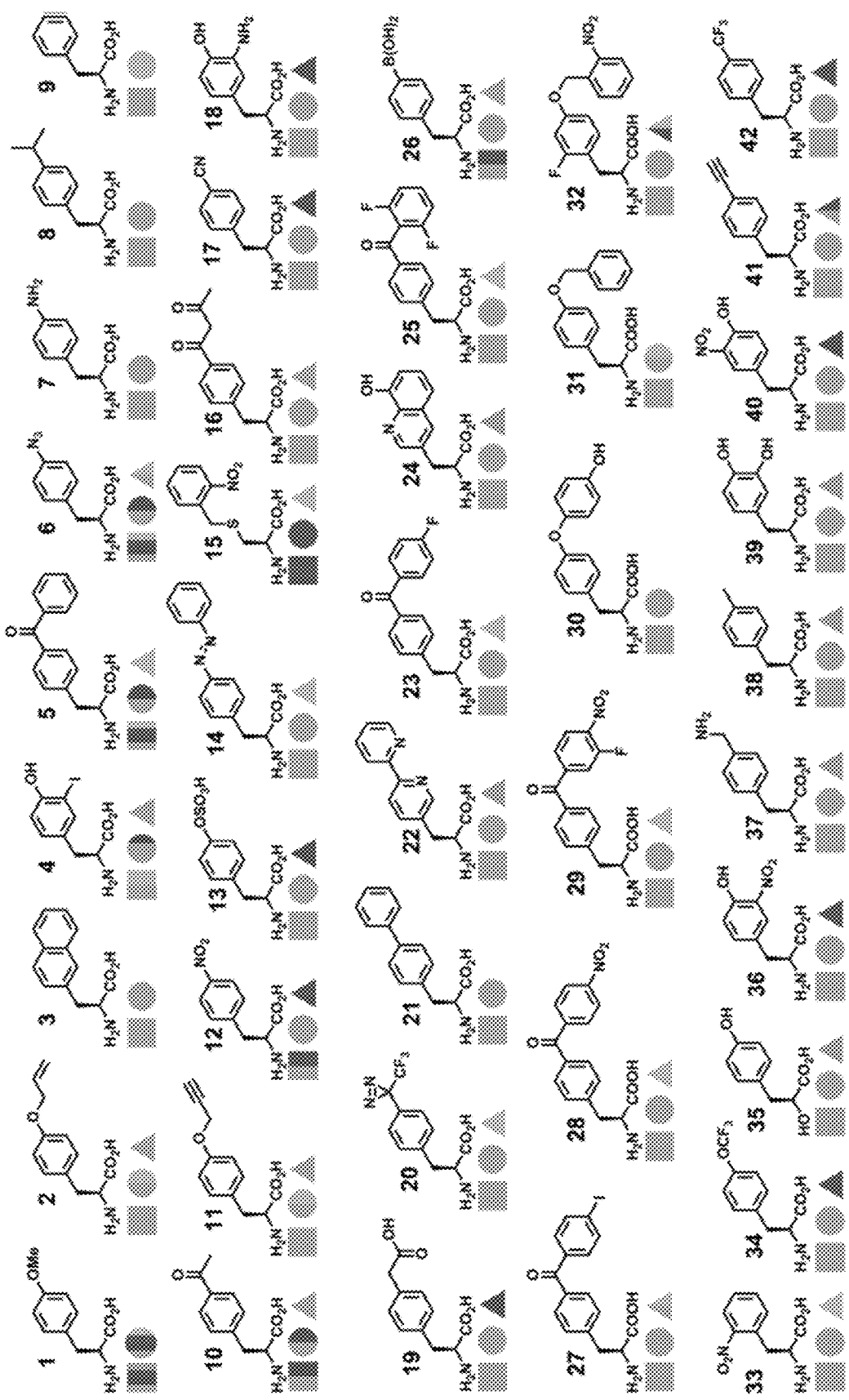
FIG. 3A-FIG. 3D illustrate exemplary unnatural amino acids. These unnatural amino acids (UAAs) have been genetically encoded in proteins (FIG. 3A—UAA #1-42.
Figure 3B:
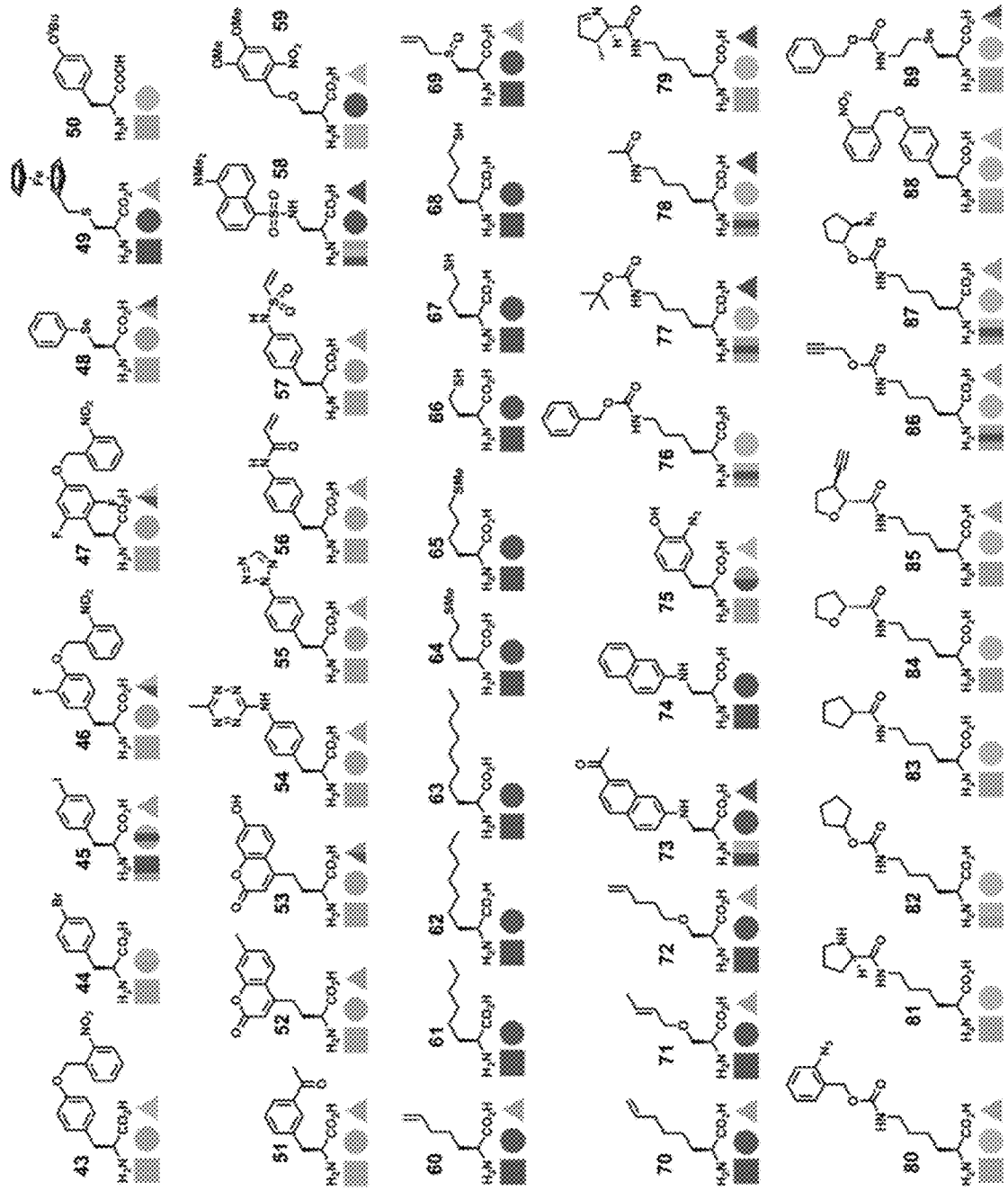
Figure 3C:
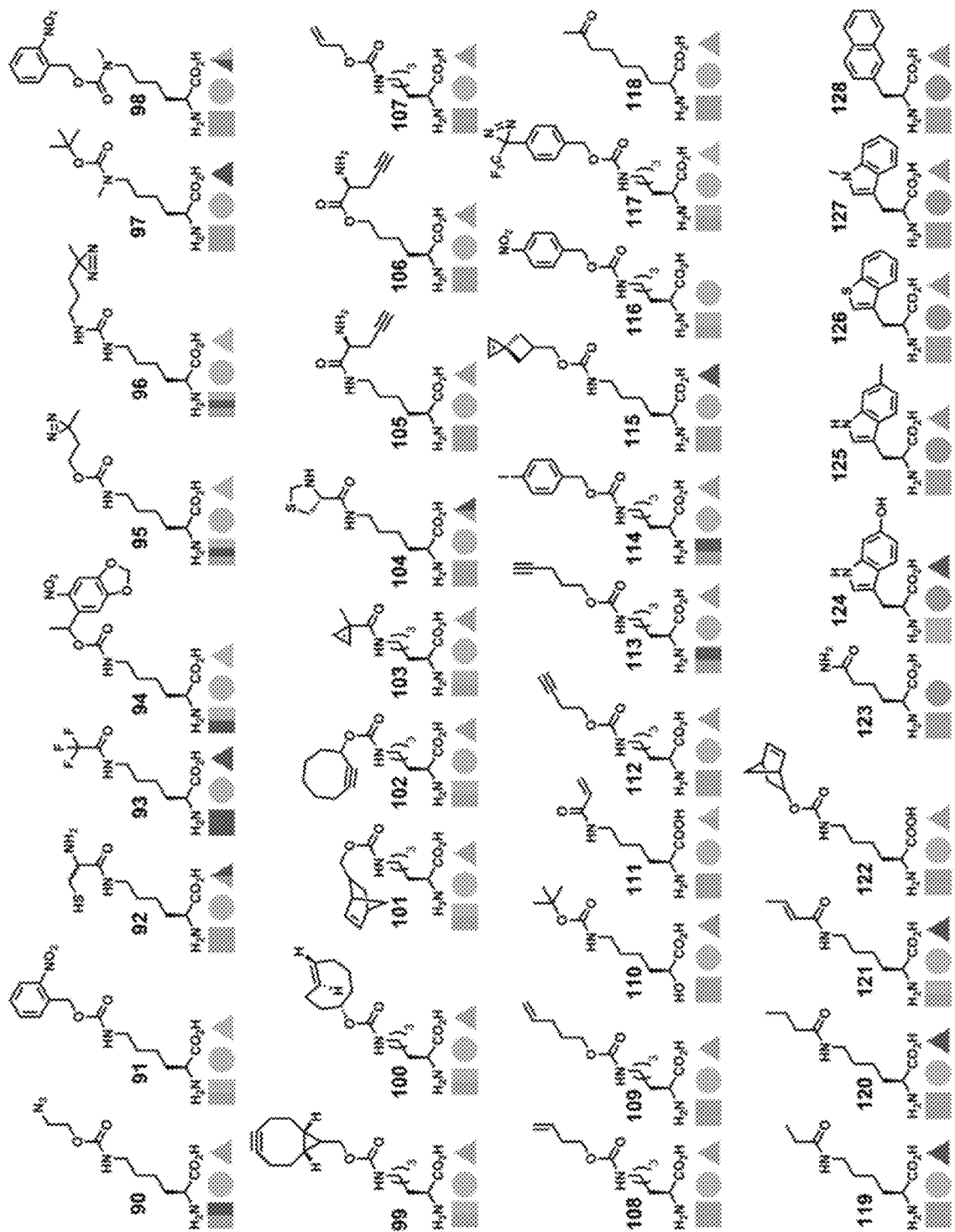
Figure 3D:
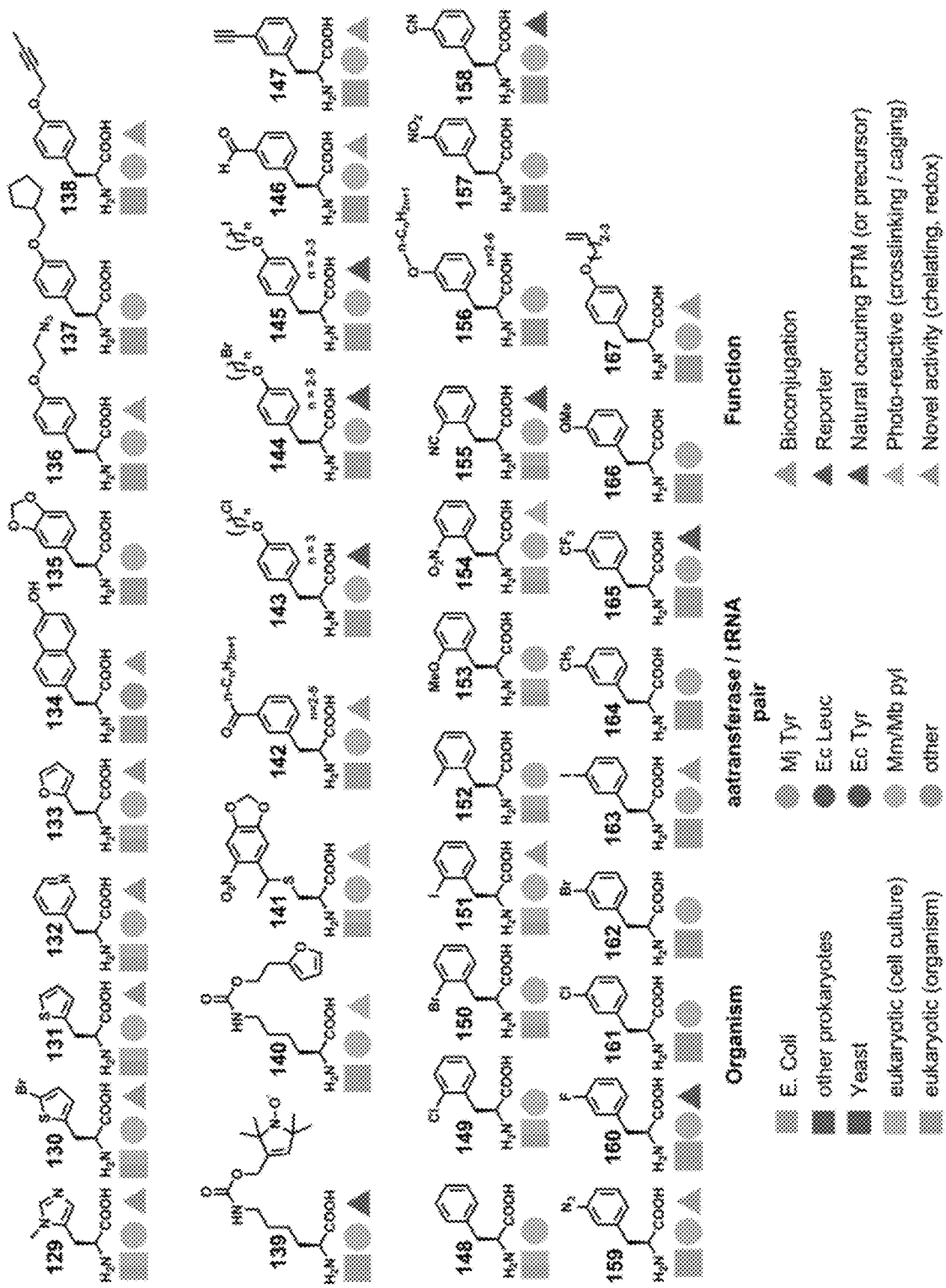

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biocheim Biophys Aceta 1844(6): 1059-4070 (2014). In some instances, the unnatural amino acid comprises an unnatural amino acid illustrated in FIG. 2 (e.g., FIG. 2A and FIG. 2B).

In some embodiments, the unnatural amino acid comprises an unnatural amino acid illustrated in FIG. 3A-FIG. 3D (adopted from Table 1 of Dumas et al., *Chemical Science* 2015, 6, 50-69).

In some embodiments, an unnatural amino acid incorporated into an IL-15 polypeptide is disclosed in U.S. Pat. Nos. 9,840,493; 9,682,934; US 2017/0260137; U.S. Pat. No. 9,938,516; or US 2018/0086734. Exemplary UAAs that can be incorporated by such synthetases include para-methyl-azido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into cytokines in-vivo. In some embodiments, such UAAs are incorporated into cytokines in a cell-free system.

Conjugating Moieties

In certain embodiments, disclosed herein are conjugating moieties that are bound to one or more modified IL-15 polypeptide described supra. In some embodiments, the conjugating moiety is a molecule that perturbs the interaction of IL-15 with its receptor. In some embodiments, the conjugating moiety is any molecule that when bond to IL-15, enables IL-15 conjugate to modulate an immune response. In some embodiments, the conjugating moiety is bound to the IL-15 through a covalent bond. In some instances, an IL-15 described herein is attached to a conjugating moiety with a triazole group. In some instances, an IL-15 described herein is attached to a conjugating moiety with a dihydropyridazine or pyridazine group. In some instances, the conjugating moiety comprises a water-soluble polymer. In other instances, the conjugating moiety comprises a protein or a binding fragment thereof. In additional instances, the conjugating moiety comprises a peptide. In additional instances, the conjugating moiety comprises a nucleic acid. In additional instances, the conjugating moiety comprises a small molecule. In additional instances, the conjugating moiety comprises a bioconjugate (e.g., a TLR agonist such as a TLR1, TLR2, TLR3, TLR4, TLR5, TLR6, TLR7, TLR8, or TLR9 agonist; or a synthetic ligand such as Pam3Cys, CFA, MALP2, Pam2Cys, FSL-1, Hib-OMPC, Poly I:C, poly A:U, AGP, MPL A, RC-529, MDF2β, CFA, or Flagellin). In some cases, the conjugating moiety increases serum half-life, and/or improves stability. In some cases, the conjugating moiety reduces cytokine interaction with one or more cytokine receptor domains or subunits. In additional cases, the conjugating moiety blocks IL-15 interaction with one or more IL-15 domains or subunits with its cognate receptor(s). In some embodiments, IL-15 conjugates described herein comprise multiple conjugating moieties. In some embodiments, a conjugating moiety is attached to an unnatural or natural amino acid in the IL-15 polypeptide. In some embodiments, an IL-15 conjugate comprises a conjugating moiety attached to a natural amino acid. In some embodiments, an IL-15 conjugate is attached to an unnatural amino acid in the cytokine peptide. In some embodiments, a conjugating moiety is attached to the N or C terminal amino acid of the IL-15 polypeptide. Various combinations sites are disclosed herein, for example, a first conjugating moiety is attached to an unnatural or natural amino acid in the IL-15 polypeptide, and a second conjugating moiety is attached to the N or C terminal amino acid of the IL-15 polypeptide. In some embodiments, a single conjugating moiety is attached to multiple residues of the IL-15 polypeptide (e.g. a staple). In some embodiments, a conjugating moiety is attached to both the N and C terminal amino acids of the IL-15 polypeptide.

Water-Soluble Polymers

In some embodiments, a conjugating moiety descried herein is a water-soluble polymer. In some embodiments, the water-soluble polymer is a nonpeptidic, nontoxic, and biocompatible. As used herein, a substance is considered biocompatible if the beneficial effects associated with use of the substance alone or with another substance (e.g., an active agent such as an IL-15 moiety) in connection with living tissues (e.g., administration to a patient) outweighs any deleterious effects as evaluated by a clinician, e.g., a physician. In some embodiments, a water-soluble polymer is further non-immunogenic. In some embodiments, a substance is considered non-immunogenic if the intended use of the substance in vivo does not produce an undesired immune response (e.g., the formation of antibodies) or, if an immune response is produced, that such a response is not deemed clinically significant or important as evaluated by a clinician, e.g., a physician, a toxicologist, or a clinical development specialist.

In some embodiments, the water-soluble polymer is characterized as having from about 2 to about 300 termini. Exemplary water soluble polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazolines ("POZ") (which are described in WO 2008/106186), poly(N-acryloylmorpholine), and combinations of any of the foregoing.

In some embodiments, the water-soluble polymer is not limited to a particular structure. In some embodiments, the water-soluble polymer is linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

In some embodiments, the weight-average molecular weight of the water-soluble polymer in the IL-21 conjugate is from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

PEGs will typically comprise a number of ($OCH_2CH_2$) monomers [or ($CH_2CH_2O$) monomers, depending on how the PEG is defined]. As used herein, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In some embodiments, the water-soluble polymer is an end-capped polymer, that is, a polymer having at least one terminus capped with a relatively inert group, such as a lower $C_{1-6}$ alkoxy group, or a hydroxyl group. When the polymer is PEG, for example, a methoxy-PEG (commonly referred to as mPEG) may be used, which is a linear form of PEG wherein one terminus of the polymer is a methoxy (—$OCH_3$) group, while the other terminus is a hydroxyl or other functional group that can be optionally chemically modified.

In some embodiments, exemplary water-soluble polymers include, but are not limited to, linear or branched discrete PEG (dPEG) from Quanta Biodesign, Ltd; linear, branched, or forked PEGs from Nektar Therapeutics; linear, branched, or Y-shaped PEG derivatives from JenKem Technology.

In some embodiments, IL-15 polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazolines ("POZ"), poly(N-acryloylmorpholine), and a combination thereof. In some embodiments, the IL-15 polypeptide is conjugated to PEG (e.g., PEGylated). In some embodiments, the IL-15 polypeptide is conjugated to PPG. In some embodiments, the IL-15 polypeptide is conjugated to POZ. In some instances, the IL-15 polypeptide is conjugated to PVP.

In some instances, a water-soluble polymer comprises a polyglycerol (PG). In some cases, the polyglycerol is a hyperbranched PG (HPG) (e.g., as described by Imran, et al. "Influence of architecture of high molecular weight linear and branched polyglycerols on their biocompatibility and biodistribution," *Biomaterials* 33:9135-9147 (2012)). In other cases, the polyglycerol is a linear PG (LPG). In additional cases, the polyglycerol is a midfunctional PG, a linear-block-hyperbranched PG (e.g., as described by Wurm et. Al., "Squaric acid mediated synthesis and biological activity of a library of linear and hyperbranched poly(glycerol)-protein conjugates," *Biomacromolecules* 13:1161-1171 (2012)), or a side-chain functional PG (e.g., as described by Li, et. al., "Synthesis of linear polyether polyol derivatives as new materials for bioconjugation," *Bioconjugate Chem.* 20:780-789 (2009)).

In some instances, an IL-15 polypeptide described herein is conjugated to a PG, e.g., a HPG, a LPG, a midfunctional PG, a linear-block-hyperbranched PG, or a side-chain functional PG.

In some embodiments, a water-soluble polymer is a degradable synthetic PEG alternative. Exemplary degradable synthetic PEG alternatives include, but are not limited to, poly[oligo(ethylene glycol)methyl methacrylate] (POEGMA); backbone modified PEG derivatives generated by polymerization of telechelic, or di-end-functionalized PEG-based macromonomers; PEG derivatives comprising comonomers comprising degradable linkage such as poly[(ethylene oxie)-co-(methylene ethylene oxide)][P(EO-co-MEO)], cyclic ketene acetals such as 5,6-benzo-2-methylene-1,3-dioxepane (BMDO), 2-methylene-1,3-dioxepane (MDO), and 2-methylene-4-phenyl-1,3-dioxolane (MPDL) copolymerized with OEGMA; or poly-(ε-caprolactone)-graft-poly(ethylene oxide) (PCL-g-PEO).

In some instances, an IL-15 polypeptide described herein is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO.

In some embodiments, a water-soluble polymer comprises a poly(zwitterions). Exemplary poly(zwitterions) include, but are not limited to, poly(sulfobetaine methacrylate) (PSBMA), poly(carboxybetaine methacrylate) (PCBMA), and poly(2-methyacryloyloxyethyl phosphorylcholine) (PMPC). In some instances, an IL-15 polypeptide is conjugated to a poly(zwitterion) such as PSBMA, PCBMA, or PMPC.

In some embodiments, a water-soluble polymer comprises a polycarbonate. Exemplary polycarbones include, but are not limited to, pentafluorophenyl 5-methyl-2-oxo-1,3-dioxane-5-carboxylate (MTC-OC$_6$F$_5$). In some instances, an IL-15 polypeptide described herein is conjugated to a polycarbonate such as MTC-OC$_6$F$_5$.

In some embodiments, a water-soluble polymer comprises a polymer hybrid, such as for example, a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some instances, an IL-15 polypeptide described herein is conjugated to a polymer hybrid such as a polycarbonate/PEG polymer hybrid, a peptide/protein-polymer conjugate, or a hydroxylcontaining and/or zwitterionic derivatized polymer (e.g., a hydroxyl-containing and/or zwitterionic derivatized PEG polymer).

In some embodiments, a water-soluble polymer comprises a polysaccharide. Exemplary polysaccharides include, but are not limited to, dextran, polysialic acid (PSA), hyaluronic acid (HA), amylose, heparin, heparan sulfate (HS), dextrin, or hydroxyethyl-starch (HES). In some embodiments, an IL-15 polypeptide is conjugated to dextran. In some embodiments, an IL-15 polypeptide is conjugated to PSA. In some embodiments, an IL-15 polypeptide is conjugated to HA. In some embodiments, an IL-15 polypeptide is conjugated to amylose. In some embodiments, an IL-15 polypeptide is conjugated to heparin. In some embodiments, an IL-15 polypeptide is conjugated to HS. In some embodiments, an IL-15 polypeptide is conjugated to dextrin. In some embodiments, an IL-15 polypeptide is conjugated to HES.

In some embodiments, a water-soluble polymer comprises a glycan. Exemplary classes of glycans include N-linked glycans, O-linked glycans, glycolipids, O-GlcNAc, and glycosaminoglycans. In some embodiments, an IL-15 polypeptide is conjugated to a glycan. In some embodiments, an IL-15 polypeptide is conjugated to N-linked glycans. In some embodiments, an IL-15 polypeptide is conjugated to O-linked glycans. In some embodiments, an IL-15 polypeptide is conjugated to glycolipids. In some embodiments, an IL-15 polypeptide is conjugated to O-GlcNAc. In some embodiments, an IL-15 polypeptide is conjugated to glycosaminoglycans.

In some embodiments, a water-soluble polymer comprises a polyoxazoline polymer. A polyoxazoline polymer is a linear synthetic polymer, and similar to PEG, comprises a low polydispersity. In some embodiments, a polyoxazoline polymer is a polydispersed polyoxazoline polymer, characterized with an average molecule weight. In some embodiments, the average molecule weight of a polyoxazoline polymer includes, for example, 1000, 1500, 2000, 2500, 3000, 3500, 4000, 4500, 5000, 5500, 6000, 6500, 7000, 7500, 8000, 10,000, 12,000, 20,000, 35,000, 40,000, 50,000, 60,000, 100,000, 200,000, 300,000, 400,000, or 500,000 Da. In some embodiments, a polyoxazoline polymer comprises poly(2-methyl 2-oxazoline) (PMOZ), poly(2-ethyl 2-oxazoline) (PEOZ), or poly(2-propyl 2-oxazoline) (PPOZ). In some embodiments, an IL-15 polypeptide is conjugated to a polyoxazoline polymer. In some embodiments, an IL-15 polypeptide is conjugated to PMOZ. In some embodiments, an IL-15 polypeptide is conjugated to PEOZ. In some embodiments, an IL-15 polypeptide is conjugated to PPOZ.

In some embodiments, a water-soluble polymer comprises a polyacrylic acid polymer. In some embodiments, an IL-15 polypeptide is conjugated to a polyacrylic acid polymer.

In some embodiments, a water-soluble polymer comprises polyamine. Polyamine is an organic polymer comprising two or more primary amino groups. In some embodiments, a polyamine includes a branched polyamine, a linear polyamine, or cyclic polyamine. In some embodiments, a polyamine is a low-molecular-weight linear polyamine. Exemplary polyamines include putrescine, cadaverine, spermidine, spermine, ethylene diamine, 1,3-diaminopropane, hexamethylenediamine, tetraethylmethylenediamine, and piperazine. In some embodiments, an IL-15 polypeptide is conjugated to polyamine. In some embodiments, an IL-15 polypeptide is conjugated to putrescine, cadaverine, spermidine, spermine, ethylene diamine, 1,3-diaminopropane, hexamethylenediamine, tetraethylmethylenediamine, or piperazine.

Lipids

In some embodiments, a conjugating moiety descried herein is a lipid. In some instances, the lipid is a fatty acid. In some cases, the fatty acid is a saturated fatty acid. In other cases, the fatty acid is an unsaturated fatty acid. Exemplary fatty acids include, but are not limited to, fatty acids comprising from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the lipid binds to one or more serum proteins, thereby increasing serum stability and/or serum half-life.

In some embodiments, the lipid is conjugated to an IL-15 polypeptide described herein. In some instances, the lipid is a fatty acid, e.g., a saturated fatty acid or an unsaturated fatty acid. In some cases, the fatty acid is from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the fatty acid comprises about 6, 7, 8, 9, 10, 11, 12, 13, 14, 15, 16, 17, 18, 19, 20, 21, 22, 23, 24, 25, or 26 carbon atoms in length. In some cases, the fatty acid comprises caproic acid (hexanoic acid), enanthic acid (heptanoic acid), caprylic acid (octanoic acid), pelargonic acid (nonanoic acid), capric acid (decanoic acid), undecylic acid (undecanoic acid), lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric acid (tetracosanoic acid), pentacosylic acid (pentacosanoic acid), or cerotic acid (hexacosanoic acid).

In some embodiments, the IL-15 lipid conjugate enhances serum stability and/or serum half-life.

Proteins

In some embodiments, a conjugating moiety described herein is a protein or a binding fragment thereof. Exemplary proteins include albumin, transferrin, or transthyretin. In some embodiments, the protein or a binding fragment thereof comprises an antibody, or its binding fragments thereof. In some embodiments, an IL-15 conjugate comprises a protein or a binding fragment thereof. In some embodiments, an IL-15 conjugate comprising a protein or a binding fragment thereof has an increased serum half-life, and/or stability. In some embodiments, an IL-15 conjugate comprising a protein or a binding fragment thereof has a reduced IL-15 interaction with one or more IL-15R/IL-2R subunits. In additional cases, the protein or a binding fragment thereof blocks IL-15 interaction with one or more IL-15R/IL-2R subunits.

In some embodiments, the conjugating moiety is albumin. Albumin is a family of water-soluble globular proteins. It is commonly found in blood plasma, comprising about 55-60% of all plasma proteins. Human serum albumin (HSA) is a 585 amino acid polypeptide in which the tertiary structure is divided into three domains, domain I (amino acid residues 1-195), domain II (amino acid residues 196-383), and domain III (amino acid residues 384-585). Each domain further comprises a binding site, which can interact either reversibly or irreversibly with endogenous ligands such as long- and medium-chain fatty acids, bilirubin, or hemin, or exogenous compounds such as heterocyclic or aromatic compounds.

In some embodiments, an IL-15 polypeptide is conjugated to albumin. In some embodiments, the IL-15 polypeptide is conjugated to human serum albumin (HSA). In additional cases, the IL-15 polypeptide is conjugated to a functional fragment of albumin.

In some embodiments, the conjugating moiety is transferrin. Transferrin is a 679 amino acid polypeptide that is about 80 kDa in size and comprises two $Fe^{3+}$ binding sites with one at the N-terminal domain and the other at the C-terminal domain. In some embodiments, human transferrin has a half-life of about 7-12 days.

In some embodiments, an IL-15 polypeptide is conjugated to transferrin. In some embodiments, the IL-15 polypeptide is conjugated to human transferrin. In additional cases, the IL-15 polypeptide is conjugated to a functional fragment of transferrin.

In some embodiments, the conjugating moiety is transthyretin (TTR). Transthyretin is a transport protein located in the serum and cerebrospinal fluid which transports the thyroid hormone thyroxine ($T_4$) and retinol-binding protein bound to retinol.

In some embodiments, an IL-15 polypeptide is conjugated to transthyretin (via one of its termini or via an internal hinge region). In some embodiments, the IL-15 polypeptide is conjugated to a functional fragment of transthyretin.

In some embodiments, the conjugating moiety is an antibody, or its binding fragments thereof. In some embodiments, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, the conjugating moiety comprises a scFv, bis-scFv, (scFv)$_2$, dsFv, or sdAb. In some cases, the conjugating moiety comprises a scFv. In some cases, the conjugating moiety comprises a bis-scFv. In some cases, the conjugating moiety comprises a (scFv)$_2$. In some cases, the conjugating moiety comprises a dsFv. In some cases, the conjugating moiety comprises a sdAb.

In some embodiments, the conjugating moiety comprises an Fc portion of an antibody, e.g., of IgG, IgA, IgM, IgE, or IgD. In some embodiments, the moiety comprises an Fc portion of IgG (e.g., IgG$_1$, IgG$_3$, or IgG$_4$).

In some embodiments, an IL-15 polypeptide is conjugated to an antibody, or its binding fragments thereof. In some embodiments, the IL-15 polypeptide is conjugated to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-15 polypeptide is conjugated to an Fc portion of an antibody. In additional cases, the IL-15 polypeptide is conjugated to an Fc portion of IgG (e.g., IgG$_1$, IgG$_3$, or IgG$_4$).

In some embodiments, an IL-15 polypeptide is conjugated to a water-soluble polymer (e.g., PEG) and an antibody or binding fragment thereof. In some cases, the antibody or binding fragments thereof comprises a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In some cases, the antibody or binding fragments thereof comprises a scFv, bis-scFv, (scFv)$_2$, dsFv, or sdAb. In some cases, the antibody or binding fragments thereof comprises a scFv. In some cases, the antibody or binding fragment thereof guides the IL-15 conjugate to a target cell of interest and the water-soluble polymer enhances stability and/or serum half-life.

In some instances, one or more IL-15 polypeptide—water-soluble polymer (e.g., PEG) conjugates are further bound to an antibody or binding fragments thereof. In some instances, the ratio of the IL-15 conjugate to the antibody is about 1:1, 2:1, 3:1, 4:1, 5:1, 6:1, 7:1, 8:1, 9:1, 10:1, 11:1, or 12:1. In some cases, the ratio of the IL-15 conjugate to the antibody is about 1:1. In other cases, the ratio of the IL-15 conjugate to the antibody is about 2:1, 3:1, or 4:1. In additional cases, the ratio of the IL-15 conjugate to the antibody is about 6:1 or higher.

In some embodiments, the one or more IL-15 polypeptide—water-soluble polymer (e.g., PEG) conjugates are directly bound to the antibody or binding fragments thereof. In other instances, the IL-15 conjugate is indirectly bound to the antibody or binding fragments thereof with a linker. Exemplary linkers include homobifunctional linkers, heterobifunctional linkers, maleimide-based linkers, zero-trace linkers, self-immolative linkers, spacers, and the like.

In some embodiments, the antibody or binding fragments thereof is bound either directly or indirectly to the IL-15 polypeptide portion of the IL-15 polypeptide—water-soluble polymer (e.g., PEG) conjugate. In such cases, the conjugation site of the antibody to the IL-15 polypeptide is at a site that will not impede binding of the IL-15 polypeptide with the IL-15R. In additional cases, the conjugation site of the antibody to the IL-15 polypeptide is at a site that partially blocks binding of the IL-15 polypeptide with the IL-15R. In other embodiments, the antibody or binding fragments thereof is bound either directly or indirectly to the water-soluble polymer portion of the IL-15 polypeptide—water-soluble polymer (e.g., PEG) conjugate.

Peptides

In some embodiments, a conjugating moiety descried herein is a peptide. In some embodiments, the peptide is a non-structured peptide. In some embodiments, a cytokine (e.g., an interleukin, IFN, or TNF) polypeptide is conjugated to a peptide. In some embodiments, the IL-15 conjugate comprising a peptide has an increased serum half-life, and/or stability. In some embodiments, the IL-15 conjugate comprising a peptide has a reduced IL-15 interaction with one or more IL-15R subunits. In additional cases, the peptide blocks IL-15 interaction with one or more IL-15R subunits.

In some embodiments, the conjugating moiety is a XTEN™ peptide (Amunix Operating Inc.) and the modification is referred to as XTENylation. XTENylation is the genetic fusion of a nucleic acid encoding a polypeptide of interest with a nucleic acid encoding a XTEN™ peptide (Amunix Operating Inc.), a long unstructured hydrophilic peptide comprising different percentage of six amino acids: Ala, Glu, Gly, Ser, and Thr. In some embodiments, a XTEN™ peptide is selected based on properties such as expression, genetic stability, solubility, aggregation resistance, enhanced half-life, increased potency, and/or increased in vitro activity in combination with a polypeptide of interest. In some embodiments, a cytokine (e.g., an interleukin, IFN, or TNF) polypeptide is conjugated to a XTEN peptide. In some embodiments, an IL-15 polypeptide is conjugated to a XTEN peptide.

In some embodiments, the conjugating moiety is a glycine-rich homoamino acid polymer (HAP) and the modification is referred to as HAPylation. HAPylation is the genetic fusion of a nucleic acid encoding a polypeptide of interest with a nucleic acid encoding a glycine-rich homoamino acid polymer (HAP). In some embodiments, the HAP polymer comprises a (Gly$_4$Ser)$_n$ repeat motif and sometimes are about 50, 100, 150, 200, 250, 300, or more residues in length. In some embodiments, a cytokine (e.g., an interleukin, IFN, or TNF) polypeptide is conjugated to HAP. In some embodiments, an IL-15 polypeptide is conjugated to HAP.

In some embodiments, the conjugating moiety is a PAS polypeptide and the modification is referred to as PASylation. PASylation is the genetic fusion of a nucleic acid encoding a polypeptide of interest with a nucleic acid encoding a PAS polypeptide. A PAS polypeptide is a hydrophilic uncharged polypeptide consisting of Pro, Ala and Ser residues. In some embodiments, the length of a PAS polypeptide is at least about 100, 200, 300, 400, 500, or 600 amino acids. In some embodiments, a cytokine (e.g., an interleukin, IFN, or TNF) polypeptide is conjugated to a PAS polypeptide. In some embodiments, an IL-15 polypeptide is conjugated to a PAS polypeptide.

In some embodiments, the conjugating moiety is an elastin-like polypeptide (ELP) and the modification is referred to as ELPylation. ELPylation is the genetic fusion of a nucleic acid encoding a polypeptide of interest with a nucleic acid encoding an elastin-like polypeptide (ELPs). An ELP comprises a VPGxG repeat motif in which x is any amino acid except proline. In some embodiments, a cytokine (e.g., an interleukin, IFN, or TNF) polypeptide is conjugated to ELP. In some embodiments, an IL-15 polypeptide is conjugated to ELP.

In some embodiments, the conjugating moiety is a CTP peptide. A CTP peptide comprises a 31 amino acid residue peptide FQSSSS*KAPPPS*LPSPS*RLPGPS*DTPILPQ in which the S* denotes 0-glycosylation sites (OPKO). In some embodiments, a CTP peptide is genetically fused to a cytokine polypeptide (e.g., an IL-15 polypeptide). In some embodiments, a cytokine polypeptide (e.g., an IL-15 polypeptide) is conjugated to a CTP peptide.

In some embodiments, a cytokine (e.g., an IL-15 polypeptide) is modified by glutamylation. Glutamylation (or polyglutamylation) is a reversible posttranslational modification of glutamate, in which the γ-carboxy group of glutamate forms a peptide-like bond with the amino group of a free glutamate in which the α-carboxy group extends into a polyglutamate chain.

In some embodiments, an IL-15 polypeptide is modified by a gelatin-like protein (GLK) polymer. In some embodiments, the GLK polymer comprises multiple repeats of Gly-Xaa-Yaa wherein Xaa and Yaa primarily comprise proline and 4-hydroxyproline, respectively. In some embodiments, the GLK polymer further comprises amino acid residues Pro, Gly, Glu, Qln, Asn, Ser, and Lys. In some embodiments, the length of the GLK polymer is about 20, 30, 40, 50, 60, 70, 80, 90, 100, 110, 120, 150 residues or longer.

Additional Conjugating Moieties

In some embodiments, the conjugating moiety comprises an extracellular biomarker. In some embodiments, the extracellular biomarker is a tumor antigen. In some embodiments, exemplary extracellular biomarker comprises CD19, PSMA, B7-H3, B7-H6, CD70, CEA, CSPG4, EGFRvIII, EphA3, EpCAM, EGFR, ErbB2 (HER2), FAP, FRα, GD2, GD3, Lewis-Y, mesothelin, Muc1, Muc 16, ROR1, TAG72, VEGFR2, CD11, Gr-1, CD204, CD16, CD49b, CD3, CD4, CD8, and B220. In some embodiments, the conjugating moiety is bond or conjugated to the IL-15. In some embodiments, the conjugating moiety is genetically fused, for example, at the N-terminus or the C-terminus, of the IL-15.

In some embodiments, the conjugating moiety comprises a molecule from a post-translational modification. In some embodiments, examples of post-translational modification include myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation. In some embodiments, the IL-15 is modified by a post-translational modification such as myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation.

Linkers

In some embodiments, useful functional reactive groups for conjugating or binding a conjugating moiety to an IL-15 polypeptide described herein include, for example, zero or higher-order linkers. In some instances, an unnatural amino acid incorporated into an interleukin described herein comprises a functional reactive group. In some instances, a linker comprises a functional reactive group that reacts with an unnatural amino acid incorporated into an interleukin described herein. In some instances, a conjugating moiety comprises a functional reactive group that reacts with an unnatural amino acid incorporated into an interleukin described herein. In some instances, a conjugating moiety comprises a functional reactive group that reacts with a linker (optionally pre-attached to a cytokine peptide) described herein. In some embodiments, a linker comprises a reactive group that reacts with a natural amino acid in an IL-15 polypeptide described herein. In some cases, higher-order linkers comprise bifunctional linkers, such as homo-bifunctional linkers or heterobifunctional linkers. Exemplary homobifuctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bis-maleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the bifunctional linker comprises a heterobifunctional linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl) butyrate (sulfo-sMPB), N-(γ-maleimidobutyryloxy) succinimide ester (GMBs), N-(γ-maleimidobutyryloxy) sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino) methyl)cyclohexane-1-carbonyl)amino) hexanoate (sI-ACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M2C2H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido) ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino) hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1, 3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the reactive functional group comprises a nucleophilic group that is reactive to an electrophilic group present on a binding moiety (e.g., on a conjugating moiety or on IL-15). Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide. In some embodiments, an unnatural amino acid incorporated into an interleukin described herein comprises an electrophilic group.

In some embodiments, the linker is a cleavable linker. In some embodiments, the cleavable linker is a dipeptide linker. In some embodiments, the dipeptide linker is valine-citrulline (Val-Cit), phenylalanine-lysine (Phe-Lys), valine-alanine (Val-Ala) and valine-lysine (Val-Lys). In some embodiments, the dipeptide linker is valine-citrulline.

In some embodiments, the linker is a peptide linker comprising, e.g., at least 2, 3, 4, 5, 6, 7, 8, 9, 10, 11, 12, 15, 20, 25, 30, 35, 40, 45, 50, or more amino acids. In some instances, the peptide linker comprises at most 2, 3, 4, 5, 6, 7, 8, 9, 10, 11, 12, 15, 20, 25, 30, 35, 40, 45, 50, or less amino acids. In additional cases, the peptide linker comprises about 2, 3, 4, 5, 6, 7, 8, 9, 10, 11, 12, 15, 20, 25, 30, 35, 40, 45, or 50 amino acids.

In some embodiments, the linker comprises a self-immolative linker moiety. In some embodiments, the self-immolative linker moiety comprises p-aminobenzyl alcohol (PAB), p-aminobenzyoxycarbonyl (PABC), or derivatives or analogs thereof. In some embodiments, the linker comprises a dipeptide linker moiety and a self-immolative linker moiety. In some embodiments, the self-immolative linker moiety is such as described in U.S. Pat. No. 9,089,614 and WIPO Application No. WO2015038426.

In some embodiments, the cleavable linker is glucuronide. In some embodiments, the cleavable linker is an acid-cleavable linker. In some embodiments, the acid-cleavable linker is hydrazine. In some embodiments, the cleavable linker is a reducible linker.

In some embodiments, the linker comprises a maleimide group. In some instances, the maleimide group is also referred to as a maleimide spacer. In some instances, the maleimide group further comprises a caproic acid, forming maleimidocaproyl (mc). In some cases, the linker comprises maleimidocaproyl (mc). In some cases, linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," Nat. Biotechnol. 32(10): 1059-1062 (2014). In some instances, the linker comprises a self-stabilizing maleimide. In some instances, the linker is a self-stabilizing maleimide.

Conjugation Chemistry

Various conjugation reactions are used to conjugate linkers, conjugation moieties, and unnatural amino acids incorporated into IL-15 polypeptides described herein. Such conjugation reactions are often compatible with aqueous conditions, such as "bioorthogonal" reactions. In some embodiments, conjugation reactions are mediated by chemical reagents such as catalysts, light, or reactive chemical groups found on linkers, conjugation moieties, or unnatural amino acids. In some embodiments, conjugation reactions are mediated by enzymes. In some embodiments, a conjugation reaction used herein is described in Gong, Y., Pan, L. Tett. Lett. 2015, 56, 2123. In some embodiments, a conjugation reaction used herein is described in Chen, X.; Wu. Y-W. Org. Biomol. Chem. 2016, 14, 5417.

In some embodiments described herein, a conjugation reaction comprises reaction of a ketone or aldehyde with a nucleophile. In some embodiments, a conjugation reaction comprises reaction of a ketone with an aminoxy group to form an oxime. In some embodiments, a conjugation reaction comprises reaction of a ketone with an aryl or heteroaryl amine group to form an imine. In some embodiments, a conjugation reaction comprises reaction of an aldehyde with an aryl or heteroaryl amine group to form an imine. In some embodiments, a conjugation reaction described herein results in an IL-15 polypeptide comprising a linker or conjugation moiety attached via an oxime. In some embodiments, a conjugation reaction comprises a Pictet-Spengler reaction of an aldehyde or ketone with a tryptamine nucleophile. In some embodiments, a conjugation reaction comprises a hydrazino-Pictet-Spengler reaction. In some embodiments, a conjugation reaction comprises a Pictet-Spengler ligation.

In some embodiments described herein, a conjugation reaction described herein comprises reaction of an azide and a phosphine (Staudinger ligation). In some embodiments, the phosphine is an aryl phosphine. In some embodiments, the aryl phosphine comprises an ortho ester group. In some embodiments, the phosphine comprises the structure methyl 2-(diphenylphosphaneyl)benzoate. In some embodiments, a conjugation reaction described herein results in IL-15 polypeptide comprising a linker or conjugation moiety attached via an arylamide. In some embodiments, a conjugation reaction described herein results in an IL-15 polypeptide comprising a linker or conjugation moiety attached via an amide.

In some embodiments described herein, a conjugation reaction described herein comprises a 1,3-dipolar cycloaddition reaction. In some embodiments, the 1,3-dipolar cycloaddition reaction comprises reaction of an azide and a phosphine ("Click" reaction). In some embodiments, the conjugation reaction is catalyzed by copper. In some embodiments, a conjugation reaction described herein results in an IL-15 polypeptide comprising a linker or conjugation moiety attached via a triazole. In some embodiments, a conjugation reaction described herein comprises reaction of an azide with a strained olefin. In some embodiments, a conjugation reaction described herein comprises reaction of an azide with a strained alkyne. In some embodiments, a conjugation reaction described herein comprises reaction of an azide with a cycloalkyne, for example, OCT, DIFO, DIFBO, DIBO, BARAC, TMTH, or other strained cycloalkyne, the structures of which are shown in Gong, Y., Pan, L. Tett. Lett. 2015, 56, 2123. In some embodiments, a 1,3-dipolar cycloaddition reaction is catalyzed by light ("photoclick"). In some embodiments, a conjugation reaction described herein comprises reaction of a terminal allyl group with a tetrazole and light. In some embodiments, a conjugation reaction described herein comprises reaction of a terminal alkynyl group with a tetrazole and light. In some embodiments, a conjugation reaction described herein comprises reaction of an O-allyl amino acid with a tetrazine and light. In some embodiments, a conjugation reaction described herein comprises reaction of 0-allyl tyrosine with a tetrazine and light.

In some embodiments described herein, a conjugation reaction described herein comprises an inverse-electron demand cycloaddition reaction comprising a diene and a dienophile. In some embodiments, the diene comprises a tetrazine. In some embodiments, the dienophile comprises an alkene. In some embodiments, the dienophile comprises an alkyne. In some embodiments, the alkyne is a strained alkyne. In some embodiments, the alkene is a strained diene. In some embodiments, the alkyne is a trans-cyclooctyne. In some embodiments, the alkyne is a cyclooctene. In some embodiments, the alkene is a cyclopropene. In some embodiments, the alkene is a fluorocyclopropene. In some embodiments, a conjugation reaction described herein results in the formation of an IL-15 polypeptide attached to a linker or conjugation moiety via a 6-membered ring heterocycle comprising two nitrogen atoms in the ring.

In some embodiments described herein, a conjugation reaction described herein comprises an olefin metathesis reaction. In some embodiments, a conjugation reaction described herein comprises reaction of an alkene and an alkyne with a ruthenium catalyst. In some embodiments, a conjugation reaction described herein comprises reaction of two alkenes with a ruthenium catalyst. In some embodiments, a conjugation reaction described herein comprises reaction of two alkynes with a ruthenium catalyst. In some embodiments, a conjugation reaction described herein comprises reaction of an alkene or alkyne with a ruthenium catalyst and an amino acid comprising an allyl group. In some embodiments, a conjugation reaction described herein comprises reaction of an alkene or alkyne with a ruthenium catalyst and an amino acid comprising an allyl sulfide or selenide. In some embodiments, a ruthenium catalyst is Hoveda-Grubbs $2^{nd}$ generation catalyst. In some embodiments, an olefin metathesis reaction comprises reaction of one or more strained alkenes or alkynes.

In some embodiments described herein, a conjugation reaction described herein comprises a (4+2+ cycloadditiona reaction with an alkene.

In some embodiments described herein, a conjugation reaction described herein comprises a cross-coupling reaction. In some embodiments, cross-coupling reactions comprise transition metal catalysts, such as iridium, gold, ruthenium, rhodium, palladium, nickel, platinum, or other transition metal catalyst and one or more ligands. In some embodiments, transition metal catalysts are water-soluble. In some embodiments described herein, a conjugation reaction described herein comprises a Suzuki-Miyaura cross-coupling reaction. In some embodiments described herein, a conjugation reaction described herein comprises reaction of an aryl halide (or triflate, or tosylate), an aryl or alkenyl boronic acid, and a palladium catalyst. In some embodiments described herein, a conjugation reaction described herein comprises a Sonogashira cross-coupling reaction. In some embodiments described herein, a conjugation reaction described herein comprises reaction of an aryl halide (or triflate, or tosylate), an alkyne, and a palladium catalyst. In some embodiments, cross-coupling reactions result in attachment of a linker or conjugating moiety to an IL-15 polypeptide via a carbon-carbon bond.

In some embodiments described herein, a conjugation reaction described herein comprises a deprotection or "uncaging" reaction of a reactive group prior to conjugation. In some embodiments, a conjugation reaction described herein comprises uncaging of a reactive group with light, followed by a conjugation reaction. In some embodiments, a reactive group is protected with an aralkyl moiety comprising one or more nitro groups. In some embodiments, uncaging of a reactive group results in a free amine, sulfide, or other reactive group. In some embodiments, a conjugation reaction described herein comprises uncaging of a reactive group with a transition metal catalyst, followed by a conjugation reaction. In some embodiments, the transition metal catalyst comprises palladium and one or more ligands. In some embodiments, a reactive group is protected with an allyl moiety. In some embodiments, a reactive group is protected with an allylic carbamate. In some embodiments, a reactive group is protected with a propargylic moiety. In some embodiments, a reactive group is protected with a propargyl carbamate. In some embodiments, a reactive group is protected with a dienophile, wherein exposure to a diene (such as a tetrazine) results in deprotection of the reactive group.

In some embodiments described herein, a conjugation reaction described herein comprises a ligand-directed reaction, wherein a ligand (optionally) attached to a reactive group) facilitates the site of conjugation between the reactive group and the IL-15 polypeptide. In some embodiments, the ligand is cleaved during or after reaction of the IL-15 polypeptide with the reactive group. In some embodiments, the conjugation site of the IL-15 polypeptide is a natural amino acid. In some embodiments, the conjugation site of the IL-15 polypeptide is a lysine, cysteine, or serine. In some embodiments, the conjugation site of the IL-15 polypeptide is an unnatural amino acid described herein. In some embodiments the reactive group comprises a leaving group, such as an electron-poor aryl or heteroaryl group. In some embodiments the reactive group comprises a leaving group, such as an electron-poor alkyl group that is displaced by the IL-15 polypeptide. In some embodiments, a conjugation reaction described herein comprises reaction of a radical trapping agent with a radical species. In some embodiments, a conjugation reaction described herein comprises an oxidative radical addition reaction. In some embodiments, a radical trapping agent is an arylamine. In some embodiments, a radical species is a tyrosyl radical. In some embodiments, radical species are generated by a ruthenium catalyst (such as [Ru(bpy)$_3$]) and light.

Enzymatic reactions are optionally used for conjugation reactions described herein. Exemplary enzymatic conjugations include SortA-mediated conjugation, a TGs-mediated conjugation, or an FGE-mediated conjugation. In some embodiments, a conjugation reaction described herein comprises native protein ligation (NPL) of a terminal 1-amino-2-thio group with a thioester to form an amide bond.

Various conjugation reactions are described herein for reacting a linker or conjugating moiety with an IL-15 polypeptide, wherein the reaction occurs with a natural ("canonical") amino acid in the IL-15 polypeptide. In some embodiments, the natural amino acid is found at a conjugation position is found in a wild type sequence, or alternatively the position has been mutated. In some embodiments, a conjugation reaction comprises formation of a disulfide bond at an IL-15 residue. In some embodiments, a conjugation reaction comprises a 1,4 Michael addition reaction of a cysteine or lysine. In some embodiments, a conjugation reaction comprises a cyanobenzothiazole ligation of an IL-15. In some embodiments, a conjugation reaction comprises crosslinking with an acetone moiety, such as 1,3-dichloro-2-propionone. In some embodiments, a conjugation reaction comprises a 1,4 Michael addition to a dehydroalanine, formed by reaction of cysteine with O-mesitylenesulfonylhydroxylamine. In some embodiments a conjugation reaction comprises reaction of a tyrosine with a triazolinedione (TAD), or TAD derivative. In some embodiments a conjugation reaction comprises reaction of a tryptophan with a rhodium carbenoid.

Methods of Use

Proliferative Diseases or Conditions

In some embodiments, described herein is a method of treating a proliferative disease or condition in a subject in need thereof, which comprises administering to the subject a therapeutically effective amount of an IL-15 conjugate described herein. In some embodiments, the IL-15 conjugate comprises an isolated and purified IL-15 polypeptide and a conjugating moiety, wherein the IL-15 conjugate has a decreased affinity to an IL-15 receptor α (IL-15Rα) subunit relative to a wild-type IL-15 polypeptide. In some embodiments, the IL-15 conjugate comprises an isolated and purified IL-15 polypeptide; and a conjugating moiety that binds to the isolated and purified IL-15 polypeptide at an amino acid position selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the numbering of the amino acid residues corresponds to SEQ ID NO: 1. In some embodiments, the IL-15 conjugate comprises an isolated and purified IL-15 polypeptide; and a conjugating moiety that binds to the isolated and purified IL-15 polypeptide at an amino acid position selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114.

In some embodiments, the IL-15 conjugate preferentially interact with the IL-15Rβ and IL-15Rβγ subunits to form an IL-15/IL-15Rβγ complex. In some embodiments, the IL-15/IL-15Rβγ complex stimulates and/or enhances expansion of Teff cells (e.g., CD8+ Teff cells) and/or NK cells. In additional cases, the expansion of Teff cells skews the Teff:Treg ratio toward the Teff population.

In some embodiments, the proliferative disease or condition is a cancer. In some embodiments, the cancer is a solid tumor. In some embodiments, an IL-15 conjugate described herein is administered to a subject in need thereof, for treating a solid tumor. In such cases, the subject has a bladder cancer, a bone cancer, a brain cancer, a breast cancer, a colorectal cancer, an esophageal cancer, an eye cancer, a head and neck cancer, a kidney cancer, a lung cancer, a melanoma, an ovarian cancer, a pancreatic cancer, or a prostate cancer. In some embodiments, the IL-15 conjugate is administered to a subject for the treatment of a bladder cancer. In some embodiments, the IL-15 conjugate is administered to a subject for the treatment of a breast cancer. In some embodiments, the IL-15 conjugate is administered to a subject for the treatment of a colorectal cancer. In some embodiments, the IL-15 conjugate is administered to a subject for the treatment of an esophageal cancer. In some embodiments, the IL-15 conjugate is administered to a subject for the treatment of a head and neck cancer. In some embodiments, the IL-15 conjugate is administered to a subject for the treatment of a kidney cancer. In some embodiments, the IL-15 conjugate is administered to a subject for the treatment of a lung cancer. In some embodiments, the IL-15 conjugate is administered to a subject for the treatment of a melanoma. In some embodiments, the IL-15 conjugate is administered to a subject for the treatment of an ovarian cancer. In some embodiments, the IL-15 conjugate is administered to a subject for the treatment of a pancreatic cancer. In some embodiments, the IL-15 conjugate is administered to a subject for the treatment of a prostate cancer. In some embodiments, the IL-15 conjugate is administered to a subject for the treatment of a metastatic cancer. In additional cases, the IL-15 conjugate is administered to a subject for the treatment of a relapsed or refractory cancer.

In some embodiments, the cancer is a hematologic malignancy. In some embodiments, an IL-15 conjugate described herein is administered to a subject in need thereof, for treating a hematologic malignancy. In some embodiments, the subject has chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the IL-15 conjugate is administered to a subject for the treatment of CLL. In some embodiments, the IL-15 conjugate is administered to a subject for the treatment of SLL. In some embodiments, the IL-15 conjugate is administered to a subject for the treatment of FL. In some embodiments, the IL-15 conjugate is administered to a subject for the treatment of DLBCL. In some embodiments, the IL-15 conjugate is administered to a subject for the treatment of MCL. In some embodiments, the IL-15 conjugate is administered to a subject for the treatment of Waldenstrom's macroglobulinemia. In some embodiments, the IL-15 conjugate is administered to a subject for the treatment of multiple myeloma. In some embodiments, the IL-15 conjugate is administered to a subject for the treatment of Burkitt's lymphoma. In some embodiments, the IL-15 conjugate is administered to a subject for the treatment of a metastatic hematologic malignancy. In additional cases, the IL-15 conjugate is administered to a subject for the treatment of a relapsed or refractory hematologic malignancy.

In some embodiments, an additional therapeutic agent is further administered to the subject. In some embodiments, the additional therapeutic agent is administered simultaneously with an IL-15 conjugate. In other cases, the additional therapeutic agent and the IL-15 conjugate are administered sequentially, e.g., the IL-15 conjugate is administered prior to the additional therapeutic agent or that the IL-15 conjugate is administered after administration of the additional therapeutic agent.

In some embodiments, the additional therapeutic agent comprises a chemotherapeutic agent, an immunotherapeutic agent, a targeted therapy, radiation therapy, or a combination thereof. Illustrative additional therapeutic agents include, but are not limited to, alkylating agents such as altretamine, busulfan, carboplatin, carmustine, chlorambucil, cisplatin, cyclophosphamide, dacarbazine, lomustine, melphalan, oxalaplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some cases, the additional therapeutic agent comprises a first-line therapy. As used herein, "first-line therapy" comprises a primary treatment for a subject with a cancer. In some instances, the cancer is a primary or local cancer. In other instances, the cancer is a metastatic or recurrent cancer. In some cases, the first-line therapy comprises chemotherapy. In other cases, the first-line treatment comprises immunotherapy, targeted therapy, or radiation therapy. A skilled artisan would readily understand that different first-line treatments may be applicable to different type of cancers.

In some embodiments, an IL-15 conjugate is administered with an additional therapeutic agent selected from an alkylating agent such as altretamine, busulfan, carboplatin, carmustine, chlorambucil, cisplatin, cyclophosphamide, dacarbazine, lomustine, melphalan, oxalaplatin, temozolomide, or thiotepa; an antimetabolite such as 5-fluorouracil (5-FU), 6-mercaptopurine (6-MP), capecitabine, cytarabine, floxuridine, fludarabine, gemcitabine, hydroxyurea, methotrexate, or pemetrexed; an anthracycline such as daunorubicin, doxorubicin, epirubicin, or idarubicin; a topoisomerase I inhibitor such as topotecan or irinotecan (CPT-11); a topoisomerase II inhibitor such as etoposide (VP-16), teniposide, or mitoxantrone; a mitotic inhibitor such as docetaxel, estramustine, ixabepilone, paclitaxel, vinblastine, vincristine, or vinorelbine; or a corticosteroid such as prednisone, methylprednisolone, or dexamethasone.

In some instances, an IL-15 conjugate described herein is administered with an inhibitor of the enzyme poly ADP ribose polymerase (PARP). Exemplary PARP inhibitors include, but are not limited to, olaparib (AZD-2281, Lynparza®, from Astra Zeneca), rucaparib (PF-01367338, Rubraca®, from Clovis Oncology), niraparib (MK-4827, Zejula®, from Tesaro), talazoparib (BMN-673, from BioMarin Pharmaceutical Inc.), veliparib (ABT-888, from AbbVie), CK-102 (formerly CEP 9722, from Teva Pharmaceutical Industries Ltd.), E7016 (from Eisai), iniparib (BSI 201, from Sanofi), and pamiparib (BGB-290, from BeiGene). In some cases, the IL-15 conjugate is administered in combination with a PARP inhibitor such as olaparib, rucaparib, niraparib, talazoparib, veliparib, CK-102, E7016, iniparib, or pamiparib.

In some embodiments, an IL-15 conjugate described herein is administered with a tyrosine kinase inhibitor (TKI). Exemplary TKIs include, but are not limited to, afatinib, alectinib, axitinib, bosutinib, cabozantinib, ceritinib, cobimetinib, crizotinib, dabrafenib, dasatinib, erlotinib, gefitinib, ibrutinib, imatinib, lapatinib, lenvatinib, nilotinib, nintedanib, osimertinib, pazopanib, ponatinib, regorafenib, ruxolitinib, sorafenib, sunitinib, tofacitinib, and vandetanib.

In some instances, an IL-15 conjugate described herein is administered with an immune checkpoint modulator. Exemplary checkpoint modulators include:

PD-L1 modulators such as Genentech's MPDL3280A (RG7446), Avelumab (Bavencio) from Merck/Pfizer, durvalumab (Imfinzi) from AstraZeneca, Anti-mouse PD-L1 antibody Clone 10F.9G2 (Cat #BE0101) from BioXcell, anti-PD-L1 monoclonal antibody MDX-1105 (BMS-936559), BMS-935559 and BMS-986192 from Bristol-Meyer's Squibb, MSB0010718C, mouse anti-PD-L1 Clone 29E.2A3, CX-072 from XytomX Therapeutics, FAZ053 from Novartis Pharmaceuticals, KN035 from 3D Medicine, LY3300054 from Eli Lilly, and AstraZeneca's MEDI4736;

PD-L2 modulators such as GlaxoSmithKline's AMP-224 (Amplimmune), and rHIgM12B7;

PD-1 modulators such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG$_4$ monoclonal antibody nivolumab (Opdivo®, BMS-936558, MDX1106), AstraZeneca's AMP-514 and AMP-224, sintilimab (IBI-308) from Eli Lilly/Innovent Biologics, AGEN 2034 from Agenus, BGB-A317 from BeiGene, B1-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, PDR001 from Novartis Pharmaceuticals, PF-06801591 from Pfizer, REGN2810 from Regeneron Pharmaceuticals, and Pidilizumab (CT-011) from CureTech Ltd;

CTLA-4 modulators such as Bristol Meyers Squibb's anti-CTLA-4 antibody ipilimumab (also known as Yervoy®, MDX-010, BMS-734016 and MDX-101), anti-CTLA4 antibody clone 9H10 from Millipore, Pfizer's tremelimumab (CP-675,206, ticilimumab), AGEN 1884 from Agenus, and anti-CTLA4 antibody clone BNI3 from Abcam;

LAG3 modulators such as anti-Lag-3 antibody clone eBioC9B7W (C9B7W) from eBioscience, anti-Lag3 antibody LS-B2237 from LifeSpan Biosciences, IMP701 and LAG525 from Novartis Pharmaceuticals, IMP321 (ImmuFact) from Immutep, anti-Lag3 antibody BMS-986016, BMS-986016 from Bristol-Myers Squibb, REGN3767 from Regeneron Pharmaceuticals, and the LAG-3 chimeric antibody A9H12;

B7-H3 modulators such as MGA271;

KIR modulators such as Lirilumab (IPH2101) from Bristol-Myers Squibb;

CD137 modulators such as urelumab (BMS-663513, Bristol-Myers Squibb), PF-05082566 (anti-4-1BB, PF-2566, Pfizer), or XmAb-5592 (Xencor);

PS modulators such as Bavituximab;

OX40 modulators such as BMS-986178 from Bristol-Myers Squibb, GSK3174998 from GlaxoSmithKline, INCAGN1949 from Agenus, MEDI0562 from MedImmune, PF-04518600 from Pfizer, or RG7888 from Genentech;

GITR modulators such as GWN323 from Novartis Pharmaceuticals, INCAGN1876 from Agenus, or TRX518 from Leap Therapeutics;

TIM3 modulators such as MBG453 from Novartis Pharmaceuticals, or TSR-042 from TESARO;

and modulators such as an antibody or fragments (e.g., a monoclonal antibody, a human, humanized, or chimeric antibody) thereof, RNAi molecules, or small molecules to CD52, CD30, CD20, CD33, CD27, ICOS, BTLA (CD272), CD160, 2B4, LAIR1, TIGHT, LIGHT, DR3, CD226, CD2, or SLAM.

In some instances, the IL-15 conjugate is administered in combination with pembrolizumab, nivolumab, tremelimumab, or ipilimumab.

In some instances, an IL-15 conjugate described herein is administered with an antibody such as alemtuzumab, trastuzumab, ibritumomab tiuxetan, brentuximab vedotin, ado-trastuzumab emtansine, or blinatumomab.

In some instances, an IL-15 conjugate is administered with an additional therapeutic agent selected from an anti-VEGFR antibody. Exemplary anti-VEGFR antibodies include, but are not limited to, bevacizumab or ramucirumab. In some instances, the IL-15 conjugate enhances the ADCC effect of the additional therapeutic agent.

In some instances, an IL-15 conjugate is administered with an additional therapeutic agent selected from cetuximab, imgatuzumab, matuzumab (EMD 72000), tomuzotuximab, or panitumumab. In some instances, the IL-15 conjugate enhances the ADCC effect of the additional therapeutic agent.

In some instances, an IL-15 conjugate is administered with an additional therapeutic agent selected from an additional cytokine (e.g., either a native cytokine or an engineered cytokine such as a PEGylated and/or fusion cytokine). In some instances, the additional cytokine enhances and/or synergizes T effector cell expansion and/or proliferation. In some cases, the additional cytokine comprises IL-1β, IL-2, IL-6, IL-7, IL-10, IL-12, IL-18, IL-21, or TNFα. In some cases, the additional cytokine is IL-2. In some cases, the additional cytokine is IL-21. In some cases, the additional cytokine is IL-10. In some cases, the additional cytokine is TNFα.

In some instances, an IL-15 conjugate is administered with an additional therapeutic agent selected from a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2β, CFA, or Flagellin. In some cases, the IL-21 conjugate is administered with one or more TLR agonists selected from TLR1, TLR2, TLR3, TLR4, TLR5, TLR6, TLR7, TLR8, and TLR9. In some cases, the IL-15 conjugate is administered with one or more TLR agonists selected from Pam3Cys, CFA, MALP2, Pam2Cys, FSL-1, Hib-OMPC, Poly I:C, poly A:U, AGP, MPL A, RC-529, MDF2β, CFA, and Flagellin.

In some embodiments, an IL-15 conjugate described herein is used in conjunction with an adoptive T cell transfer (ACT) therapy. In one embodiment, ACT involves identification of autologous T lymphocytes in a subject with, e.g., anti-tumor activity, expansion of the autologous T lymphocytes in vitro, and subsequent reinfusion of the expanded T lymphocytes into the subject. In another embodiment, ACT comprises use of allogeneic T lymphocytes with, e.g., anti-tumor activity, expansion of the T lymphocytes in vitro, and subseqent infusion of the expanded allogeneic T lymphocytes into a subject in need thereof. In some embodiments, an IL-15 conjugate described herein is used in conjunction with an autologous T lymphocytes as part of an ACT therapy. In other instances, an IL-15 conjugate described herein is used in conjunction with an allogeneic T lymphocytes as part of an ACT therapy. In some embodiments, the IL-15 conjugate is administered simultaneously with the ACT therapy to a subject in need thereof. In other cases, the IL-15 conjugate is administered sequentially with the ACT therapy to a subject in need thereof.

In some embodiments, an IL-15 conjugate described herein is used for an ex vivo activation and/or expansion of an autologous and/or allogenic T cell transfer. In such cases, the IL-15 conjugate is used to activate and/or expand a sample comprising autologous and/or allogenic T cells and the IL-15 conjugate is optionally removed from the sample prior to administering the sample to a subject in need thereof.

In some embodiments, an IL-15 conjugate described herein is administered with a vaccine. In some instances, an IL-21 conjugate is utilized in combination with an oncolytic virus. In such cases, the IL-21 conjugate acts as a stimulatory agent to modulate the immune response. In some instances, the IL-21 conjugate is used with an oncolytic virus as part of an adjuvant therapy. Exemplary oncolytic viruses include T-Vec (Amgen), G47Δ (Todo et al.), JX-594 (Sillajen), CG0070 (Cold Genesys), and Reolysin (Oncolytics Biotech). In some cases, the IL-21 conjugate is used in combination with an oncolytic virus such as T-Vec, G47Δ, JX-594, CG0070, or Reolysin.

In some embodiments, an IL-15 conjugate is administered in combination with a radiation therapy.

Methods of Cell Population Expansion

In some embodiments, additionally described herein are methods of expanding lymphocyte populations, e.g., effector T (Teff) cell, memory T (Tmem) cell, and/or Natural Killer (NK) cell populations. In some embodiments, the method comprises contacting a cell with a cytokine conjugate described herein, and interacting the cytokine with a cytokine receptor to form a complex, wherein the complex stimulates expansion of a distinct lymphocyte population.

In some embodiments, the method of expanding effector T (Teff) cell, memory T (Tmem) cell, and/or Natural Killer (NK) cell populations, comprising: (a) contacting a cell with a modified IL-15 polypeptide or an IL-15 conjugate; and interacting the IL-15 with IL-15Rβ and IL-15Rγ subunits to form an IL-15/IL-15Rβγ complex; wherein the IL-15 conjugate has a decreased affinity to IL-15Rα subunit, and wherein the IL-15/IL-15Rβγ complex stimulates the expansion of Teff, Tmem, and NK cells. As described herein, in some embodiments, the modified IL-15 polypeptide comprise at least one post-translationally modified unnatural amino acid at a residue position selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position is selected from N1, W2, V3, N4, I6, S7, D8, K10, K11, E13, D14, L15, Q17, 518, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114. In some embodiments, the residue position is selected from E13, D14, L15, Q17, 518, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110. In some embodiments, the residue position is selected from D14, Q17, 518, K41, S51, L52, G55, D56, A57, S58, S75, S76, N77, N79, V80, T81, S83, G84, E92, K94, N95, K97, and E98. In some embodiments, the residue position is selected from N1, N4, S7, D8, K11, D61, T62, E64, N65, I68, L69, and N72. In some embodiments, the residue position is selected from V3, I6, K10, E28, S29, D30, V31, H32, P33, S102, V104, H105, Q108, M109, I111, N112, T113, and S114. In some embodiments, the residue position is selected from D22, A23, T24, L25, Y26, L44, E46, Q48, V49, E53, E89, E90, and E93. In some embodiments, the residue position is selected from Y26, E46, V49, E53, and L25. In some embodiments, the residue position is selected from V3, K10, S29, D30, H32, H105, Q108, M109, I111, N112, T113, and S114. In some embodiments, the residue position is selected from N4, S7, K11, and D61. In some embodiments, the residue position is selected from L25, E53, N77, and S83. In some embodiments, the residue position is selected from L25 and E53. In some embodiments, the residue position is selected from E46, Y26, V49, E53, T24, N4, K11, N65, L69, S18, H20, and S83. In some embodiments, the residue position is selected from E46, Y26, V49, E53, and T24. In some embodiments, the residue position is selected from E46, V49, E53, and T24. In some embodiments, the residue position is selected from Y26, V49, E53, and T24. In some embodiments, the residue position is selected from V49, E53, and T24. In some embodiments, the residue position is selected from E46 and Y26. In some embodiments, the residue position is E46. In some embodiments, the residue position is L25. In some embodiments, the residue position is Y26. In some embodiments, the residue position is V49. In some embodiments, the residue position is E53. In some embodiments, the residue position is T24. In some embodiments, the residue position is N77. In some embodiments, the residue position is S83.

Methods of expanding effector T (Teff) cell, memory T (Tmem) cells, and/or Natural Killer (NK) cell populations as described herein, in some embodiments, comprise contacting a cell with an IL-15 conjugate. As described herein, in some embodiments, the interleukin 15 (IL-15) conjugates comprise: an isolated and purified IL-15 polypeptide; and a conjugating moiety that binds to the isolated and purified IL-15 polypeptide at an amino acid position selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position is selected from N1, W2, V3, N4, I6, S7, D8, K10, K11, E13, D14, L15, Q17, 518, M19, H20, I21, D22, A23, T24, L25, Y26, E28, S29, D30, V31, H32, P33, S34, C35, K36, V37, T38, K41, L44, E46, Q48, V49, 551, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114. In some embodiments, the residue position is selected from E13, D14, L15, Q17, 518, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110. In some embodiments, the residue position is selected from D14, Q17, S18, K41, S51, L52, G55, D56, A57, S58, S75, S76, N77, N79, V80, T81, S83, G84, E92, K94, N95, K97, and E98. In some embodiments, the residue position is selected from N1, N4, S7, D8, K11, D61, T62, E64, N65, I68, L69, and N72. In some embodiments, the residue position is selected from V3, I6, K10, E28, S29, D30, V31, H32, P33, S102, V104, H105, Q108, M109, I111, N112, T113, and S114. In some embodiments, the residue position is selected from D22, A23, T24, L25, Y26, L44, E46, Q48, V49, E53, E89, E90, and E93. In some embodiments, the residue position is selected from Y26, E46, V49, E53, and L25. In some embodiments, the residue position is selected from V3, K10, S29, D30, H32, H105, Q108, M109, I111, N112, T113, and S114. In some embodiments, the residue position is selected from N4, S7, K11, and D61. In some embodiments, the residue position is selected from L25, E53, N77, and S83. In some embodiments, the residue position is selected from L25 and E53. In some embodiments, the residue position is selected from E46, Y26, V49, E53, T24, N4, K11, N65, L69, S18, H20, and S83. In some embodiments, the residue position is selected from E46, Y26, V49, E53, and T24. In some embodiments, the residue position is selected from E46, V49, E53, and T24. In some embodiments, the residue position is selected from Y26, V49, E53, and T24. In some embodiments, the residue position is selected from V49, E53, and T24. In some embodiments, the residue position is selected from E46 and Y26. In some embodiments, the residue position is E46. In some embodiments, the residue position is L25. In some embodiments, the residue position is Y26. In some embodiments, the residue position is V49. In some embodiments, the residue position is E53. In some embodiments, the residue position is T24. In some embodiments, the residue position is N77. In some embodiments, the residue position is S83.

IL-15 Polypeptide Production

In some embodiments, an IL-15 polypeptides described herein, either containing a natural amino acid mutation or an unnatural amino acid mutation, are generated recombinantly or are synthesized chemically. In some embodiments, the IL-15 polypeptides described herein are generated recombinantly, for example, either by a host cell system, or in a cell-free system.

In some embodiments, the IL-15 polypeptides are generated recombinantly through a host cell system. In some embodiments, the host cell is a eukaryotic cell (e g, mammalian cell, insect cells, yeast cells or plant cell), a prokaryotic cell (e.g., gram-positive bacterium or a gram-negative bacterium), or an archaeal cell. In some cases, a eukaryotic host cell is a mammalian host cell. In some cases, a mammalian host cell is a stable cell line, or a cell line that has incorporated a genetic material of interest into its own genome and has the capability to express the product of the genetic material after many generations of cell division. In other cases, a mammalian host cell is a transient cell line, or a cell line that has not incorporated a genetic material of interest into its own genome and does not have the capability to express the product of the genetic material after many generations of cell division.

Exemplary mammalian host cells include 293T cell line, 293A cell line, 293FT cell line, 293F cells, 293 H cells, A549 cells, MDCK cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some embodiments, an eukaryotic host cell is an insect host cell. Exemplary insect host cell include *Drosophila* S2 cells, Sf9 cells, Sf21 cells, High Five™ cells, and expresSF+® cells.

In some embodiments, a eukaryotic host cell is a yeast host cell. Exemplary yeast host cells include *Pichia pastoris* yeast strains such as GS115, KM71H, SMD1168, SMD1168H, and X-33, and *Saccharomyces cerevisiae* yeast strain such as INVSc1.

In some embodiments, a eukaryotic host cell is a plant host cell. In some embodiments, the plant cells comprise a cell from algae. Exemplary plant cell lines include strains from *Chlamydomonas reinhardtii* 137c, or *Synechococcus elongatus* PPC 7942.

In some embodiments, a host cell is a prokaryotic host cell. Exemplary prokaryotic host cells include BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some embodiments, suitable polynucleic acid molecules or vectors for the production of an IL-15 polypeptide described herein include any suitable vectors derived from either a eukaryotic or prokaryotic sources. Exemplary polynucleic acid molecules or vectors include vectors from bacteria (e.g., *E. coli*), insects, yeast (e.g., *Pichia pastoris*), algae, or mammalian source. Bacterial vectors include, for example, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Insect vectors include, for example, pFastBacl, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

Yeast vectors include, for example, Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichia pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Algae vectors include, for example, pChlamy-4 vector or MCS vector.

Mammalian vectors include, for example, transient expression vectors or stable expression vectors. Exemplary mammalian transient expression vectors include p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Exemplary mammalian stable expression vectors include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some embodiments, a cell-free system is used for the production of an IL-15 polypeptide described herein. In some embodiments, a cell-free system comprises a mixture of cytoplasmic and/or nuclear components from a cell (e.g., composed of fully purified recombinant components or partially purified components) and is suitable for in vitro nucleic acid synthesis. In some instances, a cell-free system utilizes prokaryotic cell components. In other instances, a cell-free system utilizes eukaryotic cell components. Nucleic acid synthesis is obtained in a cell-free system based on, for example, *Drosophila* cell, *Xenopus* egg, Archaea, or HeLa cells. Exemplary cell-free systems include *E. coli* S30 Extract system, *E. coli* T7 S30 system, or PURExpress®, XpressCF, and XpressCF+.

Cell-free translation systems variously comprise components such as plasmids, mRNA, DNA, tRNAs, synthetases, release factors, ribosomes, chaperone proteins, translation initiation and elongation factors, natural and/or unnatural amino acids, and/or other components used for protein expression. Such components are optionally modified to improve yields, increase synthesis rate, increase protein product fidelity, or incorporate unnatural amino acids. In some embodiments, cytokines described herein are synthesized using cell-free translation systems described in U.S. Pat. No. 8,778,631; US 2017/0283469; US 2018/0051065; US 2014/0315245; or U.S. Pat. No. 8,778,631. In some embodiments, cell-free translation systems comprise modified release factors, or even removal of one or more release factors from the system. In some embodiments, cell-free translation systems comprise a reduced protease concentration. In some embodiments, cell-free translation systems comprise modified tRNAs with re-assigned codons used to code for unnatural amino acids. In some embodiments, the synthetases described herein for the incorporation of unnatural amino acids are used in cell-free translation systems. In some embodiments, tRNAs are pre-loaded with unnatural amino acids using enzymatic or chemical methods before being added to a cell-free translation system. In some embodiments, components for a cell-free translation system are obtained from modified organisms, such as modified bacteria, yeast, or other organism.

In some embodiments, an IL-15 polypeptide is generated as a circularly permuted form, either via an expression host system or through a cell-free system.

Production of IL-15 Polypeptide Comprising an Unnatural Amino Acid

An orthogonal or expanded genetic code can be used in the present disclosure, in which one or more specific codons present in the nucleic acid sequence of an IL-15 polypeptide are allocated to encode the unnatural amino acid so that it can be genetically incorporated into the IL-15 by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

In some embodiments, the codon is the codon amber, ochre, opal or a quadruplet codon. In some cases, the codon corresponds to the orthogonal tRNA which will be used to carry the unnatural amino acid. In some cases, the codon is amber. In other cases, the codon is an orthogonal codon.

In some instances, the codon is a quadruplet codon, which can be decoded by an orthogonal ribosome ribo-Q1. In some cases, the quadruplet codon is as illustrated in Neumann, et al., "Encoding multiple unnatural amino acids via evolution of a quadruplet-decoding ribosome," Nature, 464(7287): 441-444 (2010).

In some instances, a codon used in the present disclosure is a recoded codon, e.g., a synonymous codon or a rare codon that is replaced with alternative codon. In some cases, the recoded codon is as described in Napolitano, et al., "Emergent rules for codon choice elucidated by editing rare arginine codons in *Escherichia coli*," PNAS, 113(38): E5588-5597 (2016). In some cases, the recoded codon is as described in Ostrov et al., "Design, synthesis, and testing toward a 57-codon genome," Science 353(6301): 819-822 (2016).

In some embodiments, unnatural nucleic acids are utilized leading to incorporation of one or more unnatural amino acids into the IL-15. Exemplary unnatural nucleic acids include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CH$_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-aminoadenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke- and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acids in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, 2-amino-4-oxopyrrolo[2.3-d]pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or $C(R_1)(R_2)$ (R=H, $C_1$-$C_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$O]$_m$ $CH_3$, —O$(CH_2)_n$OCH$_3$, —O$(CH_2)_n$NH$_2$, —O$(CH_2)_n$CH$_3$, —O$(CH_2)_n$ONH$_2$, and -O$(CH_2)_n$ON[$(CH_2)$n $CH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O-(C$_1$-C$_{10}$ alkyl), OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845); 4'-C(CH$_3$)(CH$_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N*-dimethylhydrazine (—CH$_2$—N(CH$_3$)—N(CH$_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, N.Y.; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, the unnatural nucleic acids further form unnatural base pairs. Exemplary unnatural nucleotides capable of forming an unnatural DNA or RNA base pair (UBP) under conditions in vivo includes, but is not limited to, 5SICS, d5SICS, NAM, dNaM, TPT3TP, dTPT3TP, and combinations thereof. In some embodiments, unnatural nucleotides include:

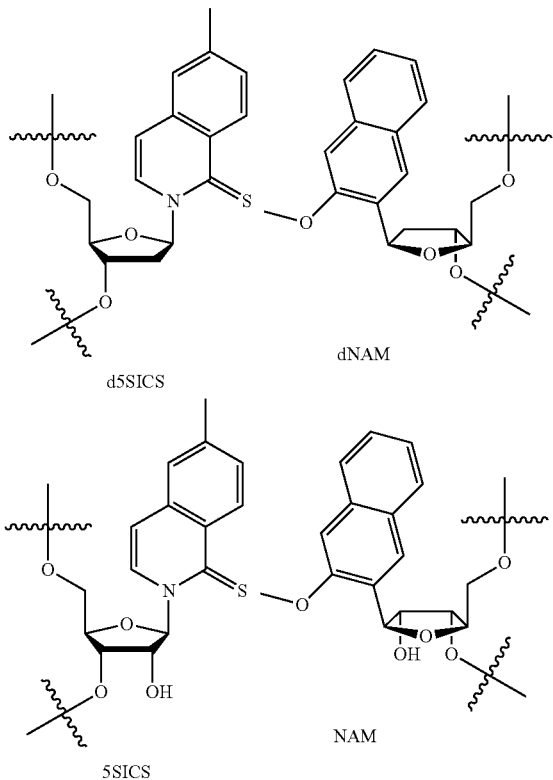

In some embodiments, an unnatural base pair generate an unnatural amino acid described in Dumas et al., "Designing logical codon reassignment—Expanding the chemistry in biology," *Chemical Science*, 6: 50-69 (2015).

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s).

The orthogonal tRNA synthetase/tRNA pair charges a tRNA with an unnatural amino acid and incorporates the unnatural amino acid into the polypeptide chain in response to the codon. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs.

An IL-15 polypeptide comprising an unnatural amino acid(s) are prepared by introducing the nucleic acid constructs described herein comprising the tRNA and tRNA synthetase and comprising a nucleic acid sequence of interest with one or more in-frame orthogonal (stop) codons into a host cell. The host cell is exposed to a physiological solution comprising the unnatural amino acid(s), and the host cells are then maintained under conditions which permit expression of the protein of interest's encoding sequence. The unnatural amino acid(s) is incorporated into the polypeptide chain in response to the codon. For example, one or more unnatural amino acids are incorporated into the IL-15 polypeptide. Alternatively two or more unnatural amino acids may be incorporated into the IL-15 polypeptide at two or more sites in the protein.

When multiple unnatural amino acids are to be incorporated into an IL-15 polypeptide, it will be understood that multiple codons will need to be incorporated into the encoding nucleic acid sequence at the desired positions such that the tRNA synthetase/tRNA pairs can direct the incorporation of the unnatural amino acids in response to the codon(s). At least 1, 2, 3, 4, or more codon encoding nucleic acids maybe incorporated into the nucleic acid sequence of interest.

When it is desired to incorporate more than one type of unnatural amino acid into the protein of interest into a single protein, a second or further orthogonal tRNA-tRNA synthetase pair may be used to incorporate the second or further unnatural amino acid; suitably said second or further orthogonal tRNA-tRNA synthetase pair recognizes a different codon in the nucleic acid encoding the protein of interest so that the two or more unnatural amino acids can be specifically incorporated into different defined sites in the protein in a single manufacturing step. In certain embodiments, two or more orthogonal tRNA-tRNA synthetase pairs may therefore be used.

Once the IL-15 polypeptide incorporating the unnatural amino acid(s) has been produced in the host cell it can be extracted therefrom by a variety of techniques known in the art, including enzymatic, chemical and/or osmotic lysis and physical disruption. The IL-15 polypeptide can be purified by standard techniques known in the art such as preparative chromatography, affinity purification or any other suitable technique.

Suitable host cells may include bacterial cells (e.g., *E. coli*), but most suitably host cells are eukaryotic cells, for example insect cells (e.g. *Drosophila* such as *Drosophila melanogaster*), yeast cells, nematodes (e.g. *Caenorhabditis elegans*), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers may be carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

Pharmaceutical Compositions and Formulations

In some embodiments, the pharmaceutical composition and formulations described herein are administered to a subject by multiple administration routes, including but not limited to, parenteral, oral, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration.

In some embodiments, the pharmaceutical formulations include, but are not limited to, aqueous liquid dispersions, self-emulsifying dispersions, liposomal dispersions, aerosols, immediate release formulations, controlled release formulations, delayed release formulations, extended release formulations, pulsatile release formulations, and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pa. 1975, Liberman, H. A. and Lachman, L., Eds., *Pharmaceutical Dosage Forms*, Marcel Decker, New York, N.Y., 1980, and *Pharmaceutical Dosage Forms and* Drug Delivery Systems, Seventh Ed. (Lippincott Williams & Wilkins 1999).

In some cases, the pharmaceutical composition is formulated as an immunoliposome, which comprises a plurality of IL-15 conjugates bound either directly or indirectly to lipid bilayer of liposomes. Exemplary lipids include, but are not limited to, fatty acids; phospholipids; sterols such as cholesterols; sphingolipids such as sphingomyelin; glycosphingolipids such as gangliosides, globosides, and cerebrosides; surfactant amines such as stearyl, oleyl, and linoleyl amines. In some instances, the lipid comprises a cationic lipid. In some instances, the lipid comprises a phospholipid. Exemplary phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPT"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ('DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

In some embodiments, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, sorbitol, maltose, glucose, or salts like potassium phosphate, sodium citrate, ammonium sulfate and/or other agents such as heparin to increase the solubility and in vivo stability of polypeptides.

In some embodiments, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some embodiments, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more of the IL-15 polypeptides or IL-15 conjugates disclosed herein, and optionally one or more pharmaceutical excipients described herein to facilitate the delivery of IL-15 polypeptides or IL-15 conjugates. Such kits further optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the terms "significant" and "significantly" in reference to receptor binding means a change sufficient to impact binding of the IL-15 polypeptide to a target receptor. In some instances, the term refers to a change of at least 10%, 20%, 30%, 40%, 50%, 60%, 70%, 80%, 90%, 95%, or more. In some instances, the term means a change of at least 2-fold, 3-fold, 4-fold, 5-fold, 6-fold, 7-fold, 8-fold, 9-fold, 10-fold, 50-fold, 100-fold, 500-fold, 1000-fold, or more.

In some instances, the term "significantly" in reference to activation of one or more cell populations via a cytokine signaling complex means a change sufficient to activate the cell population. In some cases, the change to activate the cell population is measured as a receptor signaling potency. In such cases, an EC50 value may be provided. In other cases, an ED50 value may be provided. In additional cases, a concentration or dosage of the cytokine may be provided.

As used herein, the term "potency" refers to the amount of a cytokine (e.g., IL-15 polypeptide) required to produce a target effect. In some instances, the term "potency" refers to the amount of cytokine (e.g., IL-15 polypeptide) required to activate a target cytokine receptor (e.g., IL-15 receptor). In other instances, the term "potency" refers to the amount of cytokine (e.g., IL-15 polypeptide) required to activate a target cell population. In some cases, potency is measured as ED50 (Effective Dose 50), or the dose required to produce 50% of a maximal effect. In other cases, potency is measured as EC50 (Effective Concentration 50), or the dose required to produce the target effect in 50% of the population.

As used herein, the term "tumor infiltrating immune cell(s)" refers to immune cells that have infiltrated into a region comprising tumor cells (e.g., in a tumor microenvironment). In some instances, the tumor infiltrating immune cells are associated with tumor cell destruction, a decrease in tumor cell proliferation, a reduction in tumor burden, or combinations thereof. In some instances, the tumor infiltrating immune cells comprise tumor infiltration lymphocytes (TILs). In some instances, the tumor infiltrating immune cells comprise T cells, B cells, natural killer cells, macrophages, neutrophils, dendritic cells, mast cells, eosinophils or basophils. In some instances, the tumor infiltrating immune cells comprise CD4+ or CD8+ T cells.

EXAMPLES

These examples are provided for illustrative purposes only and not to limit the scope of the claims provided herein.

Example 1

Expression of Modified IL-15 Polypeptides

The modified IL-16 polypeptide was grown at 37° C., 250 rpm, and 5 hours induction. The media component was as illustrated in Table 2.

TABLE 2

| Name | Composition |
|---|---|
| Growth Media | 2xYT |
| | 30.8 mM Potassium phosphate dibasic |
| For 1 L: 2x 2xYT pellets, | 19.2 mM Potassium |
| Potassium phosphate monobasic, | phosphate monobasic |
| Potassium phosphate dibasic | 100 ug/ml Ampicillin |
| | 5 ug/ml Chloramphenicol |
| Autoclave on liquid | 50 ug/ml Zeocin |
| cycle to sterilize | 37.5 uM dTPT3TP |
| | 150 uM dNAMTP |

When expression culture reaches $OD_{600}$ 0.85-0.9, the culture was pre-loaded with NaMTP (at a final concentration of 250 uM), TPT3TP (at a final concentration of 25 uM), and Azido-lysine (at a final concentration of 15 mM). About 15-20 minutes after pre-loading with ribonucleotides and amino acid, IPTG was add and the protein was expressed for about 5 hours.

Inclusion Body

Upon cell pellet collection, the pellets were further processed for inclusion bodies. In brief, a 1L cell pellet was resuspended in 10 ml lysis buffer (20 mM Tris-HCl, pH 8.0; 150 mM NaCl; 1 mM DTT; and Protease inhibitor (1 pellet/50 ml)). After resuspension, the volume of 1 L pellet was increased to 45 ml with lysis buffer and run through the microfluidizer for 2x. The sample was then transferred to a 50 ml centrifuge tube and centrifuge at 16 k rpm for 20 minutes at 4° C. Next, the pellet was resuspended pellet in 5 ml lysis buffer and the total volume was increased to 30 ml with lysis buffer. About 10% Triton X-100 was added to a final concentration of 0.5%. Then the solution was centrifuged at 16 k rpm for 20 minutes at 4° C., and the pellet was then collected and washed 3x with 30 ml lysis buffer. A 5 ml syringe with needles was used to fully resuspend with each wash. After a final spin, discard supernatant and the pellet was snap freeze to store at −80° C.

Solubilization and Refolding

About 5 ml solubilization buffer was added to the inclusion body pellet. After resuspension, the volume was increased to 30 ml in solubilization buffer. Next, the sample was incubated at 4° C. for 30-60 minutes. Then, the sample was transferred to 2x50 ml centrifuge tube (15 ml/tube) and 15 ml dilution buffer was added to each tube. The sample was then dialyzed subsequently in buffer A1 overnight at 4° C., followed by A2 dialysis buffer, A3 dialysis buffer, A4 dialysis buffer, and A5 dialysis buffer. After dialysis, the sample was centrifuged at 4000 rpm for 30 minutes at 4° C. and concentrated to about 5 ml.

TABLE 3 illustrates the solubilization buffers.

| Name | Composition |
|---|---|
| Solubilization Buffer | 6M Guanidine-HCL |
| | 20mM Tris-HCl, |
| | pH 8.0 |
| | 1mM DTT |
| | 20mM Imidazole |
| Dilution Buffer | 3M Guanidine-HCL |
| | 20mM Tris-HCl, |
| | pH 8.0 |
| | 1 mM DTT |
| | 20 mM Imidazole |
| A1 Dialysis Buffer | 2M Guanidine-HCl |
| | 20 mM Tris-HCl, |

TABLE 3-continued illustrates the solubilization buffers.

| Name | Composition |
| --- | --- |
| A2 Dialysis Buffer | pH 8.5<br>150 mM NaCl<br>1 mM GSH<br>(reduced glutathione)<br>0.1 mM GSSG<br>(oxidized glutathione)<br>0.4M L-Arginine<br>0.75M Guanidine-HCl<br>20 mM Tris-HCl,<br>pH 8.5 |
| A3 Dialysis Buffer | 150 mM NaCl<br>1 mM GSH<br>(reduced glutathione)<br>0.1 mM GSSG<br>(oxidized glutathione)<br>0.4M L-Arginine<br>20 mM Tris-HCl,<br>pH 8.5 |
| A4 Dialysis Buffer | 150 mM NaCl<br>1 mM GSH<br>(reduced glutathione)<br>0.1 mM GSSG<br>(oxidized glutathione)<br>0.1M L-Arginine<br>20 mM Tris-HCl,<br>pH 8.5 |
| A5 Dialysis Buffer | 150 mM NaCl<br>20 mM Tris-HCl,<br>pH 7.5<br>12.5 mM NaCl |

Purification

The sample was purified first on a GE HiLoad 16/600 Superdex 200 pg gel filtration column with 1×PBS elution buffer, followed by a GE HiTrapQ anion exchange column to remove free PEG, and then a reverse phase chromatography with a gradient elution of 30%-70% elution buffer in 20 column volumes.

Table 4 illustrates the buffers used for the anion exchange chromatography. Table 5 illustrates the buffers used for the reverse phase chromatography.

TABLE 4

| Name | Composition |
| --- | --- |
| Running buffer | 20 mM Tris-HCl, pH 7.5 |
| Elution buffer | 20 mM Tris-HCl, pH 7.5<br>500 mM NaCl |

TABLE 5

| Name | Composition |
| --- | --- |
| Running buffer | 4.5% Acetonitrile<br>0.043% TFA |
| Elution buffer | 90% Acetonitrile<br>0.028% TFA |

Figure 4:
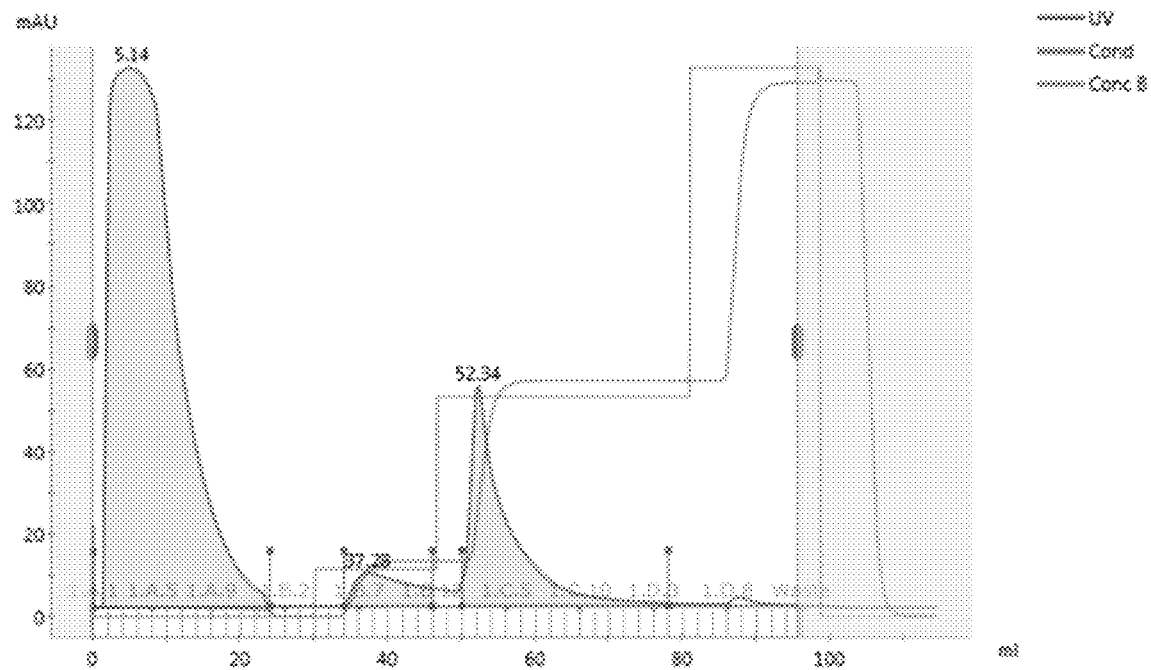
FIG. 4 illustrates a graph of anion exchange chromatography.

FIG. 4 shows an exemplary run of anion exchange chromatography.

Figure 5:
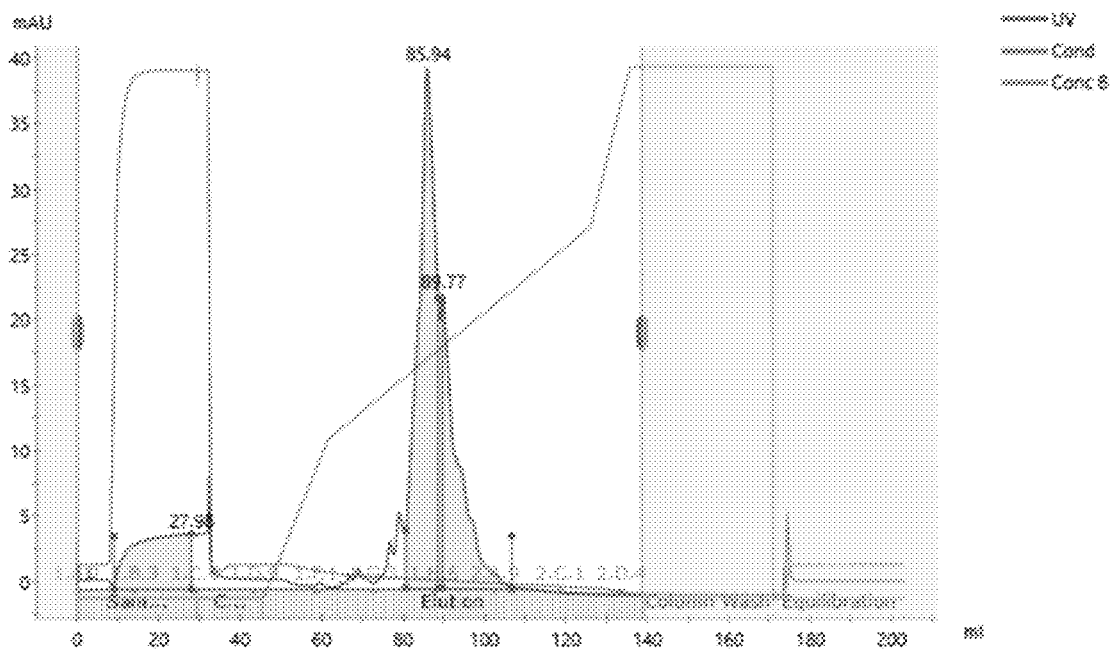
FIG. 5 illustrates a graph of reverse phase chromatography.

FIG. 5 shows an exemplary run of reverse phase chromatography.

Example 2

Cell-Based Screening for Identification of Pegylated IL-15 Compounds with Either Native or No IL-15Rα Engagement Structural data of the IL-15/heterotrimeric receptor signaling complex (PDB: 4GS7) were used to guide design of nAA-pegylation sites to either retain native interaction with the heterotrimeric receptor or specifically abrogate the interaction of IL-15 and IL-15 receptor α subunit (IL-15Rα). Exemplary IL-15 conjugates were subjected to functional analysis: S18, A23, T24, L25, Y26, E46, V49, L52, E53, N77, S83, E89, E90. The IL-15 conjugates were expressed as inclusion bodies in E. coli, purified and re-folded using standard procedures before site-specifically pegylating the IL-15 product using DBCO-mediated copper-free click chemistry to attach stable, covalent mPEG moieties to the AzK. The IL-15 conjugates were screened for functional activity using a colorimetric CTLL2 proliferation assay. CTLL2 is a subclone of mouse T cells that expresses all three IL-15 receptor subunits and requires IL-2/IL-15 for growth. Preliminary experiments were performed to determine the optimal cell density, range of IL-15 standard or IL-15 conjugates for an adequate dose-response curve as well as the incubation time. An in-house recombinant human IL-15 (rHuIL-15) was compared to a commercial IL-15 standard (R&D, catalog #247-IL). Under the defined conditions, the EC50 for the commercial IL-15 standard was about 10.7 pM and 9.7 pM for the in-house rHuIL-15.

Table 6 shows the EC50 data for 30 kDa linear PEGylated IL-15 conjugates designed to retain native interaction with the heterotrimeric IL-15 receptor. Number of values included in the average are indicated between brackets. The results show that the bioconjugation to a 30 kDa PEG does not interfere with potency at the trimeric receptor with less than 5-fold reduced EC50 compare to natural IL-15.

TABLE 6

| Site | Average EC50 (pg/mL) | Average EC50 (PM) | EC50 ratio IL-15 PEG30/rHuIL-15 |
| --- | --- | --- | --- |
| R&D IL-15 | 136.80 ± 36.84 (6) | 10.7 | |
| rHuIL-15 | 124.62 ± 73.75 (6) | 9.7 | |
| S18 PEG30 | 414.10 (2) | 32.1 | 3.3 |
| S83 PEG30 | 199.80 (2) | 15.5 | 1.6 |
| N77 PEG30 | 236.05 (2) | 18.3 | 1.9 |

Table 7 shows the EC50 data for 30 kDa linear and 40 kDa branched PEGylated IL-15 conjugates designed to specifically abrogate the interaction of IL-15 and IL-15 receptor α subunit (IL-15Rα). Number of values included in the average is indicated between brackets. The results show that the bioconjugation to a 30 kDa PEG reduced potency at the trimeric receptor compare to natural IL-15. Bioconjugation of a linear PEG 30 kDa or a branched 40 kDa PEG to V49 moderately reduces the potency to the trimeric receptor compared to rHuIL-15 (~6-8 fold, 814.4 pg/mL to 1,029 pg/mL vs 124.62 pg/mL, respectively). In addition, the potency of L25 PEG39 was more strongly reduced relative to rHuIL-15 (~54-fold, 6,827 pg/mL vs 124.62 pg/mL, respectively).

TABLE 7

| Site | Average EC50 (pg/mL) | Average EC50 (PM) | EC50 ratio IL-15 PEG/rHuIL-15 |
|---|---|---|---|
| R&D IL-15 | 136.80 ± 36.84 (6) | 10.7 | |
| rHuIL-15 | 124.62 ± 73.75 (6) | 9.7 | 1 |
| L25 PEG30 | 6,827 (2) | 529.0 | 54 |
| V49 PEG30 | 814.45 (2) | 63.1 | 6 |
| V49 PEG (40b) | 1,019 | 79.0 | 8 |
| E46 PEG30 | 65,893 | 5,106 | 526 |
| E53 PEG30 | 22,766 | 1,764 | 182 |

Figure 6:
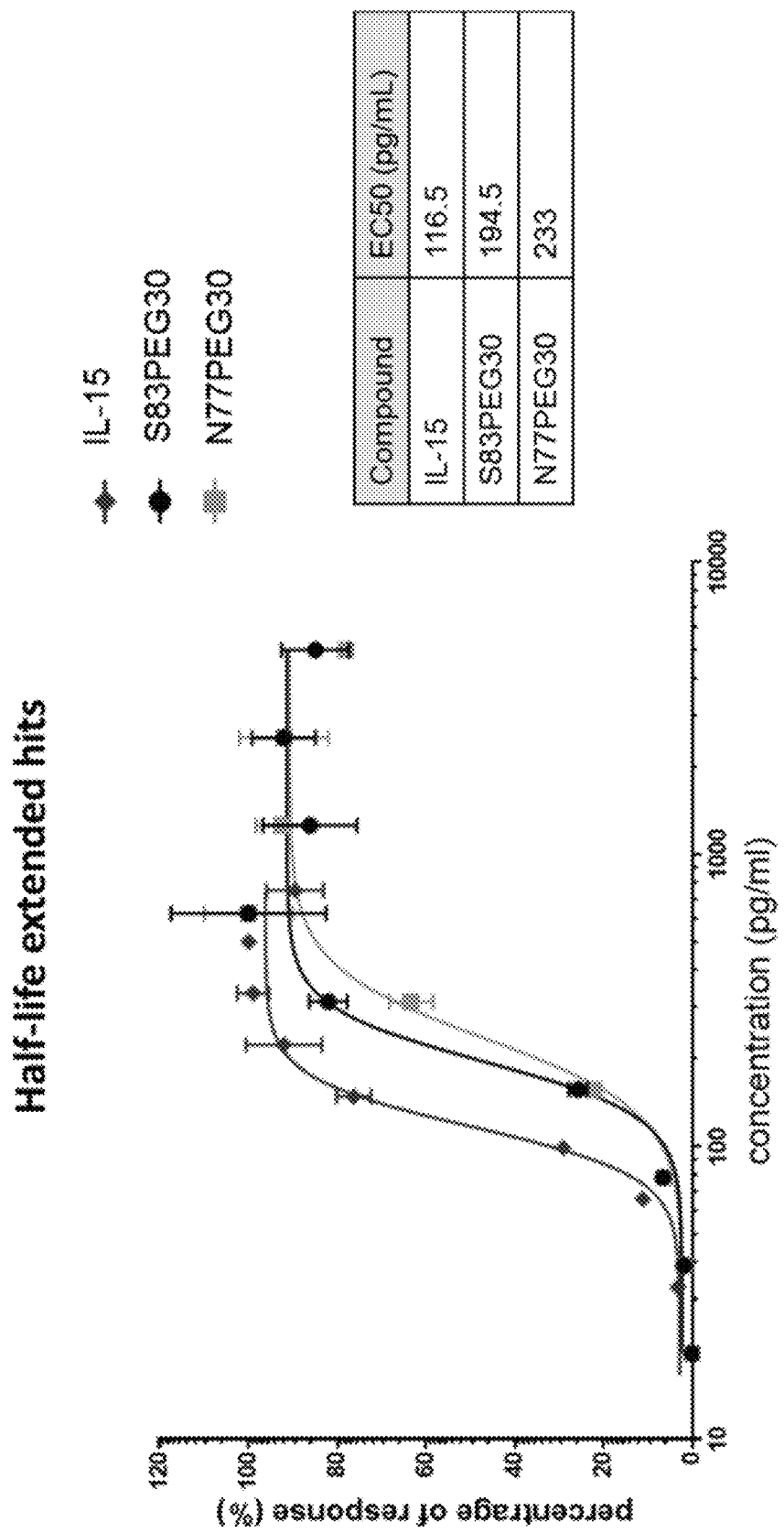
FIG. 6 illustrates the EC50 values for exemplary IL-15 conjugates with native potency in the CTLL2 proliferation assay. Results are plotted as percentage of response.

FIG. 6 illustrates the EC50 values for exemplary IL-15 conjugates with native potency in the CTLL2 proliferation assay. Results are plotted as percentage of response.

Figure 7:
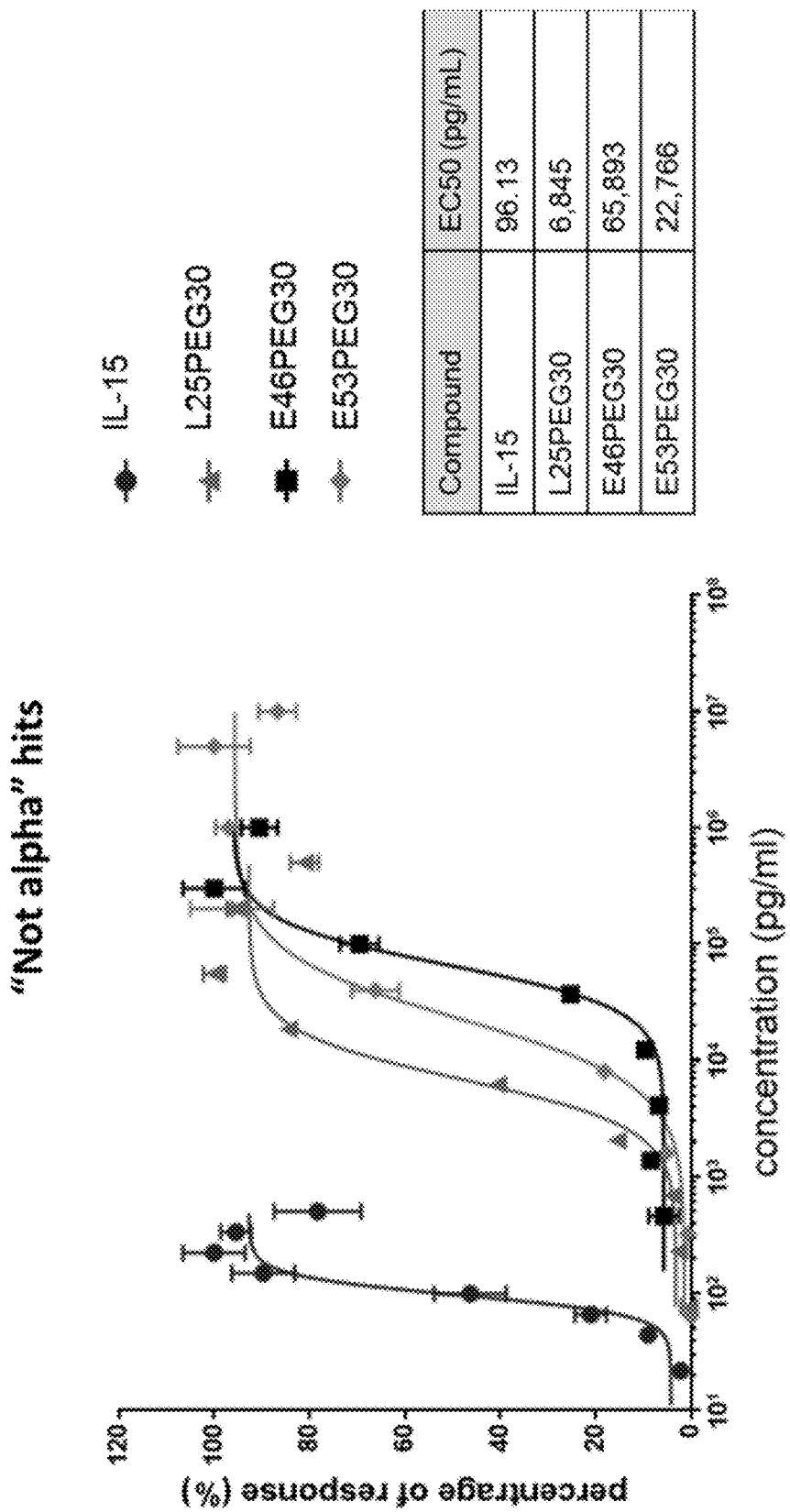
FIG. 7 illustrates the EC50 values for exemplary IL-15 conjugates with reduced potency in the CTLL2 proliferation assay. As shown here, site-specific pegylation contributes to in vitro pharmacology. Results are plotted as percentage of response.

FIG. 7 illustrates the EC50 values for exemplary IL-15 conjugates. As shown here, site-specific pegylation contributes to in vitro pharmacology. Results are plotted as percentage of response.

Figure 8:
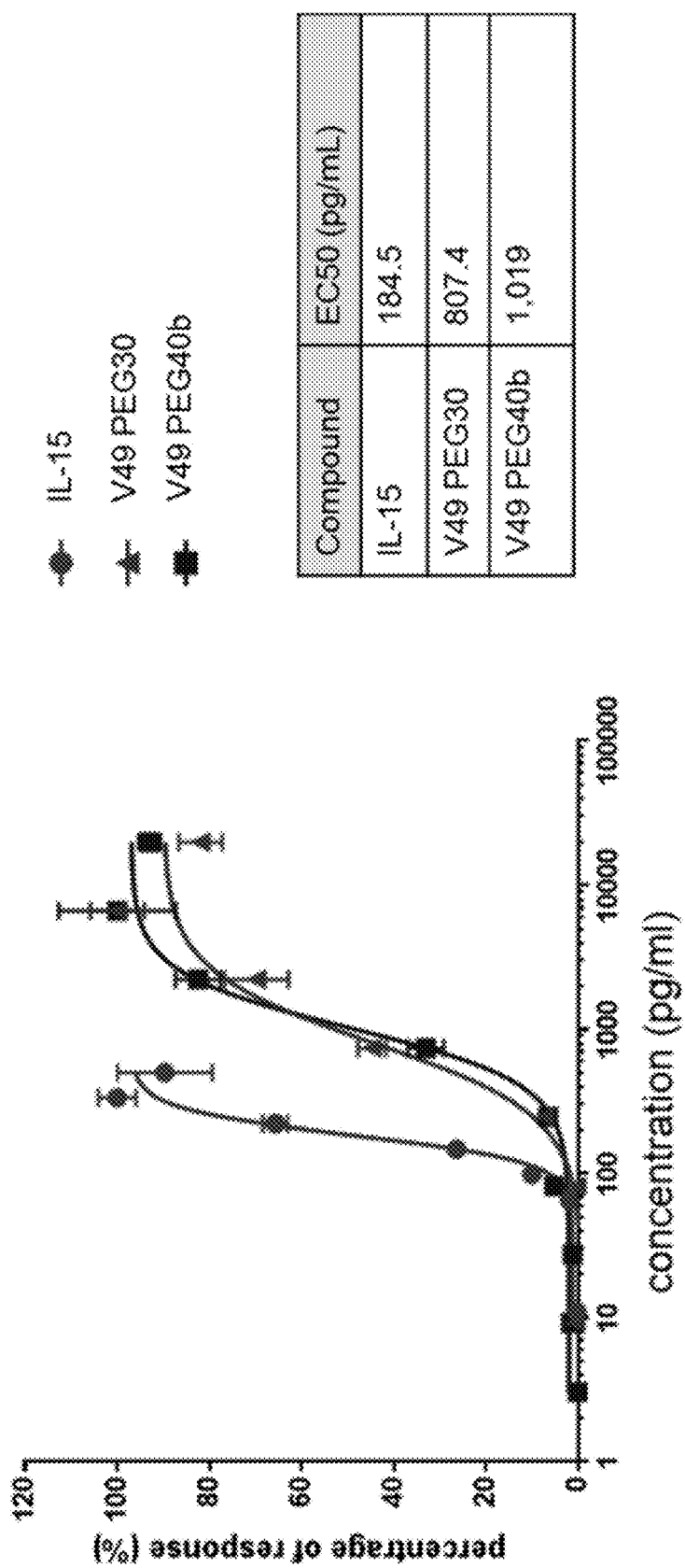
FIG. 8 illustrates the EC50 values for exemplary IL-15 conjugated to different PEG sizes. Results are plotted as percentage of response.

FIG. 8 illustrates the EC50 values for exemplary IL-15 conjugated to different PEG sizes. Results are plotted as percentage of response.

Example 3

Biochemical Interactions of PEGylated IL-15 with Human IL-15 Receptor Subunits

The kinetics of PEGylated IL-15 compound interactions with human IL-15 receptor subunits were measured using Surface Plasmon Resonance (SPR) at Biofizik (San Diego, Calif.). For these studies, human IgG1 Fc-fused IL-15 Rα (Sino Biological #18366-H02H, R&D #7194-IR) and IL-2 Rβ (Sino Biological #10696-H02H) extracellular domains were captured on the surface of a Biacore Protein A-coated CM3 or CM4 sensor chip. Protein A was coupled by amine coupling at a density of approximately 1500 RU on a CM3 chip at 25° C. Approximately 400 RU of IL15Rα-Fc fusion was captured on using a 4 min contact time followed by a 20 minutes wait time prior to the analyte injection. Regeneration of the surface between injections was carried achieved using a 100 mM phosphoric acid. Fresh receptor was captured each cycle following regeneration. These surfaces were probed in triplicates at 25° C. In a typical experiment 10 doses of analyte with a highest concentration of 500 nM were injected. In some cases, a high concentration range was needed and in others the higher doses were omitted from the analysis.

Due to the weaker binding of the compounds to the IL2Rβ, regeneration was not necessary and orthogonal binding studies were conducted without the regeneration step. Approximately 600-700 RU of IL2Rβ Fc fusion was captured on using a 1-2 min contact time of a 1/100 dilution of stock in running buffer. For test compounds 10 doses of analyte with a highest concentration of 1000 nM were injected. Raw data was analyzed using the Scrubber2 program using a double referencing procedure where compound signal is corrected to a blank surface and a buffer injection over the protein surface. See Tables 8-10.

TABLE 8

Kinetic parameters for rHuIL-15 and IL-15 pegylated compounds IL-15Rα subunit surfaces.

| Compound | $k_{on}$ (M$^{-1}$s$^{-1}$) | $k_{off}$ (s$^{-1}$) | $K_D$ (nM) |
|---|---|---|---|
| rHuIL-15 | 2.409E+05 | 5.105E-04 | 0.2117 |
| | 2.450E+06 | 4.763E-04 | 0.1943 |
| | 1.988E+06 | 4.184E-04 | 0.2103 |

TABLE 8-continued

Kinetic parameters for rHuIL-15 and IL-15 pegylated compounds IL-15Rα subunit surfaces.

| Compound | $k_{on}$ (M$^{-1}$s$^{-1}$) | $k_{off}$ (s$^{-1}$) | $K_D$ (nM) |
|---|---|---|---|
| IL15 N77PEG30 | 2.249E+05 | 4.146E-04 | 1.845 |
| | 2.404E+05 | 3.613E-04 | 1.502 |
| | 2.206E+05 | 2.926E-04 | 1.328 |
| IL15 S83PEG30 | 3.669E+05 | 2.137E-04 | 0.5833 |
| | 3.543E+05 | 2.560E-04 | 0.7227 |
| | 3.215E+05 | 1.905E-04 | 0.5909 |

TABLE 9

Kinetic parameters for rHuIL-15 and IL-15 pegylated compounds with reduced binding to IL-15Rα subunit surfaces.

| Compound | $k_{on}$ (M$^{-1}$s$^{-1}$) | $k_{off}$ (s$^{-1}$) | $K_D$ (nM) |
|---|---|---|---|
| rHuIL-15 | 2.409E+05 | 5.105E-04 | 0.2117 |
| | 2.450E+06 | 4.763E-04 | 0.1943 |
| | 1.988E+06 | 4.184E-04 | 0.2103 |
| IL15 L25PEG30 | 5.07E+03 | 1.19E-03 | 233.6 |
| | 3990 | 1.04E-03 | 260.9 |
| | 4930 | 1.22E-03 | 248.1 |
| IL15 E46PEG30 | 3.83E+03 | 4.01E-04 | 104.6 |
| | 2805 | 3.01E-04 | 107.3 |
| | 3.17 | 3.25E-04 | 102.4 |
| IL15 V49PEG30 | 1.73E+05 | 5.30E-04 | 3.066 |
| | 1.54E+05 | 5.76E-04 | 3.75 |
| | 1.50E+05 | 4.22E-04 | 2.823 |
| IL15 V49PEG40b | 1.51E+05 | 6.11E-04 | 4.059 |
| | 1.26E+05 | 5.70E-04 | 4.522 |
| | 1.32E+05 | 4.60E-04 | 3.483 |
| IL15 E53PEG30 | 8.76E+04 | 0.01484 | 169.4 |
| | 8.39E+04 | 0.01614 | 192.4 |
| | 1.42E+05 | 0.02439 | 171 |

TABLE 10

Kinetic parameters for rHuIL-15 and IL-15 pegylated compounds with IL-2Rβ subunit surfaces.

| Compound | $k_{on}$ (M$^{-1}$s$^{-1}$) | $k_{off}$ (s$^{-1}$) | $K_D$ (nM) |
|---|---|---|---|
| rHuIL-15 | 4.161E+05 | 3.095E-02 | 74.4 |
| | 4.223E+05 | 3.251E-02 | 77 |
| | 3.632E+05 | 2.863E-02 | 78.8 |
| IL15 N77PEG30 | 1.101E+05 | 2.220E-02 | 201.6 |
| | 1.158E+05 | 2.361E-02 | 204 |
| | 1.099E+05 | 2.309E-02 | 210.2 |
| IL15 S83PEG30 | 1.214E+05 | 2.517E-02 | 207 |
| | 1.153E+05 | 2.458E-02 | 213 |
| | 1.386E+05 | 2.962E-02 | 213.8 |
| IL15 V49PEG30 | 1.061E+05 | 3.212E-02 | 302.7 |
| | 9.810E+04 | 3.045E-02 | 310.5 |
| | 9.700E+04 | 2.710E-02 | 279.5 |
| IL15 V49PEG40b | 1.187E+05 | 3.091E-02 | 260.5 |
| | 1.071E+05 | 2.690E-02 | 251.2 |
| | 1.061E+05 | 2.552E-02 | 240.5 |
| IL15 E53PEG30 | 5.770E+05 | 3.350E-02 | 58 |
| | 6.010E+05 | 3.525E-02 | 58.6 |
| | 6.300E+05 | 3.348E-02 | 53.1 |
| IL 15 E46PEG30 | 2.01E+04 | 1.650E-02 | 823 |
| IL 15 L25PEG30 | 2.06E+04 | 4.460E-02 | 2,160 |

Figure 9A:
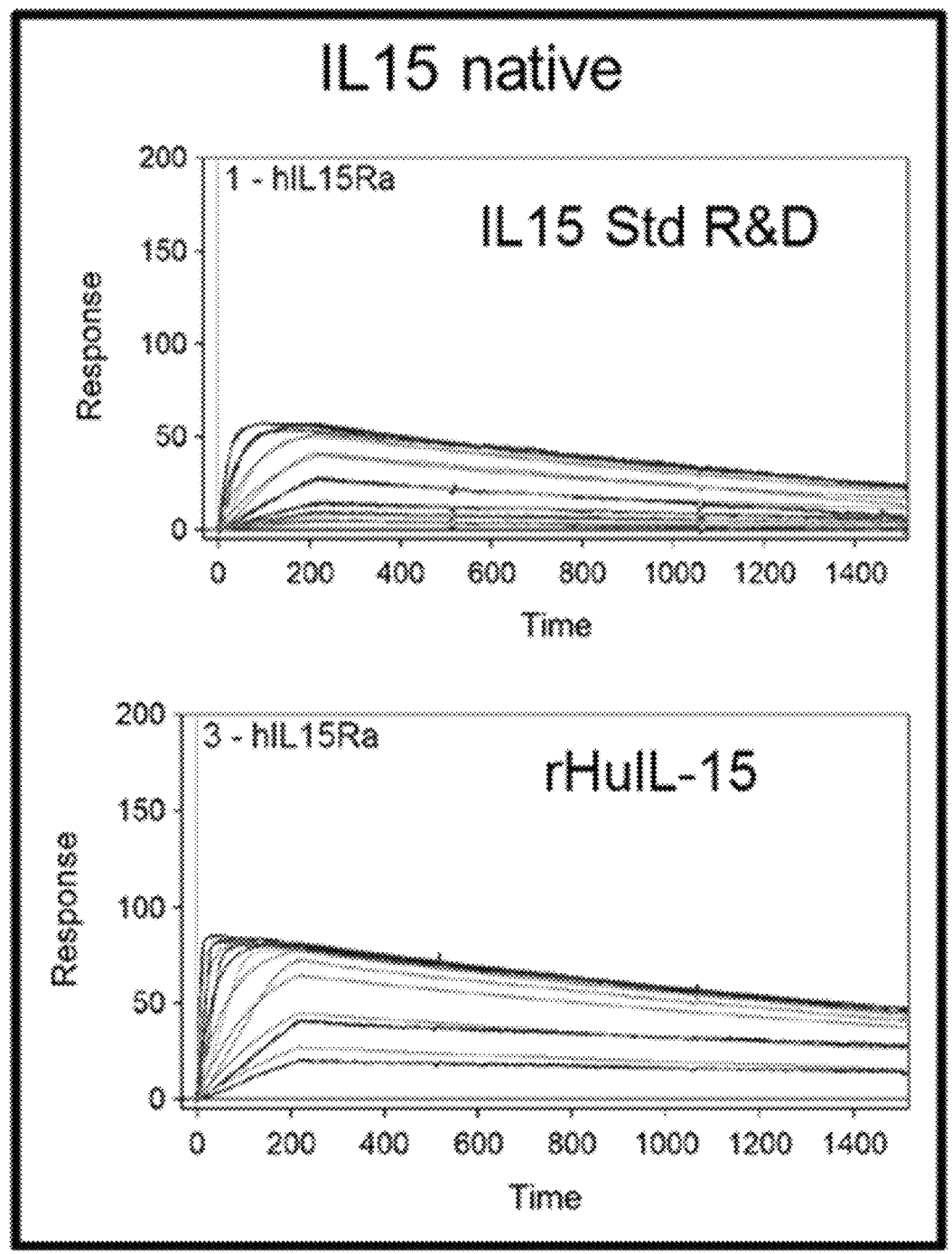
FIG. 9A-FIG. 9C show response units (RU, Y-axis) versus time (s, X-axis) for rHuIL-15, an IL-15 conjugated compounds binding to IL-15Rα.
Figure 9B:
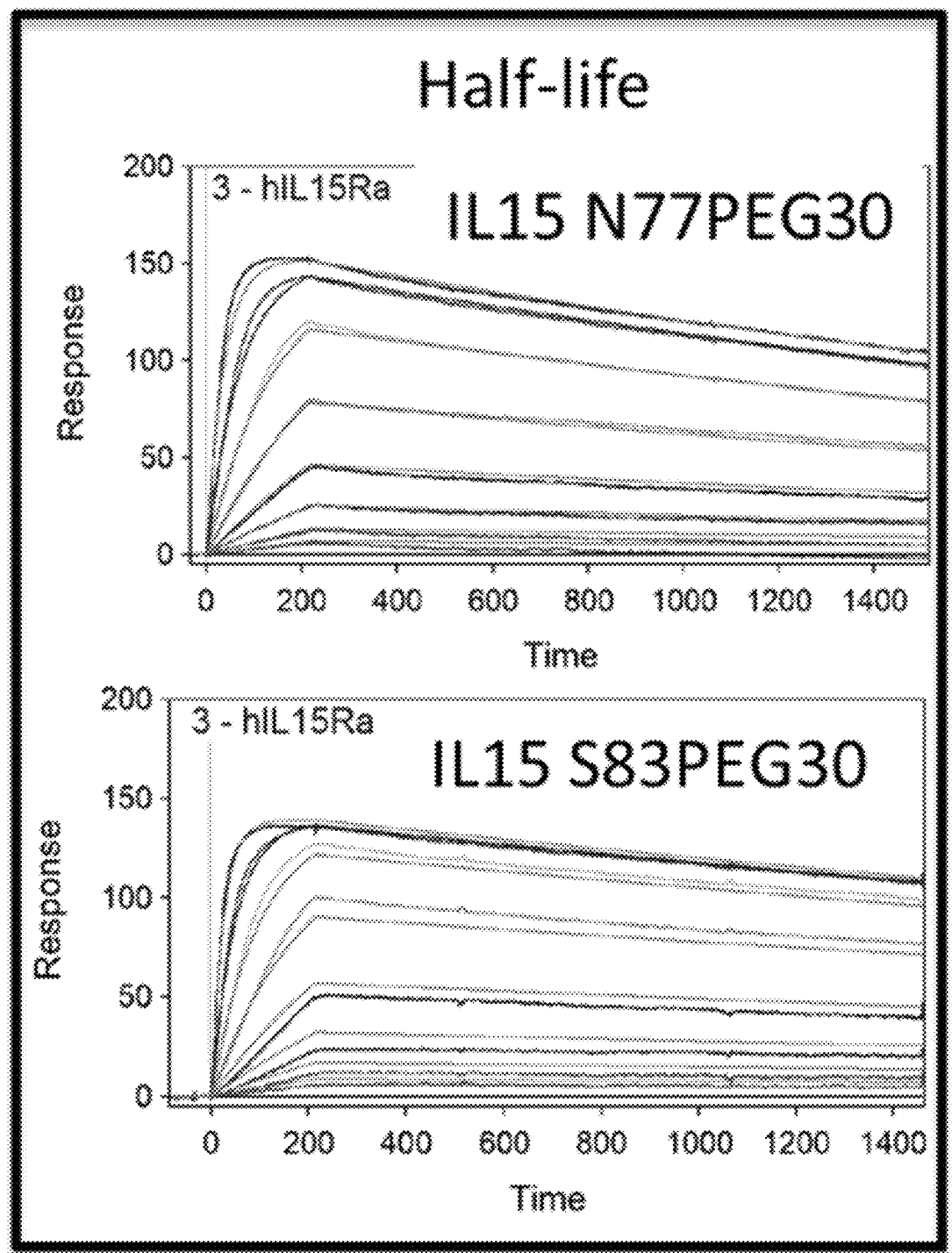

On sensor surfaces containing immobilized IL-15Rα, native IL-15 (rHuIL-15 and commercial IL-15 from R&D) showed rapid association and very slow dissociation kinetics, demonstrating very high-affinity binding (FIG. 9A). IL-15 pegylated variants designed to extend half-life without blocking interaction with IL-15 receptors show similar binding kinetics to native IL-15. The modest difference in $K_D$ (~10- and ~3-fold decreased KD for IL-15 N77PEG30 and IL-15 S83PEG30, respectively) observed between compounds for the subunit is due to the decreased on-rate of IL-15 conjugated compounds relative to rHuIL-15, expected from the lower diffusion coefficient of the pegylated compound and non-specific shielding effects of the large PEG moiety on distant binding surfaces (FIG. 9B). In contrast, IL-15 E46PEG30 interacts with IL-15 Rα with slow association and slow dissociation while IL-15 E53PEG30 shows fast association and fast dissociation (FIG. 9C) due to the specific localization of the PEG moiety on the IL-15Rα binding surface.

Surfaces containing immobilized IL-2 Rβ showed comparable association and dissociation responses with both native IL-15 and compounds designed for half-life extension with native receptor engagement. Compounds in which the PEG moiety is localized to the IL-15Rα binding surface show different binding kinetics to the IL-2Rβ surfaces. While IL-15 E46PEG30 and IL-15 L25PEG show ~10- and ~30-fold reduced binding to these surface, IL-15 E53PEG30 retains "native" binding to IL-2Rβ. These results suggest that the specific localization of the PEG moiety can confer different modalities for IL-15 interaction with its receptor.

Figure 9C:
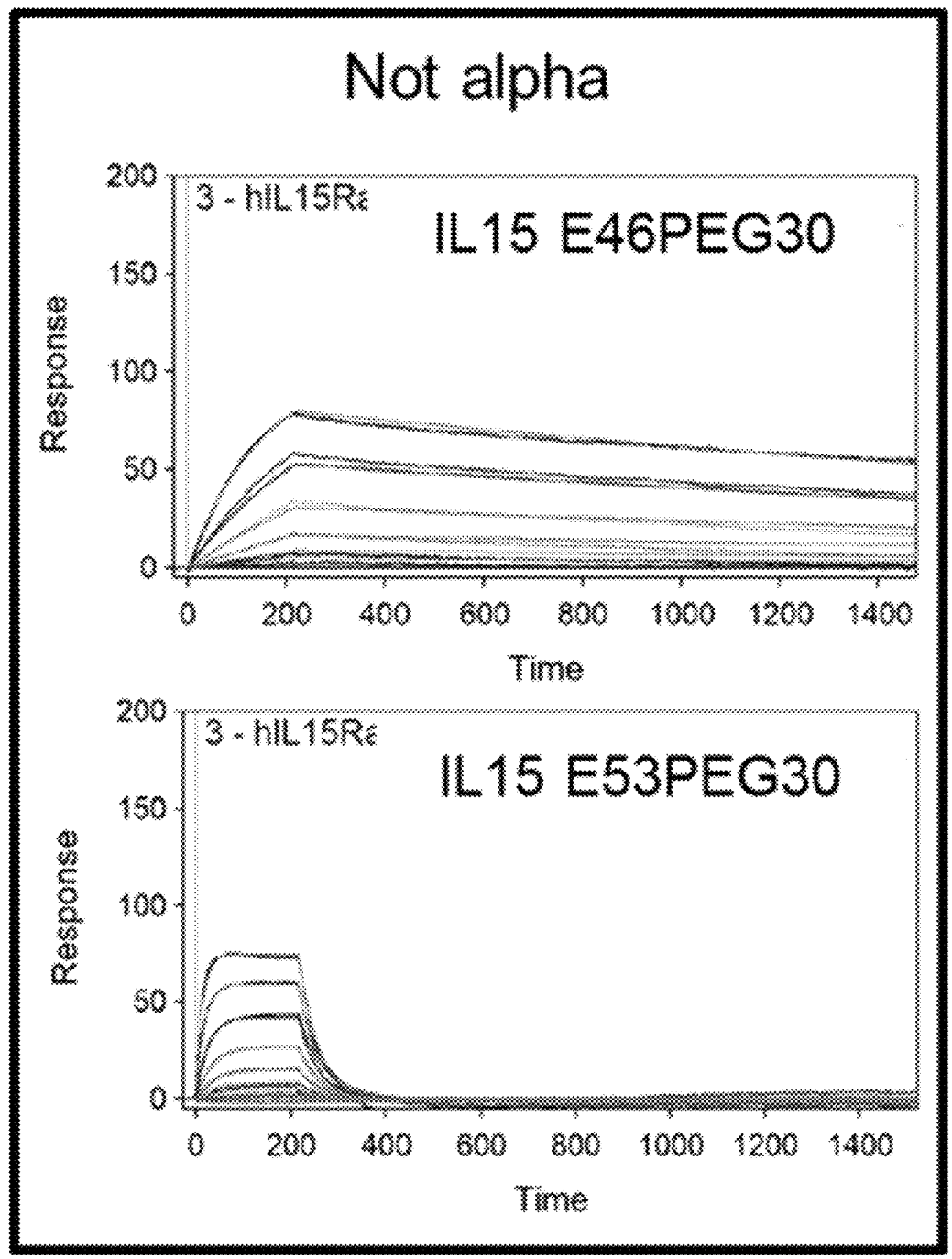

FIG. 9A-FIG. 9C show response units (RU, Y-axis) versus time (s, X-axis) for rHuIL-15, an IL-15 conjugated compounds binding to IL-15Rα. Binding kinetics analysis confirms site-specific pegylation modulates the interaction with IL-15Rα.

Figure 10:
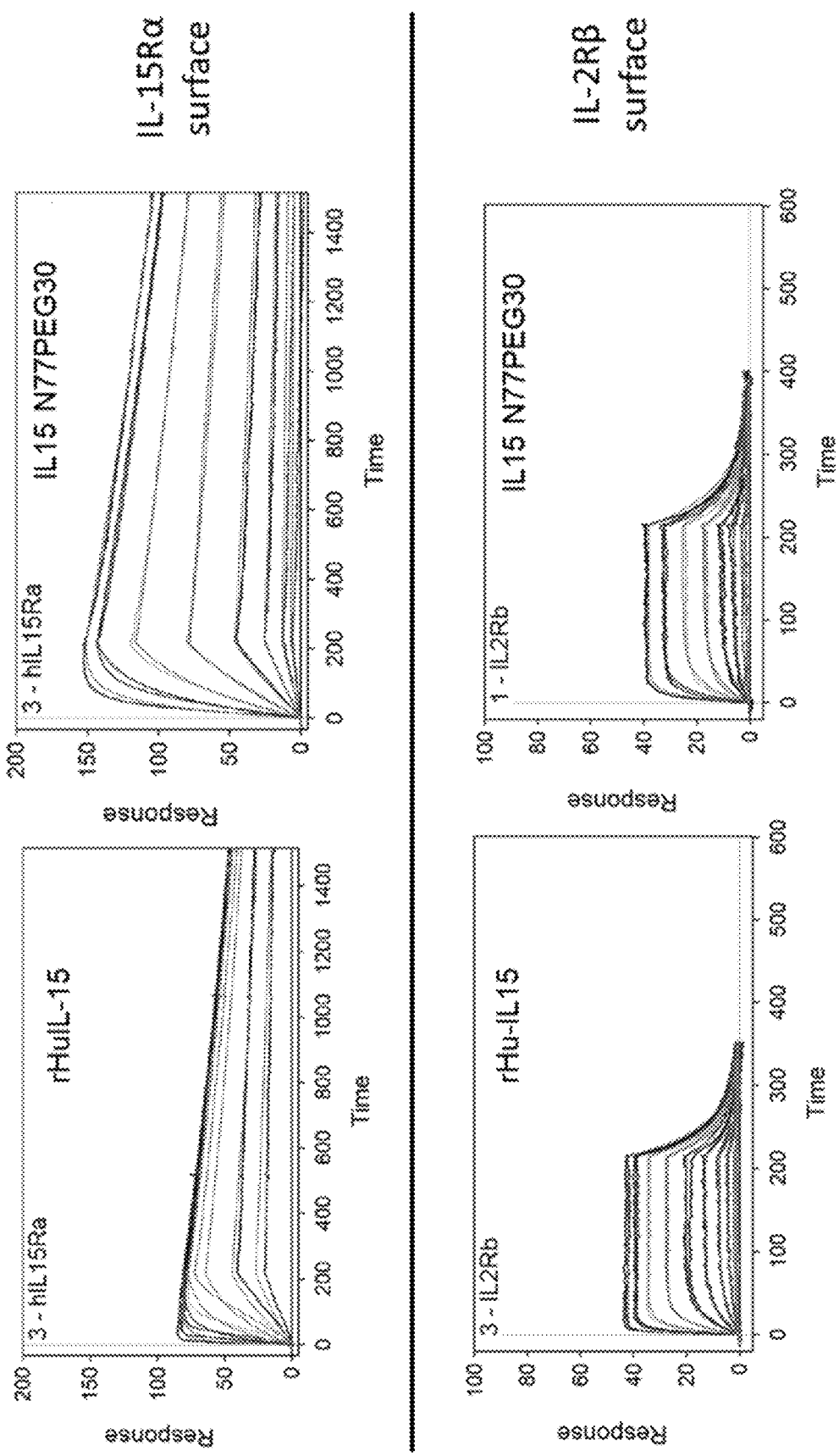
FIG. 10 shows response units (RU, Y-axis) versus time (s, X-axis) for rHuIL-15, an IL-15 N77PEG30 binding to IL-15Rα and IL-2Rβ.

FIG. 10 shows response units (RU, Y-axis) versus time (s, X-axis) for rHuIL-15, an IL-15 N77PEG30 binding to IL-15Rα and IL-2Rβ. Binding kinetics analysis confirms site-specific pegylation at position N77 retains native interaction with IL-15Rα and IL-2Rβ.

Figure 11:
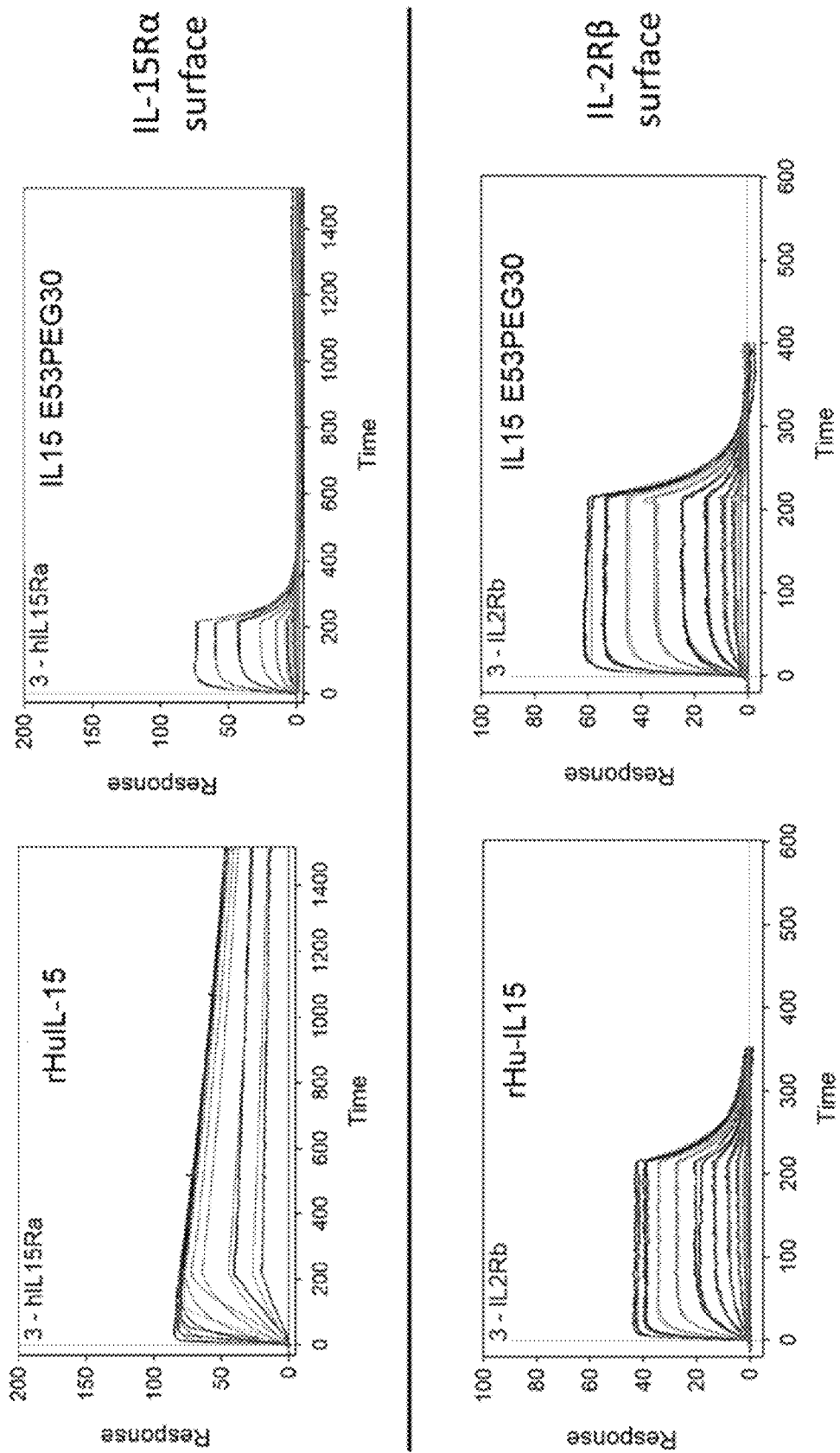
FIG. 11 shows response units (RU, Y-axis) versus time (s, X-axis) for rHuIL-15, an IL-15 E53PEG30 binding to IL-15Rα and IL-2Rβ.
Figures 12A, 12B, 12C, 12D:
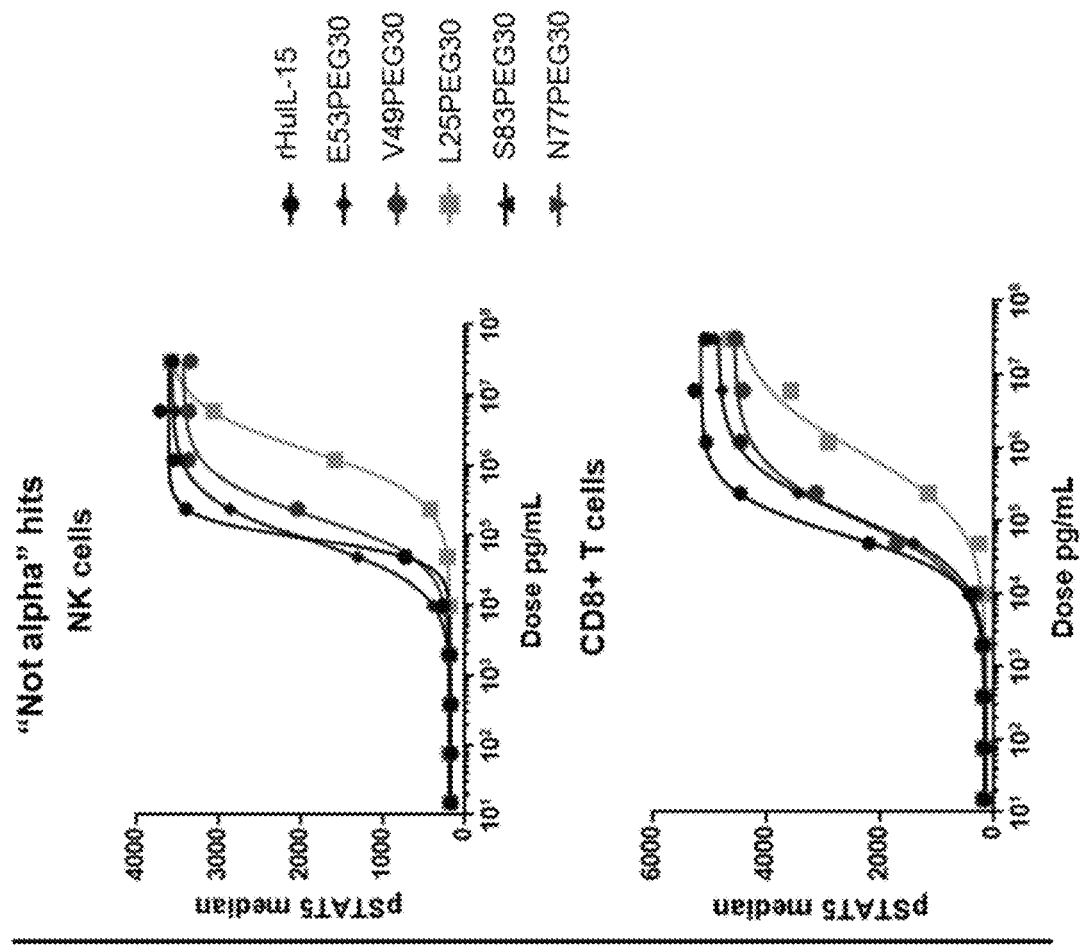
FIG. 12A-FIG. 12D illustrate STAT5 phosphorylation on NK and CD8+ T cells upon stimulation with exemplary IL-15 PEG conjugates.

FIG. 11 shows response units (RU, Y-axis) versus time (s, X-axis) for rHuIL-15, an IL-15 E53PEG30 binding to IL-15Rα and IL-2Rβ. Binding kinetics analysis confirms site-specific pegylation at position E53 reduces binding to IL-15Rα while retaining native interaction with IL-2Rβ.

Example 4

Ex-Vivo Immune Response Profiling of IL-15 PEG Conjugates in Primary Human Leukocyte Reduction System (LRS)-Derived PBMC Samples To determine how the differential receptor specificity of IL-15 PEG conjugates effects activation of primary immune cell subpopulations, concentration-response profiling of lymphocyte activation in human LRS-derived peripheral blood mononuclear cell (PBMC) samples were performed using multi-color flow cytometry. These studies were performed at PrimityBio LLC (Fremont, Calif.). Fresh LRS-derived samples were treated with either rHuIL-15 or different IL-15 pegylated compounds in 5-fold dilution series starting with a top concentration of 30 µg/mL. Treated cell populations were incubated at 37° C. for 45 minutes before addition of BD Lyse/Fix Buffer and staining with the fluorescent antibody panel shown in Table 11. Multi-color flow cytometry was used to detect and quantify pSTAT5 activation in different Tcell and NK cell subsets. Flow cytometry data were analyzed for activation of different T and NK cell subsets in concentration-response mode, reading pSTAT5 accumulation after treatment with rHuIL-15 or IL-15 pegylated compounds.

TABLE 11

Staining panel for flow cytometry study of LRS-derived PBMC samples

| Panels | Human |
|---|---|
| Pan-T | CD3 |
| CD4 | CD4 |
| CD8 | CD8 |
| NK marker | CD7 |
| Treg | FoxP3 |
| Treg | CD25 |
| | (or CD127) |
| CD45RA | CD45RA |
| C62L | C62L |
| CD14/CD19 | CD14/CD19 |
| Phospho | STAT5 |
| | (pY694) |

In NK and effector T cell (CD3+CD8$^+$) populations, IL-15 N77PEG30 and IL-15 S83PEG30 retained potency relative to rHuIL-15, with $EC_{50}$ values for pSTAT5 production within 2-fold of the native cytokine. In contrast, the EC50 values for pSTAT5 induction for IL-15 L25PEG30 in CD8+ T and NK cell populations was reduced by ~14 and ~18-fold, respectively, compared to rHuIL-15. The substantial increase in $EC_{50}$ for IL-15 L25PEG30 indicates that pegylation of IL-15 at this position reduces agonism of IL-15 receptors. The $EC_{50}$ values for pSTAT5 induction for IL-15 E53PEG30 in CD8+ T and NK cell populations was reduced by only ~2-foldcompared to rHuIL-15. Considering this compound shows fast association and fast dissociation binding kinetics to IL-15Rα.

Table 12 shows the dose response for STAT5 signaling ($EC_{50}$) in human LRS samples treated with rHuIL-15 or IL-15 conjugates.

| Compounds | CD8 + T cells EC50 (ng/ml) | NK cells EC50 (ng/ml) | CD4 + T cells EC50 (ng/ml) | Treg EC50 (ng/ml) |
|---|---|---|---|---|
| rHuIL-15 | 63.6 | 88.3 | 73.7 | 34.7 |
| IL-15 S83PEG30 | 59.4 | 137.8 | 83.3 | 19.2 |
| IL-15 N77PEG30 | 74.0 | 156.2 | 95.6 | 18.2 |
| IL-15 V49PEG30 | 100.9 | 180.2 | 135.1 | 32.6 |
| IL-15 V49PEG40b | 205.8 | 261.8 | 264.0 | 57.4 |
| IL-15 E53PEG30 | 117.3 | 82.4 | 186.8 | 37.1 |
| IL-15 L25PEG30 | 896.1 | 1,654 | 1,232.1 | 267.3 |

FIG. 12A-FIG. 12D illustrate STAT5 phosphorylation on NK and CD8+ T cells upon stimulation with exemplary IL-15 PEG conjugates.

Example 5

In Vivo Pharmacology Study of Exemplary IL-15 Conjugates

PK Studies in Naïve (E3826-U1821) C57BL/6 Mice

Mice were dosed with either rHuIL-15 and IL-15 conjugates S83-PEG 30 kDa, V49-PEG 30 kDa, L25-PEG 30 kDa or N77-PEG 30 kDa at 0.3 mg/Kg. Blood was drawn at the following time points: 0.25, 0.5, 2, 8, 24, 48, 72, 96, 120, 144 and 192 hours.

Table 13 shows the experimental setup. Each mouse received a single IV dose of either vehicle, rHuIL-15, or one of the three IL-15 conjugates.

| Group | Treatment | Dose (mg/Kg) |
|---|---|---|
| 1 | Vehicle | 0 |
| 2 | rHuIL-15 | 0.3 |
| 3 | L25 PEG30 | 0.3 |
| 4 | N77 PEG30 | 0.3 |
| 5 | V49 PEG30 | 0.3 |
| 6 | S83 PEG30 | 0.3 |

Concentrations of rHuIL-15, IL-15 pegylated compounds and the internal standard in samples derived from plasma were determined using an ELISA assay. PK data analysis was performed at NW Solutions (Seattle, Wash.). The PK data were imported into Phoenix WinNonlin v6.4 (Certara/Pharsight, Princeton, N.J.) for analysis. The group mean plasma concentration versus time data were analyzed with a 3-compartmental method using an IV bolus administration model.

Table 14 shows the extended half-life of the IL-15 conjugates in mice relative to rHuIL-15.

IL-15 conjugate S83-PEG 30 kDa at 0.1, 0.3 or 1 mg/Kg (Table 10). Blood was drawn at the following time points: 0.25, 0.5, 2, 8, 24, 48, 72, 96, 120, 144 and 192 hours. An additional 0.13 time point was included for rHuIL-15 given the known short half-life. PD readouts included intracellular pSTAT5 monitoring, and phenotyping of CD8+ T cells for all time points.

Table 15 shows the experimental setup. Each mouse received a single IV dose of either vehicle, rHuIL-15, or one of the three IL-15 conjugates.

| Group | Treatment | Dose (mg/Kg) |
|---|---|---|
| 1 | Vehicle | 0 |
| 2 | rHuIL-15 | 0.3 |
| 3 | S18 PEG30 | 0.1 |
| 4 | S18 PEG30 | 0.3 |
| 5 | V49 PEG30 | 0.1 |
| 6 | V49 PEG30 | 0.3 |
| 7 | L25 PEG30 | 0.3 |
| 8 | L25 PEG30 | 1.0 |

STAT5 phosphorylation and induction of cell proliferation (the early molecular marker Ki-67 and cell counts) was used as pharmacodynamic readouts to assess the pharmacological profile of IL-15 S18PEG30, IL-15 V49PEG30 and IL-15 L25 PEG30. While lower or similar elevation of pSTAT5

| Dose (mg/kg) | Parameter | Units | Group 2 rHuIL-15 | Group 3 L25PEG | Group 4 N77PEG Estimate | Group 5 V49PEG | Group 6 S83PEG |
|---|---|---|---|---|---|---|---|
| 0.3 | alpha $t_{1/2}$ | hr | 0.305 | 2.89 | 0.0349 | 0.242 | 0.381 |
| | beta $t_{1/2}$ | hr | 1.08 | 15.8 | 13.1 | 7.77 | 11.4 |
| | gamma $t_{1/2}$ | hr | 32.1 | 167 | 58.4 | 19.8 | 71.6 |
| | MRT | hr | 3.81 | 21.2 | 20.5 | 20.6 | 18.7 |
| | $CL_1$ | mL/hr/kg | 1590 | 6.16 | 5.17 | 4.69 | 9.13 |
| | $CL_2$ | mL/hr/kg | 333 | 5.68 | 56.4 | 52.4 | 65.4 |
| | $CL_3$ | mL/hr/kg | 108 | 0.0317 | 0.157 | 1.03 | 0.213 |
| | $V_1$ | mL/kg | 978 | 82.3 | 3.20 | 32.8 | 79.0 |
| | $V_2$ | mL/kg | 397 | 40.7 | 89.8 | 44.9 | 70.1 |
| | $V_3$ | mL/kg | 4680 | 7.59 | 12.8 | 19.1 | 21.4 |
| | $V_{SS}$ | mL/kg | 6050 | 131 | 106 | 96.8 | 170 |
| | $C_{max}$ | ng/mL | 307 | 3650 | 93700 | 9140 | 3800 |
| | AUC | hr*ng/mL | 189 | 48700 | 58100 | 64000 | 32900 |

Figure 13:
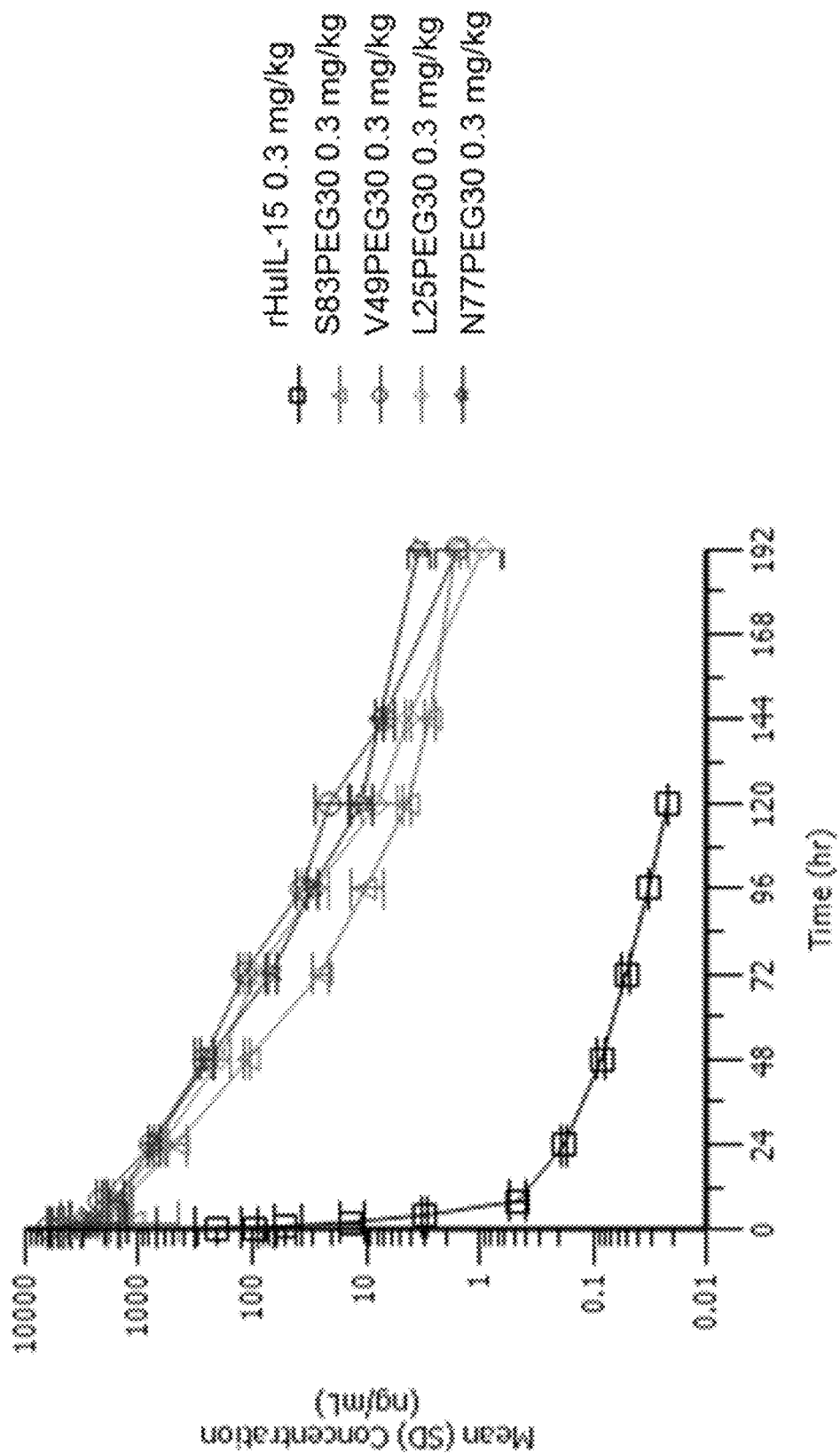
FIG. 13 shows plasma concentration profiles of rHuIL-15, IL-15 S83PEG30, IL-15 V49PEG30 IL-15 L25 PEG30 and IL-15 N77 PEG30 at 0.3 mg/kg.

FIG. 13 shows plasma concentration profiles of rHuIL-15, IL-15 S83PEG30, IL-15 V49PEG30, IL-15 N77PEG30 and IL-15 L25 PEG30 at 0.3 mg/kg.

As expected, pegylated compounds exhibit a superior PK profile relative to rHuIL-15 as summarized on Table 14. The MRT (mean residence time) represents the average time a test article molecule stays in the body and takes into account the entire PK profile. Pegylated compounds show a ~5-fold increase in MRT compared to rHuIL-15. IL-15 S18PEG30 demonstrated ~15-fold extended beta t½ (15.8 h vs. 1.08 h) and about 59-fold reduced $CL_2$ (5.68 vs 333 mL/h/Kg) compared to the rHuIL-15. The distribution volume for pegylated compounds was reduced relative to rHuIL_15 suggesting that pegylated compounds are mostly distributed within systemic circulation.

Example 6

Pharmacodynamic Observations in Peripheral Blood Compartment

PD Studies in Naïve (E3826-U1821) C57BL/6 Mice

Mice were dosed with either rHuIL-15, IL-15 conjugate S18-PEG 30 kDa, IL-15 conjugate V49-PEG 30 kDa or was observed in mice dosed with pegylated compounds, STAT5 phosphorylation translated into a higher proliferation and sustained (days 1 to 7 post-dose) of NK cells and CD8+ effector and memory T cells but not Treg cells. (FIGS. 14-17).

FIG. 14A-FIG. 14D show % pSTAT5 in different peripheral blood cell populations.

FIG. 15A-FIG. 15D show increased expression of the early proliferation molecular marker Ki67 in CD8+ T, CD8+ Tmem and NK cells but not Treg cells in animals dosed with pegylated compounds.

FIG. 16A-FIG. 16C show robust peripheral CD8+ T, CD8+ Tmem and NK cells but not Treg cells in animals dosed with pegylated compounds.

Figure 17A:
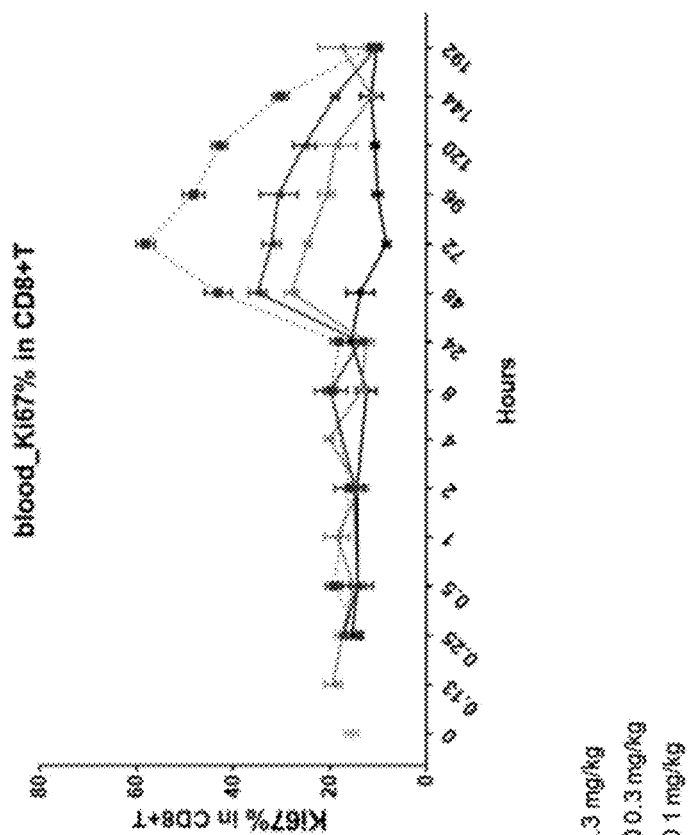
FIG. 17A-FIG. 17B show increased Ki67 expression in NK cells (FIG. 17A) and CD8+ T (FIG. 17B) with increased dose of IL-15 L25PEG30 compound in mice.
Figure 17B:
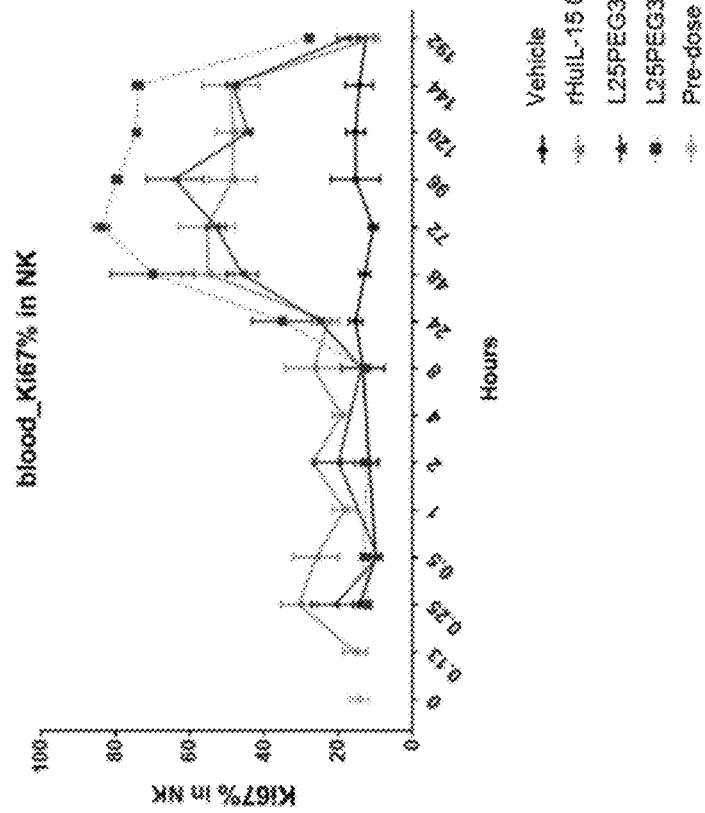

FIG. 17A-FIG. 17B show increased Ki67 expression in CD8+ T and NK cells with increased dose of IL-15 L25PEG30 compound in mice.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A modified interleukin 15 (IL-15) polypeptide comprising at least one unnatural amino acid and a conjugating moiety covalently attached to the at least one unnatural amino acid, wherein the at least one unnatural amino acid has a residue position selected from L25, E46, V49, E53, N77, and S83, wherein the residue position corresponds to the positions as set forth in SEQ ID NO: 1, and wherein the modified IL-15 polypeptide comprises at least about 90% sequence identity to SEQ ID NO: 1.

2. The modified IL-15 polypeptide of claim 1, wherein the at least one unnatural amino acid:
   is a lysine analogue;
   comprises an aromatic side chain;
   comprises an azido group;
   comprises an alkyne group; or comprises an aldehyde or ketone group.

3. The modified IL-15 polypeptide of claim 2, wherein the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine.

4. The modified IL-15 polypeptide of claim 1, wherein the conjugating moiety comprises a water-soluble polymer, a lipid, a protein, or a peptide.

5. The modified IL-15 polypeptide of claim 4, wherein the conjugating moiety comprises a water-soluble polymer, and wherein the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly (hydroxyalkylmethacrylamide), poly(hydroxyalkylmethacrylate), poly(saccharides), poly(a-hydroxy acid), poly(vinyl alcohol), polyphosphazene, polyoxazolines (POZ), poly (N-acryloylmorpholine), or a combination thereof.

6. The modified IL-15 polypeptide of claim 4, wherein the conjugating moiety comprises a water-soluble polymer, and wherein the water-soluble polymer comprises PEG.

7. The modified IL-15 polypeptide of claim 6, wherein the PEG is a linear PEG.

8. The modified IL-15 polypeptide of claim 1, wherein the conjugating moiety is bound to the at least one unnatural amino acid of the modified IL-15 polypeptide through a linker.

9. The modified IL-15 polypeptide of claim 8, wherein the linker comprises a homobifunctional linker, a heterobifunctional linker, a cleavable or a non-cleavable dipeptide linker, a spacer, or a combination thereof.

10. The modified IL-15 polypeptide of claim 1, wherein the modified IL-15 polypeptide comprises an N-terminal deletion of the first 1, 2, 3, 4, 5, 6, 7, 8, 9, or 10 residues from the N-terminus, wherein the residue positions are in reference to the positions in SEQ ID NO: 1.

11. A pharmaceutical composition comprising the modified IL-15 polypeptide of claim 1 and a pharmaceutically acceptable excipient.

12. The pharmaceutical composition of claim 11, wherein the pharmaceutical composition is formulated for parenteral administration.

13. The modified IL-15 polypeptide of claim 6, wherein the PEG has a weight-average molecular weight from about 20 kDa to about 85 kDa.

14. The modified IL-15 polypeptide of claim 13, wherein the PEG has a weight-average molecular weight of about 20 kDa, about 25 kDa, about 30 kDa, about 35 kDa, about 40 kDa, about 45 kDa, or about 50 kDa.

15. The modified IL-15 polypeptide of claim 1, wherein the modified IL-15 polypeptide comprises the amino acid sequence of SEQ ID NO: 1, wherein one amino acid is replaced by the at least one unnatural amino acid.

16. The modified IL-15 polypeptide of claim 1, wherein the residue position of the at least one unnatural amino acid is E46.

17. The modified IL-15 polypeptide of claim 1, wherein the residue position of the at least one unnatural amino acid is V49.

18. The modified IL-15 polypeptide of claim 1, wherein the residue position of the at least one unnatural amino acid is E53.

19. The modified IL-15 polypeptide of claim 1, wherein the residue position of the at least one unnatural amino acid is L25.

20. The modified IL-15 polypeptide of claim 1, wherein the residue position of the at least one unnatural amino acid is S83.

21. The modified IL-15 polypeptide of claim 1, wherein the residue position of the at least one unnatural amino acid is N77.

* * * * *